(12) United States Patent
Scheib et al.

(10) Patent No.: US 12,376,883 B2
(45) Date of Patent: Aug. 5, 2025

(54) UTERINE MANIPULATOR CONTROL WITH PRESENTATION OF CRITICAL STRUCTURES

(71) Applicant: Cilag GmbH International, Zug (CH)

(72) Inventors: Charles J. Scheib, Loveland, OH (US); Matthew Vargas, San Francisco, CA (US); Clinton Denlinger, Cincinnati, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 669 days.

(21) Appl. No.: 17/468,772

(22) Filed: Sep. 8, 2021

(65) Prior Publication Data
US 2023/0075988 A1 Mar. 9, 2023

(51) Int. Cl.
| | | |
|---|---|---|
| A61B 17/42 | (2006.01) | |
| A61B 1/00 | (2006.01) | |
| A61B 1/303 | (2006.01) | |
| A61B 34/00 | (2016.01) | |
| A61B 34/30 | (2016.01) | |
| A61G 13/10 | (2006.01) | |
| A61B 17/00 | (2006.01) | |
| A61B 34/20 | (2016.01) | |
| A61B 90/00 | (2016.01) | |
| A61M 25/10 | (2013.01) | |

(52) U.S. Cl.
CPC ...... *A61B 17/4241* (2013.01); *A61B 1/00045* (2013.01); *A61B 1/00087* (2013.01); *A61B 1/00149* (2013.01); *A61B 1/303* (2013.01); *A61B 34/25* (2016.02); *A61B 34/30* (2016.02); *A61G 13/10* (2013.01); *A61B 2017/00199* (2013.01); *A61B 2017/4216* (2013.01); *A61B 2017/4225* (2013.01); *A61B 2034/2065* (2016.02); *A61B 2034/252* (2016.02); *A61B 2034/302* (2016.02); *A61B 2034/303* (2016.02); *A61B 90/361* (2016.02); *A61B 2090/365* (2016.02); *A61M 25/10* (2013.01)

(58) Field of Classification Search
CPC ............... A61B 17/42; A61B 17/4241; A61B 2017/4225; A61B 34/30; A61M 25/10
See application file for complete search history.

(56) References Cited

U.S. PATENT DOCUMENTS

| | | |
|---|---|---|
| 9,274,047 B2 | 3/2016 | Velten et al. |
| 9,743,955 B2 | 8/2017 | Hill et al. |
| 9,763,741 B2 | 9/2017 | Alvarez et al. |
| 9,788,859 B2 | 10/2017 | Parys |
| 10,464,209 B2 | 11/2019 | Ho et al. |
| 10,639,072 B2 | 5/2020 | Ahluwalia |

(Continued)

*Primary Examiner* — Vi X Nguyen
(74) *Attorney, Agent, or Firm* — Joshua D. Young

(57) ABSTRACT

A system includes a uterine manipulator having a shaft. The uterine manipulator is coupled with the robotic arm. An imaging instrument is operable to provide an image of an exterior of the uterus of the patient. A console includes a display screen and is configured to provide a view from the imaging instrument of the exterior of the uterus of the patient, on the display screen. The console is further configured to provide an indicator on the view from the imaging instrument, on the display screen, the indicator indicating a location of a predefined anatomical structure, the indicator being provided as an overlay on the predefined anatomical structure.

13 Claims, 36 Drawing Sheets

(56) References Cited

U.S. PATENT DOCUMENTS

| | | |
|---|---|---|
| 10,667,875 B2 | 6/2020 | DeFonzo et al. |
| 10,765,303 B2 | 9/2020 | Graetzel et al. |
| 10,827,913 B2 | 11/2020 | Ummalaneni et al. |
| 10,881,280 B2 | 1/2021 | Baez, Jr. |
| 10,898,277 B2 | 1/2021 | Srinivasan et al. |
| 11,058,493 B2 | 7/2021 | Rafii-Tari et al. |
| 2003/0109780 A1* | 6/2003 | Coste-Maniere ..... G06T 7/0012 600/407 |
| 2005/0165271 A1 | 7/2005 | Shioda et al. |
| 2009/0326318 A1* | 12/2009 | Tognaccini ............ A61B 34/37 600/109 |
| 2017/0055819 A1 | 3/2017 | Hansen et al. |
| 2017/0251900 A1 | 9/2017 | Hansen et al. |
| 2018/0325552 A1 | 11/2018 | Weihe et al. |
| 2020/0015898 A1 | 1/2020 | Scheib et al. |
| 2020/0015899 A1 | 1/2020 | Scheib et al. |
| 2020/0015924 A1 | 1/2020 | Scheib et al. |
| 2020/0015925 A1 | 1/2020 | Scheib |
| 2021/0100584 A1 | 4/2021 | Einarsson |
| 2021/0137612 A1 | 5/2021 | Staid et al. |
| 2023/0073575 A1* | 3/2023 | Scheib .................. A61B 34/25 |

\* cited by examiner

UTERINE MANIPULATOR CONTROL WITH PRESENTATION OF CRITICAL STRUCTURES

BACKGROUND

A variety of medical instruments may be used in procedures conducted by a medical professional operator, as well as applications in robotically assisted surgeries. In the case of robotically assisted surgery, the clinician may operate a master controller to remotely control the motion of such medical instruments at a surgical site. The controller may be separated from the patient by a significant distance (e.g., across the operating room, in a different room, or in a completely different building than the patient). Alternatively, a controller may be positioned quite near the patient in the operating room. Regardless, the controller may include one or more hand input devices (such as joysticks, exoskeletal gloves, master manipulators, or the like), which are coupled by a servo mechanism to the medical instrument. In some scenarios, a servo motor moves a manipulator supporting the medical instrument based on the clinician's manipulation of the hand input devices. During the medical procedure, the clinician may employ, via a robotic system, a variety of medical instruments including an ultrasonic blade, a surgical stapler, a tissue grasper, a needle driver, an electrosurgical cautery probes, etc. Each of these structures performs functions for the clinician, for example, cutting tissue, coagulating tissue, holding or driving a needle, grasping a blood vessel, dissecting tissue, or cauterizing tissue.

Examples of robotic systems are described in U.S. Pat. No. 9,763,741, entitled "System for Robotic-Assisted Endolumenal Surgery and Related Methods," issued Sep. 19, 2017, the disclosure of which is incorporated by reference herein, in its entirety; U.S. Pat. No. 10,464,209, entitled "Robotic System with Indication of Boundary for Robotic Arm," issued Nov. 5, 2019, the disclosure of which is incorporated by reference herein, in its entirety; U.S. Pat. No. 10,667,875, entitled "Systems and Techniques for Providing Multiple Perspectives During Medical Procedures," issued Jun. 2, 2020, the disclosure of which is incorporated by reference herein, in its entirety; U.S. Pat. No. 10,765,303, entitled "System and Method for Driving Medical Instrument," issued Sep. 8, 2020, the disclosure of which is incorporated by reference herein, in its entirety; U.S. Pat. No. 10,827,913, entitled "Systems and Methods for Displaying Estimated Location of Instrument," issued Nov. 10, 2020, the disclosure of which is incorporated by reference herein, in its entirety; U.S. Pat. No. 10,881,280, entitled "Manually and Robotically Controllable Medical Instruments," issued Jan. 5, 2021, the disclosure of which is incorporated by reference herein, in its entirety; U.S. Pat. No. 10,898,277, entitled "Systems and Methods for Registration of Location Sensors," issued Jan. 26, 2012, the disclosure of which is incorporated by reference herein, in its entirety; and U.S. Pat. No. 11,058,493, entitled "Robotic System Configured for Navigation Path Tracing," issued Jul. 13, 2021, the disclosure of which is incorporated by reference herein, in its entirety.

During a hysterectomy procedure, a colpotomy may be performed at the cervicovaginal junction. Such procedures may include the use of a uterine manipulator that includes a colpotomy cup or similar structure. Examples of instruments that may be used during a hysterectomy procedure are described in U.S. Pat. No. 9,743,955, entitled "Intracorporeal Transilluminator of Tissue Using LED Array," issued Aug. 29, 2017; U.S. Pat. No. 9,788,859, entitled "Uterine Manipulators and Related Components and Methods," issued Oct. 17, 2017; U.S. Pat. No. 10,639,072, entitled "Uterine Manipulator," issued May 5, 2020; U.S. Pub. No. 2021/0100584, entitled "Uterine Manipulator," published Apr. 8, 2021; U.S. Pub. No. 2018/0325552, entitled "Colpotomy Systems, Devices, and Methods with Rotational Cutting," published Nov. 15, 2018.

While several medical instruments, systems, and methods have been made and used, it is believed that no one prior to the inventors has made or used the invention described in the appended claims.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

I. Overview of Example of Robotic System

Aspects of the present disclosure may be integrated into a robotically-enabled medical system capable of performing a variety of medical procedures, including both minimally invasive, such as laparoscopy, and non-invasive, such as endoscopy, procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Example of Robotic System Cart

Figure 1:
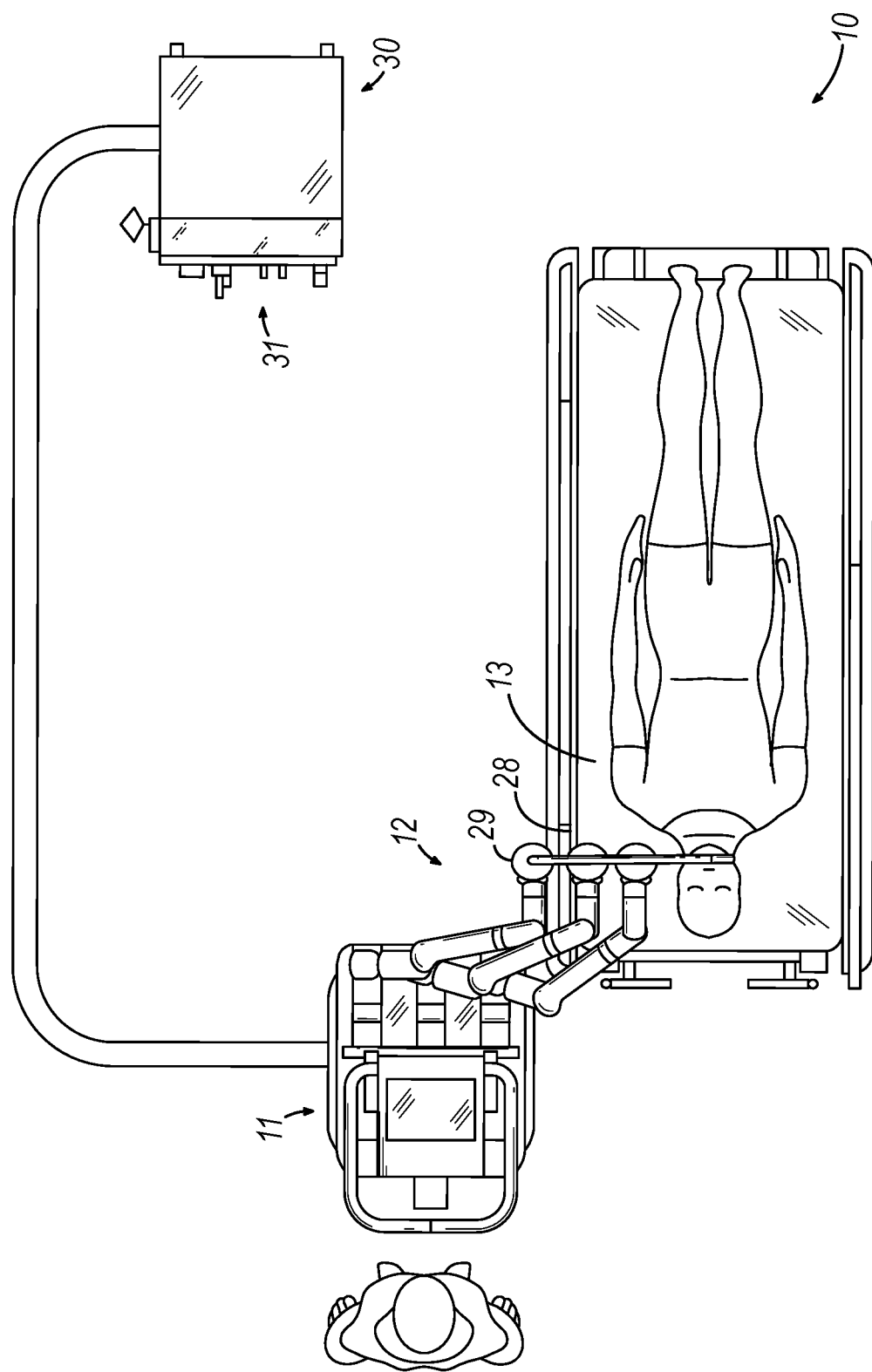
FIG. 1 depicts an embodiment of a cart-based robotic system arranged for diagnostic and/or therapeutic bronchoscopy procedure(s).
Figure 2:
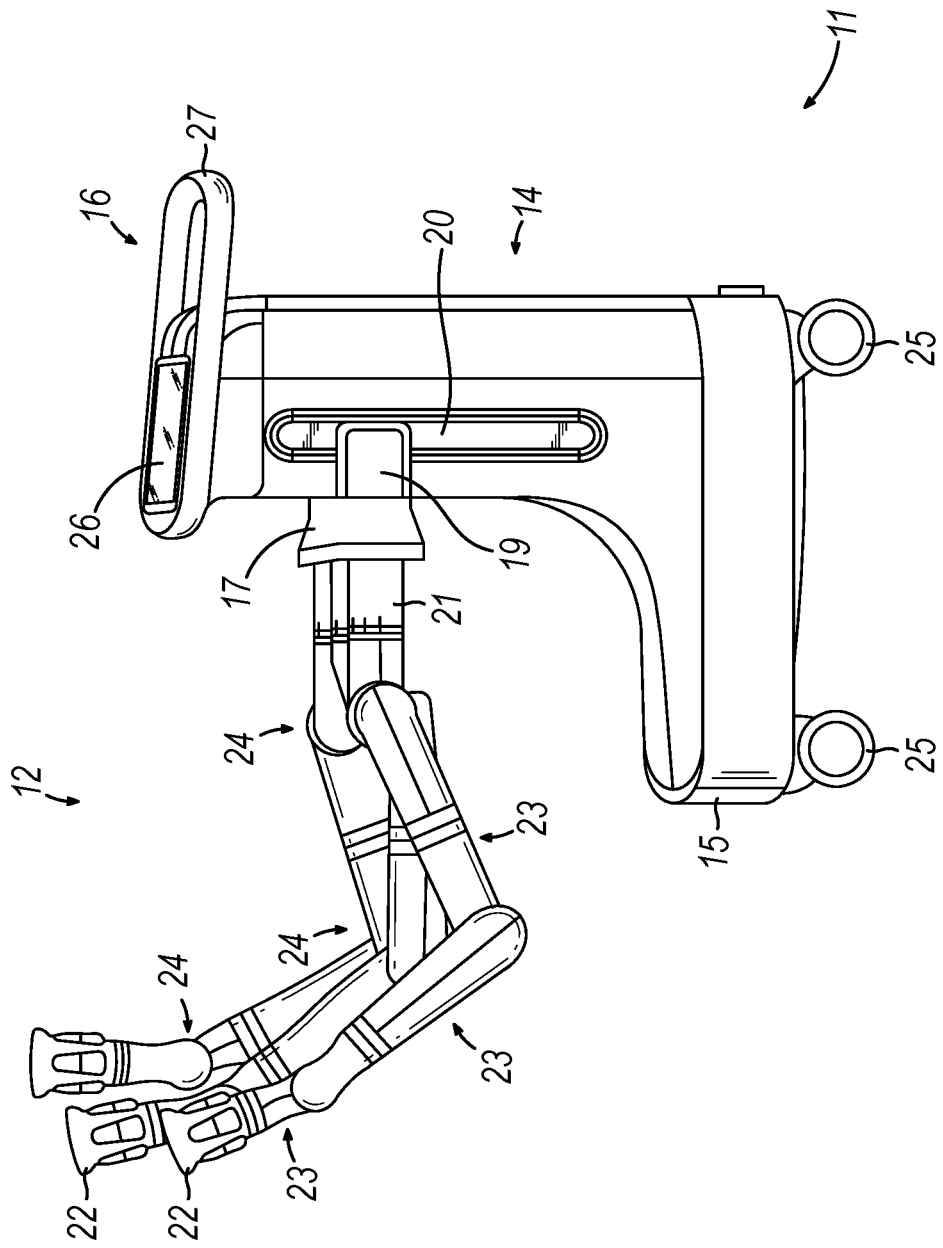
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system (10) arranged for a diagnostic and/or therapeutic bronchoscopy procedure. During a bronchoscopy, the system (10) may comprise a cart (11) having one or more robotic arms (12) to deliver a medical instrument, such as a steerable endoscope (13), which may be a procedure-specific bronchoscope for bronchoscopy, to a natural orifice access point (i.e., the mouth of the patient positioned on a table in the present example) to deliver diagnostic and/or therapeutic tools. As shown, the cart (11) may be positioned proximate to the patient's upper torso in order to provide access to the access point. Similarly, the robotic arms (12) may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart (11) is properly positioned, the robotic arms (12) may insert the steerable endoscope (13) into the patient robotically, manually, or a combination thereof. As shown, the steerable endoscope (13) may comprise at least two telescoping parts, such as an inner leader portion and an outer sheath portion, each portion coupled to a separate instrument driver from the set of instrument drivers (28), each instrument driver coupled to the distal end of an individual robotic arm. This linear arrangement of the instrument drivers (28), which facilitates coaxially aligning the leader portion with the sheath portion, creates a "virtual rail" (29) that may be repositioned in space by manipulating the one or more robotic arms (12) into different angles and/or positions. The virtual rails described herein are depicted in the Figures using dashed lines, and accordingly the dashed lines do not depict any physical structure of the system. Translation of the instrument drivers (28) along the virtual rail (29) telescopes the inner leader portion relative to the outer sheath portion or advances or retracts the endoscope (13) from the patient. The angle of the virtual rail (29) may be adjusted, translated, and pivoted based on clinical application or physician preference. For example, in bronchoscopy, the angle and position of the virtual rail (29) as shown represents a compromise between providing physician access to the endoscope (13) while minimizing friction that results from bending the endoscope (13) into the patient's mouth.

The endoscope (13) may be directed down the patient's trachea and lungs after insertion using precise commands from the robotic system until reaching the target destination or operative site. In order to enhance navigation through the patient's lung network and/or reach the desired target, the endoscope (13) may be manipulated to telescopically extend the inner leader portion from the outer sheath portion to obtain enhanced articulation and greater bend radius. The use of separate instrument drivers (28) also allows the leader portion and sheath portion to be driven independent of each other.

For example, the endoscope (13) may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope (13) may endoscopically deliver tools to resect the potentially cancerous tissue. In some instances, diagnostic and therapeutic treatments can be delivered in separate procedures. In those circumstances, the endoscope (13) may also be used to deliver a fiducial to "mark" the location of the target nodule as well. In other instances, diagnostic and therapeutic treatments may be delivered during the same procedure.

The system (10) may also include a movable tower (30), which may be connected via support cables to the cart (11) to provide support for controls, electronics, fluidics, optics, sensors, and/or power to the cart (11). Placing such functionality in the tower (30) allows for a smaller form factor cart (11) that may be more easily adjusted and/or repositioned by an operating physician and his/her staff. Additionally, the division of functionality between the cart/table and the support tower (30) reduces operating room clutter and facilitates improving clinical workflow. While the cart (11) may be positioned close to the patient, the tower (30) may be stowed in a remote location to stay out of the way during a procedure.

In support of the robotic systems described above, the tower (30) may include component(s) of a computer-based control system that stores computer program instructions, for example, within a non-transitory computer-readable storage medium such as a persistent magnetic storage drive, solid state drive, etc. The execution of those instructions, whether the execution occurs in the tower (30) or the cart (11), may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower (30) may also include a pump, flow meter, valve control, and/or fluid access in order to provide controlled irrigation and aspiration capabilities to the system that may be deployed through the endoscope (13). These components may also be controlled using the computer system of tower (30). In some embodiments, irrigation and aspiration capabilities may be delivered directly to the endoscope (13) through separate cable(s).

The tower (30) may include a voltage and surge protector designed to provide filtered and protected electrical power to the cart (11), thereby avoiding placement of a power transformer and other auxiliary power components in the cart (11), resulting in a smaller, more moveable cart (11).

The tower (30) may also include support equipment for the sensors deployed throughout the robotic system (10). For example, the tower (30) may include opto-electronics equipment for detecting, receiving, and processing data received from the optical sensors or cameras throughout the robotic system (10). In combination with the control system, such opto-electronics equipment may be used to generate real-time images for display in any number of consoles deployed throughout the system, including in the tower (30). Similarly, the tower (30) may also include an electronic subsystem for receiving and processing signals received from deployed electromagnetic (EM) sensors. The tower (30) may also be used to house and position an EM field generator for detection by EM sensors in or on the medical instrument.

The tower (30) may also include a console (31) in addition to other consoles available in the rest of the system, e.g., console mounted on top of the cart. The console (31) may include a user interface and a display screen, such as a touchscreen, for the physician operator. Consoles in system (10) are generally designed to provide both robotic controls as well as pre-operative and real-time information of the procedure, such as navigational and localization information of the endoscope (13). When the console (31) is not the only console available to the physician, it may be used by a second operator, such as a nurse, to monitor the health or vitals of the patient and the operation of system, as well as provide procedure-specific data, such as navigational and localization information. In other embodiments, the console (31) is housed in a body that is separate from the tower (30).

The tower (30) may be coupled to the cart (11) and endoscope (13) through one or more cables or connections (not shown). In some embodiments, the support functionality from the tower (30) may be provided through a single cable to the cart (11), simplifying and de-cluttering the operating room. In other embodiments, specific functionality may be coupled in separate cabling and connections. For example, while power may be provided through a single power cable to the cart, the support for controls, optics, fluidics, and/or navigation may be provided through a separate cable.

FIG. 2 provides a detailed illustration of an embodiment of the cart from the cart-based robotically-enabled system shown in FIG. 1. The cart (11) generally includes an elongated support structure (14) (often referred to as a "column"), a cart base (15), and a console (16) at the top of the column (14). The column (14) may include one or more carriages, such as a carriage (17) (alternatively "arm support") for supporting the deployment of one or more robotic arms (12) (three shown in FIG. 2). The carriage (17) may include individually configurable arm mounts that rotate along a perpendicular axis to adjust the base of the robotic arms (12) for better positioning relative to the patient. The carriage (17) also includes a carriage interface (19) that allows the carriage (17) to vertically translate along the column (14).

The carriage interface (19) is connected to the column (14) through slots, such as slot (20), that are positioned on opposite sides of the column (14) to guide the vertical translation of the carriage (17). The slot (20) contains a vertical translation interface to position and hold the carriage at various vertical heights relative to the cart base (15). Vertical translation of the carriage (17) allows the cart (11) to adjust the reach of the robotic arms (12) to meet a variety of table heights, patient sizes, and physician preferences. Similarly, the individually configurable arm mounts on the carriage (17) allow the robotic arm base (21) of robotic arms (12) to be angled in a variety of configurations.

In some embodiments, the slot (20) may be supplemented with slot covers that are flush and parallel to the slot surface to prevent dirt and fluid ingress into the internal chambers of the column (14) and the vertical translation interface as the carriage (17) vertically translates. The slot covers may be deployed through pairs of spring spools positioned near the vertical top and bottom of the slot (20). The covers are coiled within the spools until deployed to extend and retract from their coiled state as the carriage (17) vertically translates up and down. The spring-loading of the spools provides force to retract the cover into a spool when carriage (17) translates towards the spool, while also maintaining a tight seal when the carriage (17) translates away from the spool. The covers may be connected to the carriage (17) using, for example, brackets in the carriage interface (19) to ensure proper extension and retraction of the cover as the carriage (17) translates.

The column (14) may internally comprise mechanisms, such as gears and motors, that are designed to use a vertically aligned lead screw to translate the carriage (17) in a mechanized fashion in response to control signals generated in response to user inputs, e.g., inputs from the console (16).

The robotic arms (12) may generally comprise robotic arm bases (21) and end effectors (22), separated by a series of linkages (23) that are connected by a series of joints (24), each joint comprising an independent actuator, each actuator comprising an independently controllable motor. Each independently controllable joint represents an independent degree of freedom available to the robotic arm. Each of the arms (12) have seven joints, and thus provide seven degrees of freedom. A multitude of joints result in a multitude of degrees of freedom, allowing for "redundant" degrees of freedom. Redundant degrees of freedom allow the robotic arms (12) to position their respective end effectors (22) at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base (15) balances the weight of the column (14), carriage (17), and arms (12) over the floor. Accordingly, the cart base (15) houses heavier components, such as electronics, motors, power supply, as well as components that either enable movement and/or immobilize the cart. For example, the cart base (15) includes rollable wheel-shaped casters (25) that allow for the cart to easily move around the room prior to a procedure. After reaching the appropriate position, the casters (25) may be immobilized using wheel locks to hold the cart (11) in place during the procedure.

Positioned at the vertical end of column (14), the console (16) allows for both a user interface for receiving user input and a display screen (or a dual-purpose device such as, for example, a touchscreen (26)) to provide the physician user with both pre-operative and intra-operative data. Potential pre-operative data on the touchscreen (26) may include pre-operative plans, navigation and mapping data derived from pre-operative computerized tomography (CT) scans, and/or notes from pre-operative patient interviews. Intra-operative data on display may include optical information provided from the tool, sensor and coordinate information from sensors, as well as vital patient statistics, such as respiration, heart rate, and/or pulse. The console (16) may be positioned and tilted to allow a physician to access the console from the side of the column (14) opposite carriage (17). From this position, the physician may view the console (16), robotic arms (12), and patient while operating the console (16) from behind the cart (11). As shown, the console (16) also includes a handle (27) to assist with maneuvering and stabilizing cart (11).

Figure 3:
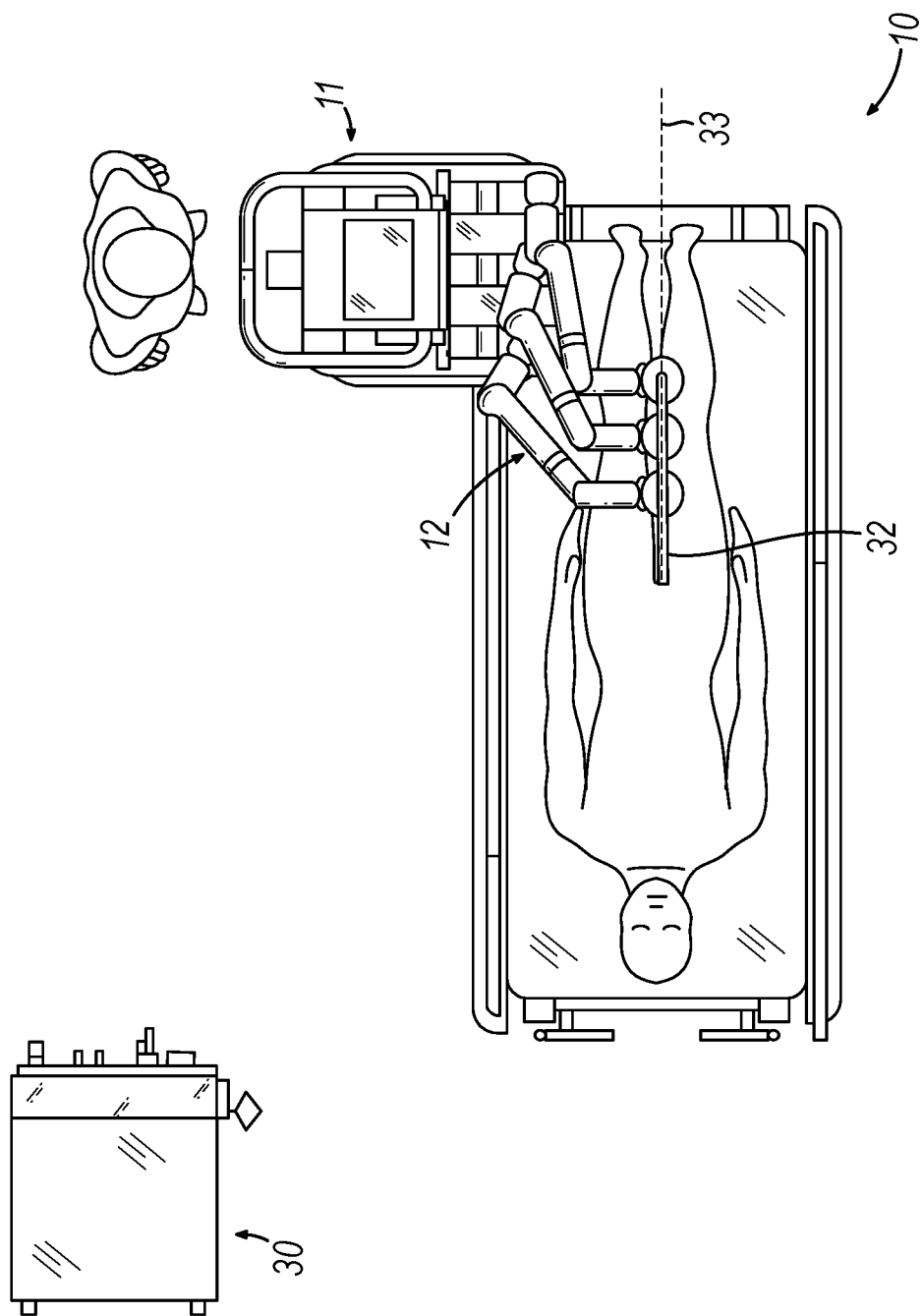
FIG. 3 depicts an embodiment of the robotic system of FIG. 1 arranged for ureteroscopy.

FIG. 3 illustrates an embodiment of a robotically-enabled system (10) arranged for ureteroscopy. In a ureteroscopic procedure, the cart (11) may be positioned to deliver a ureteroscope (32), a procedure-specific endoscope designed to traverse a patient's urethra and ureter, to the lower abdominal area of the patient. In a ureteroscopy, it may be desirable for the ureteroscope (32) to be directly aligned with the patient's urethra to reduce friction and forces on the sensitive anatomy in the area. As shown, the cart (11) may be aligned at the foot of the table to allow the robotic arms (12) to position the ureteroscope (32) for direct linear access to the patient's urethra. From the foot of the table, the robotic arms (12) may insert the ureteroscope (32) along the virtual rail (33) directly into the patient's lower abdomen through the urethra.

After insertion into the urethra, using similar control techniques as in bronchoscopy, the ureteroscope (32) may be navigated into the bladder, ureters, and/or kidneys for diagnostic and/or therapeutic applications. For example, the ureteroscope (32) may be directed into the ureter and kidneys to break up kidney stone build up using a laser or ultrasonic lithotripsy device deployed down the working channel of the ureteroscope (32). After lithotripsy is complete, the resulting stone fragments may be removed using baskets deployed down the ureteroscope (32).

Figure 4:
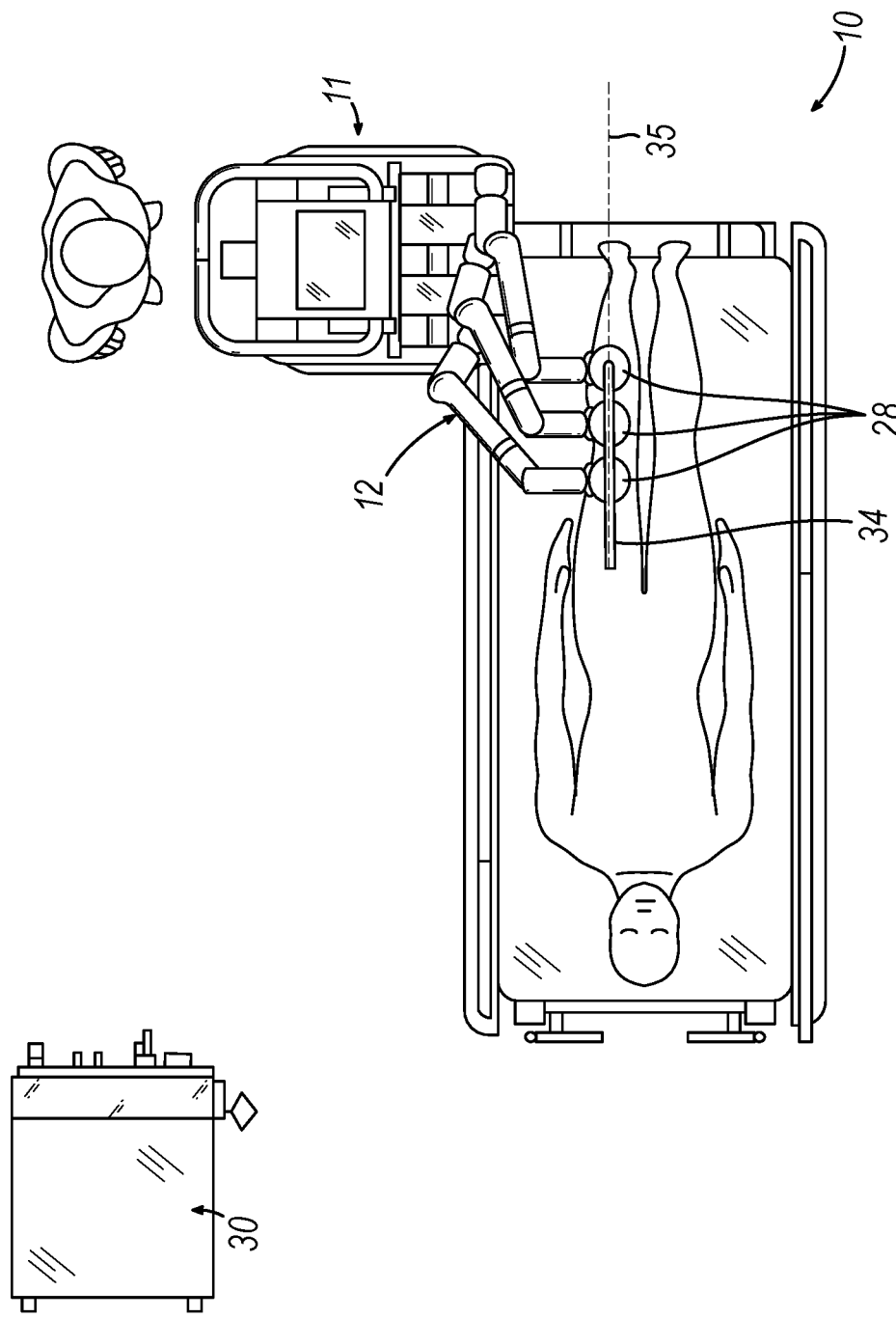
FIG. 4 depicts an embodiment of the robotic system of FIG. 1 arranged for a vascular procedure.

FIG. 4 illustrates an embodiment of a robotically-enabled system similarly arranged for a vascular procedure. In a vascular procedure, the system (10) may be configured such that the cart (11) may deliver a medical instrument (34), such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart (11) may be positioned towards the patient's legs and lower abdomen to allow the robotic arms (12) to provide a virtual rail (35) with direct linear access to the femoral artery access point in the patient's thigh/hip region. After insertion into the artery, the medical instrument (34) may be directed and inserted by translating the instrument drivers (28). Alternatively, the cart may be positioned around the patient's upper abdomen in order to reach alternative vascular access points, such as, for example, the carotid and brachial arteries near the shoulder and wrist.

B. Example of Robotic System Table

Figure 5:
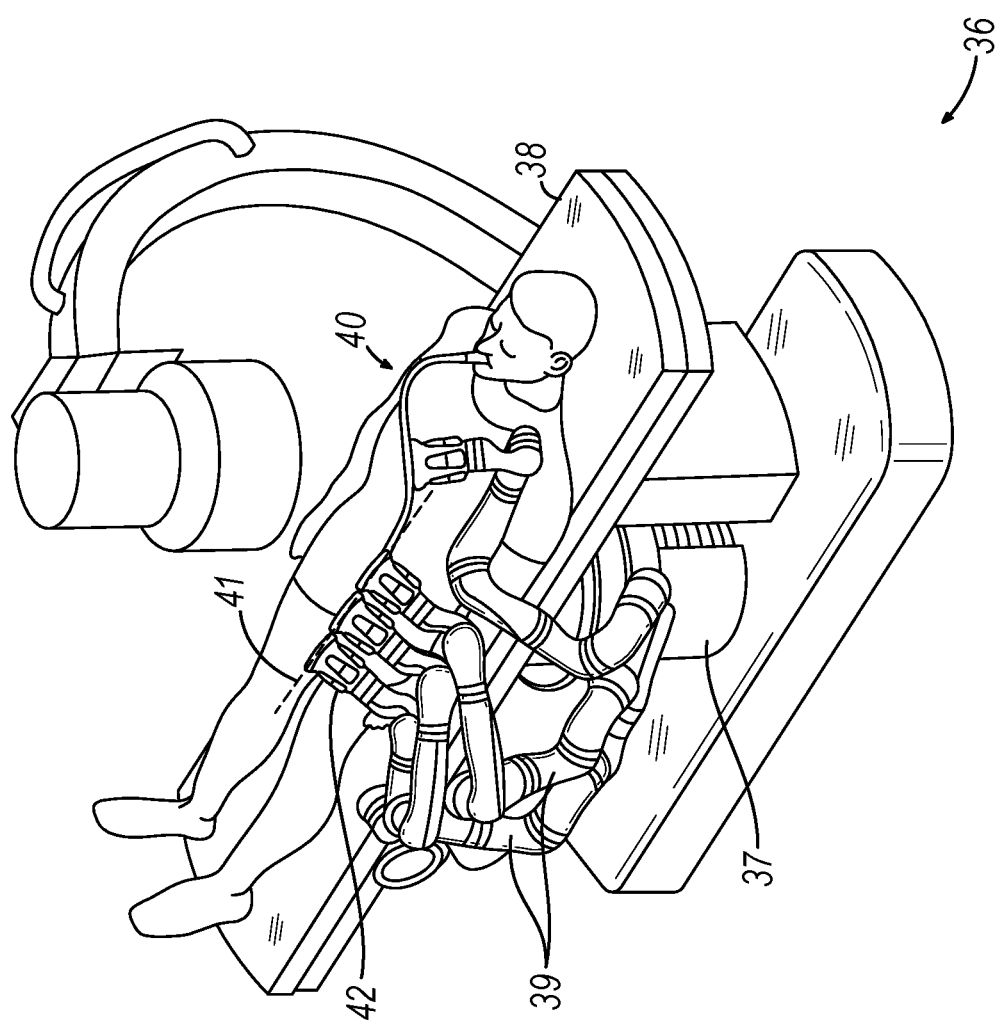
FIG. 5 depicts an embodiment of a table-based robotic system arranged for a bronchoscopy procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopy procedure. System (36) includes a support structure or column (37) for supporting platform (38) (shown as a "table" or "bed") over the floor. Much like in the cart-based systems, the end effectors of the robotic arms (39) of the system (36) comprise instrument drivers (42) that are designed to manipulate an elongated medical instrument, such as a bronchoscope (40) in FIG. 5, through or along a virtual rail (41) formed from the linear alignment of the instrument drivers (42). In practice, a C-arm for providing fluoroscopic imaging may be positioned over the patient's upper abdominal area by placing the emitter and detector around table (38).

Figure 6:
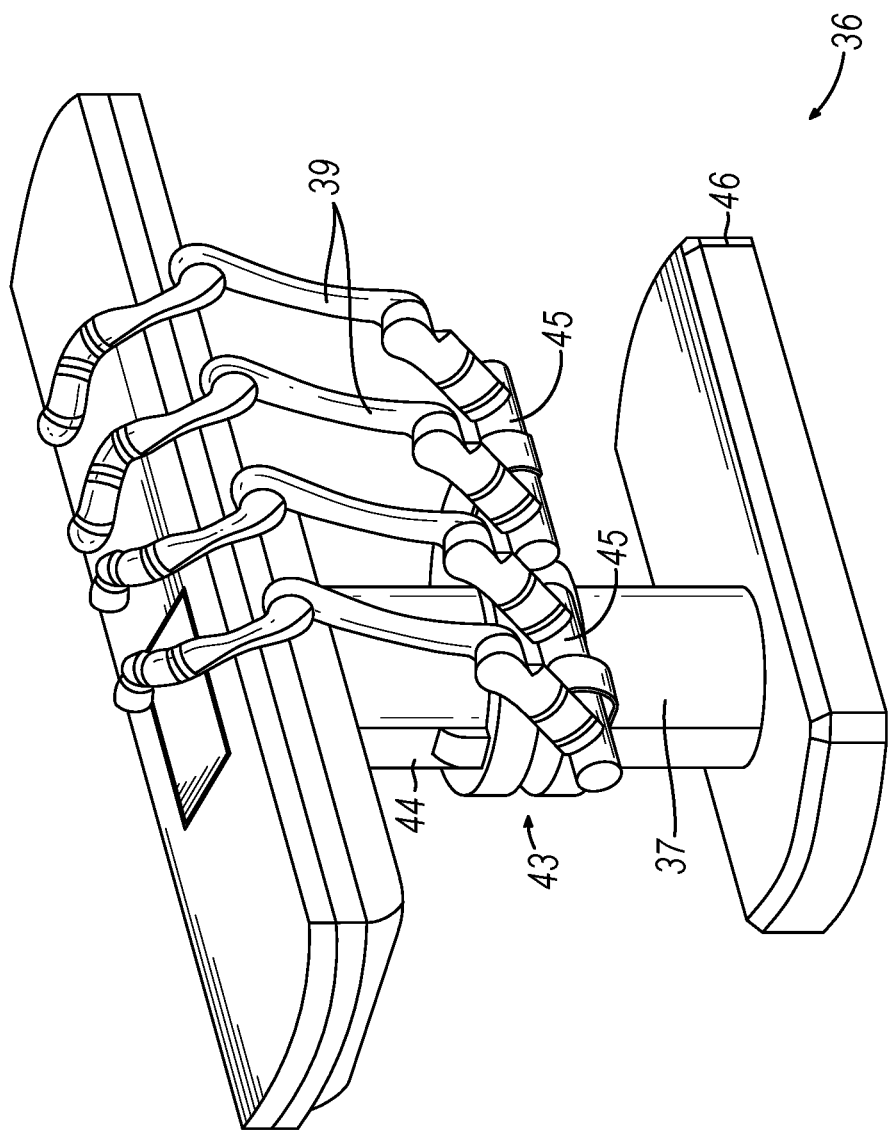
FIG. 6 provides an alternative view of the robotic system of FIG. 5.

FIG. 6 provides an alternative view of the system (36) without the patient and medical instrument for discussion purposes. As shown, the column (37) may include one or more carriages (43) shown as ring-shaped in the system (36), from which the one or more robotic arms (39) may be based. The carriages (43) may translate along a vertical column interface 44 that runs the length of the column (37) to provide different vantage points from which the robotic arms (39) may be positioned to reach the patient. The carriage(s) (43) may rotate around the column (37) using a mechanical motor positioned within the column (37) to allow the robotic arms (39) to have access to multiples sides of the table (38), such as, for example, both sides of the patient. In embodiments with multiple carriages, the carriages may be individually positioned on the column and may translate and/or rotate independent of the other carriages. While carriages (43) need not surround the column (37) or even be circular, the ring-shape as shown facilitates rotation of the carriages (43) around the column (37) while maintaining structural balance. Rotation and translation of the carriages (43) allows the system to align the medical instruments, such as endoscopes and laparoscopes, into different access points on the patient. In other embodiments (not shown), the system (36) can include a patient table or bed with adjustable arm supports in the form of bars or rails extending alongside it. One or more robotic arms (39) (e.g., via a shoulder with an elbow joint) can be attached to the adjustable arm supports, which can be vertically adjusted. By providing vertical adjustment, the robotic arms (39) are advantageously capable of being stowed compactly beneath the patient table or bed, and subsequently raised during a procedure.

Figure 9:
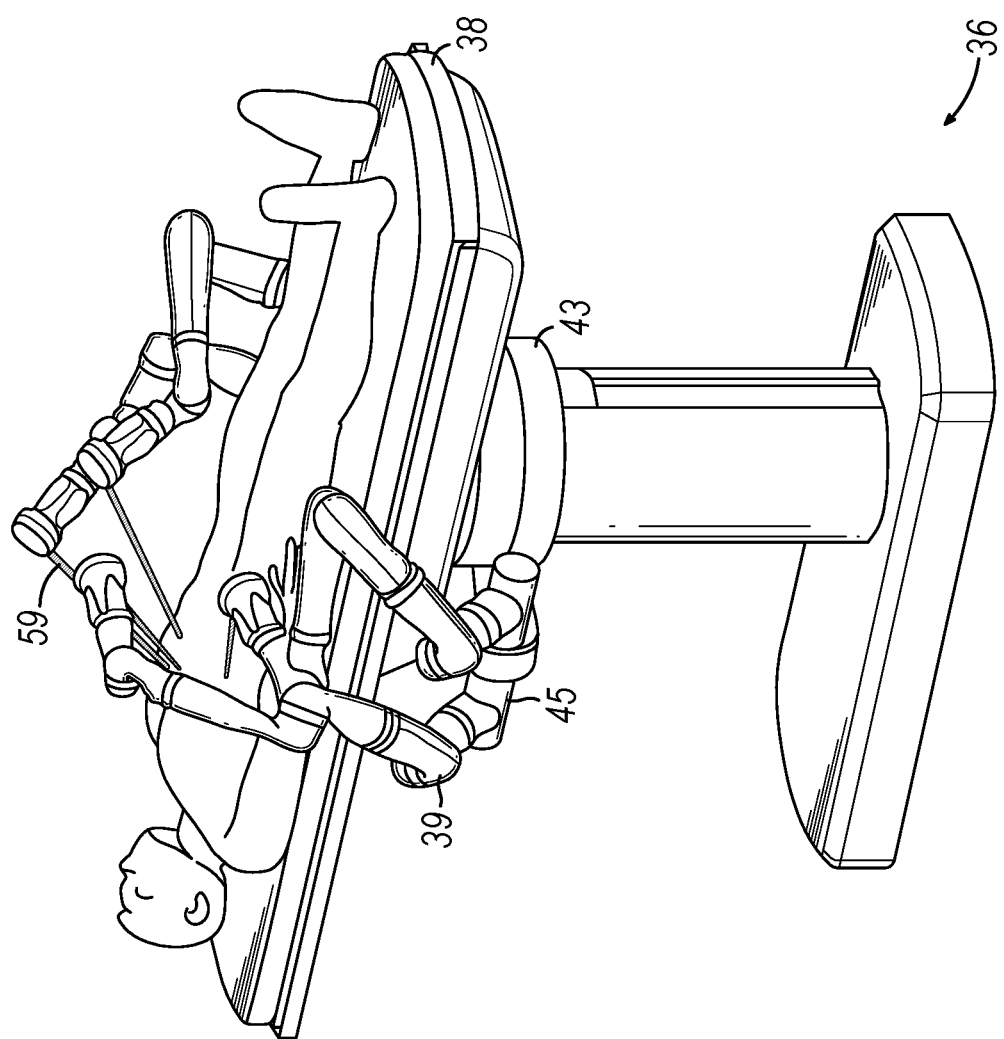
FIG. 9 depicts an embodiment of a table-based robotic system configured for a laparoscopic procedure.

The arms (39) may be mounted on the carriages through a set of arm mounts (45) comprising a series of joints that may individually rotate and/or telescopically extend to provide additional configurability to the robotic arms (39). Additionally, the arm mounts (45) may be positioned on the carriages (43) such that, when the carriages (43) are appropriately rotated, the arm mounts (45) may be positioned on either the same side of table (38) (as shown in FIG. 6), on opposite sides of table (38) (as shown in FIG. 9), or on adjacent sides of the table (38) (not shown).

The column (37) structurally provides support for the table (38), and a path for vertical translation of the carriages. Internally, the column (37) may be equipped with lead screws for guiding vertical translation of the carriages, and motors to mechanize the translation of said carriages based the lead screws. The column (37) may also convey power and control signals to the carriage (43) and robotic arms (39) mounted thereon.

The table base (46) serves a similar function as the cart base (15) in cart (11) shown in FIG. 2, housing heavier components to balance the table/bed (38), the column (37), the carriages (43), and the robotic arms (39). The table base (46) may also incorporate rigid casters to provide stability during procedures. Deployed from the bottom of the table base (46), the casters may extend in opposite directions on both sides of the base (46) and retract when the system (36) needs to be moved.

Continuing with FIG. 6, the system (36) may also include a tower (not shown) that divides the functionality of System (36) between table and tower to reduce the form factor and bulk of the table. As in earlier disclosed embodiments, the tower may provide a variety of support functionalities to table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base for potential stowage of the robotic arms. The tower may also include a master controller or console that provides both a user interface for user input, such as keyboard and/or pendant, as well as a display screen (or touchscreen) for pre-operative and intra-operative information, such as real-time imaging, navigation, and tracking information. In some embodiments, the tower may also contain holders for gas tanks to be used for insufflation.

Figure 7:
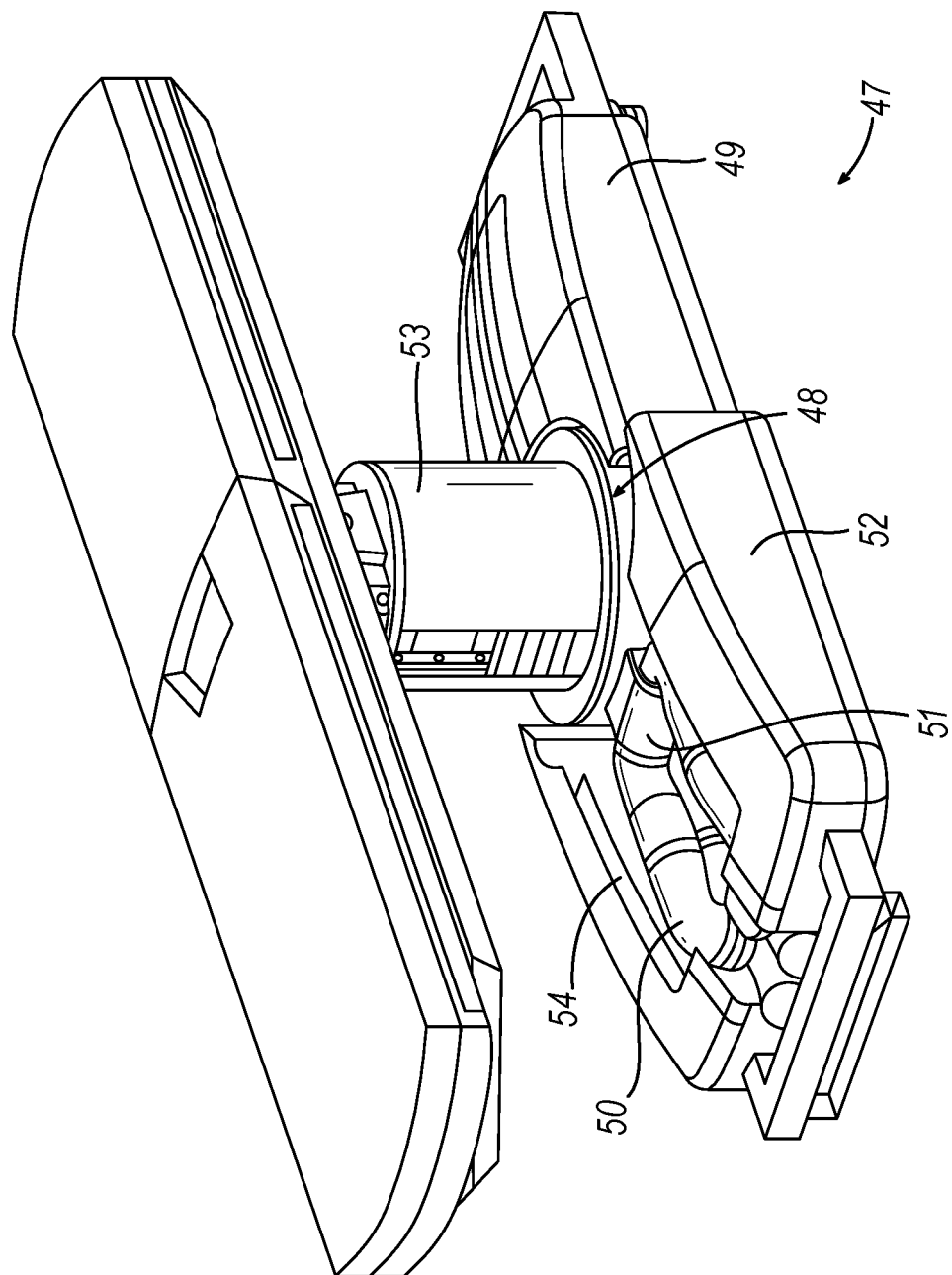
FIG. 7 depicts an example system configured to stow robotic arm(s).

In some embodiments, a table base may stow and store the robotic arms when not in use. FIG. 7 illustrates a system (47) that stows robotic arms in an embodiment of the table-based system. In system (47), carriages (48) may be vertically translated into base (49) to stow robotic arms (50), arm mounts (51), and the carriages (48) within the base (49). Base covers (52) may be translated and retracted open to deploy the carriages (48), arm mounts (51), and arms (50) around column (53), and closed to stow to protect them when not in use. The base covers (52) may be sealed with a membrane (54) along the edges of its opening to prevent dirt and fluid ingress when closed.

Figure 8:
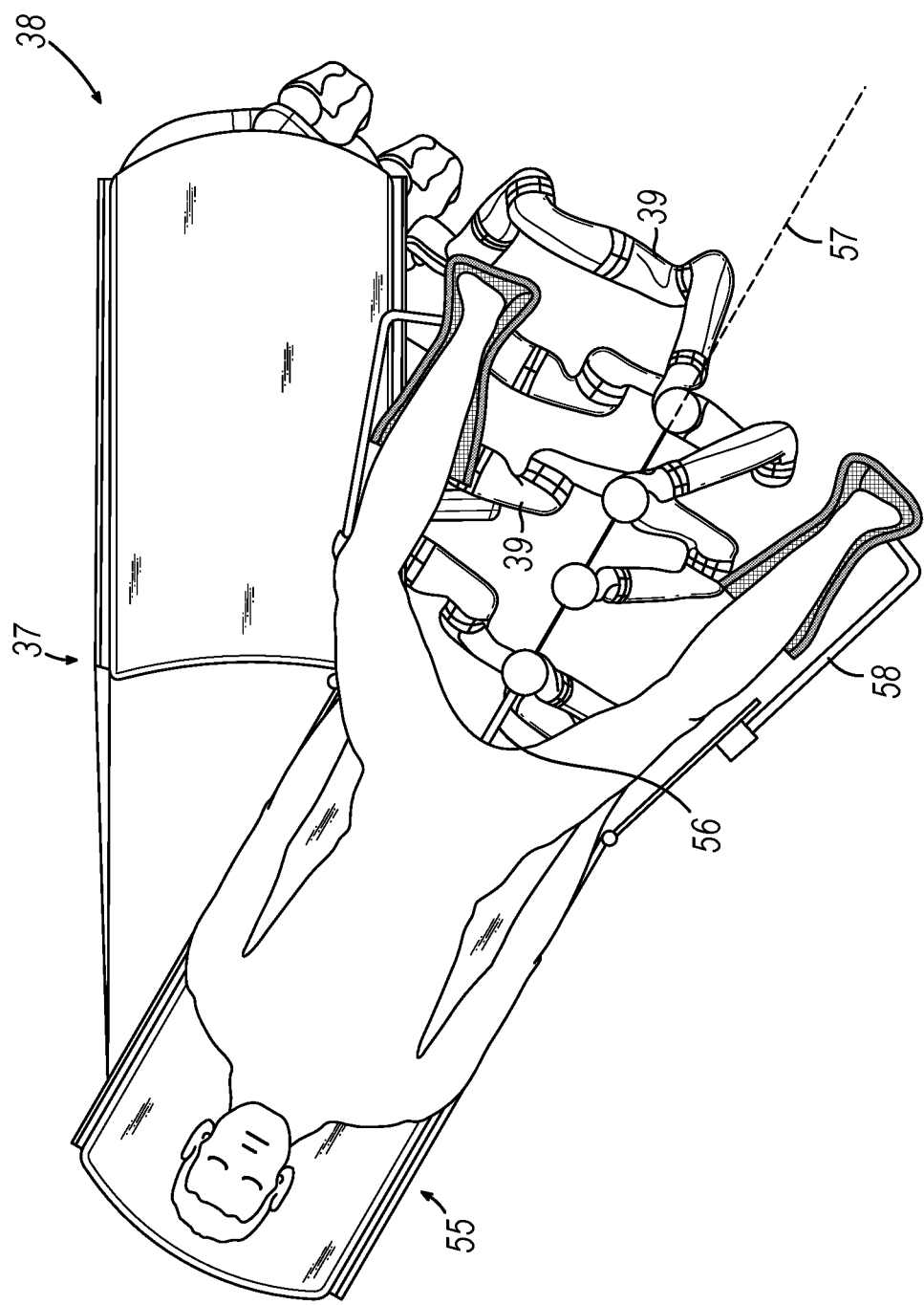
FIG. 8 depicts an embodiment of a table-based robotic system configured for a ureteroscopy procedure.

FIG. 8 illustrates an embodiment of a robotically-enabled table-based system configured for a ureteroscopy procedure. In a ureteroscopy, the table (38) may include a swivel portion (55) for positioning a patient off-angle from the column (37) and table base (46). The swivel portion (55) may rotate or pivot around a pivot point (e.g., located below the patient's head) in order to position the bottom portion of the swivel portion (55) away from the column (37). For example, the pivoting of the swivel portion (55) allows a C-arm (not shown) to be positioned over the patient's lower abdomen without competing for space with the column (not shown) below table (38). By rotating the carriage (35) (not shown) around the column (37), the robotic arms (39) may directly insert a ureteroscope (56) along a virtual rail (57) into the patient's groin area to reach the urethra. In a ureteroscopy, stirrups (58) may also be fixed to the swivel portion (55) of the table (38) to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. FIG. 9 illustrates an embodiment of a robotically-enabled table-based system configured for a laparoscopic procedure. As shown in FIG. 9, the carriages (43) of the system (36) may be rotated and vertically adjusted to position pairs of the robotic arms (39) on opposite sides of the table (38), such that instrument (59) may be positioned using the arm mounts (45) to be passed through minimal incisions on both sides of the patient to reach his/her abdominal cavity.

Figure 10:
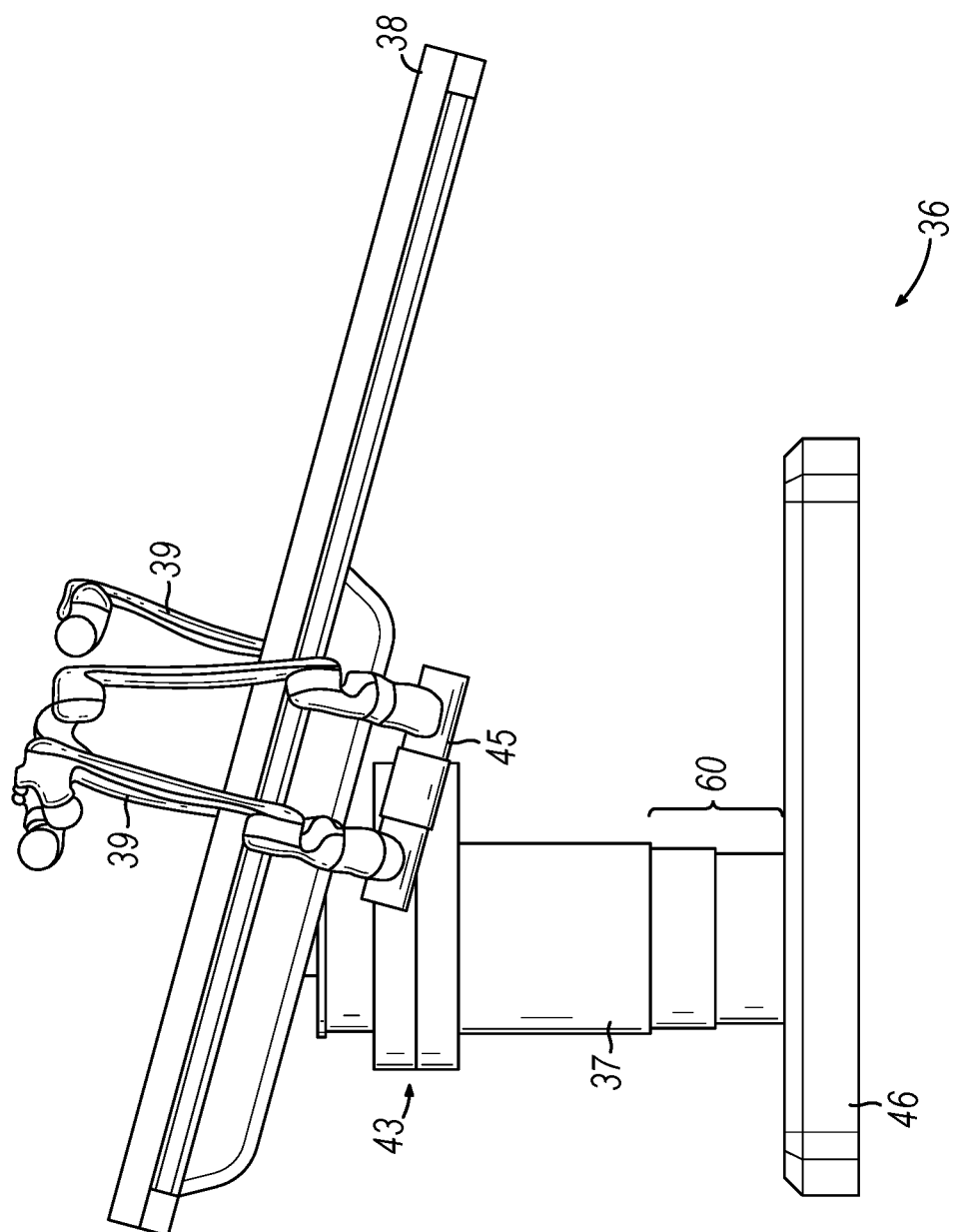
FIG. 10 depicts an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system (36) may accommodate tilt of the table (38) to position one portion of the table at a greater distance from the floor than the other. Additionally, the arm mounts (45) may rotate to match the tilt such that the arms (39) maintain the same planar relationship with table (38). To accommodate steeper angles, the column (37) may also include telescoping portions (60) that allow vertical extension of column (37) to keep the table (38) from touching the floor or colliding with base (46).

Figure 11:
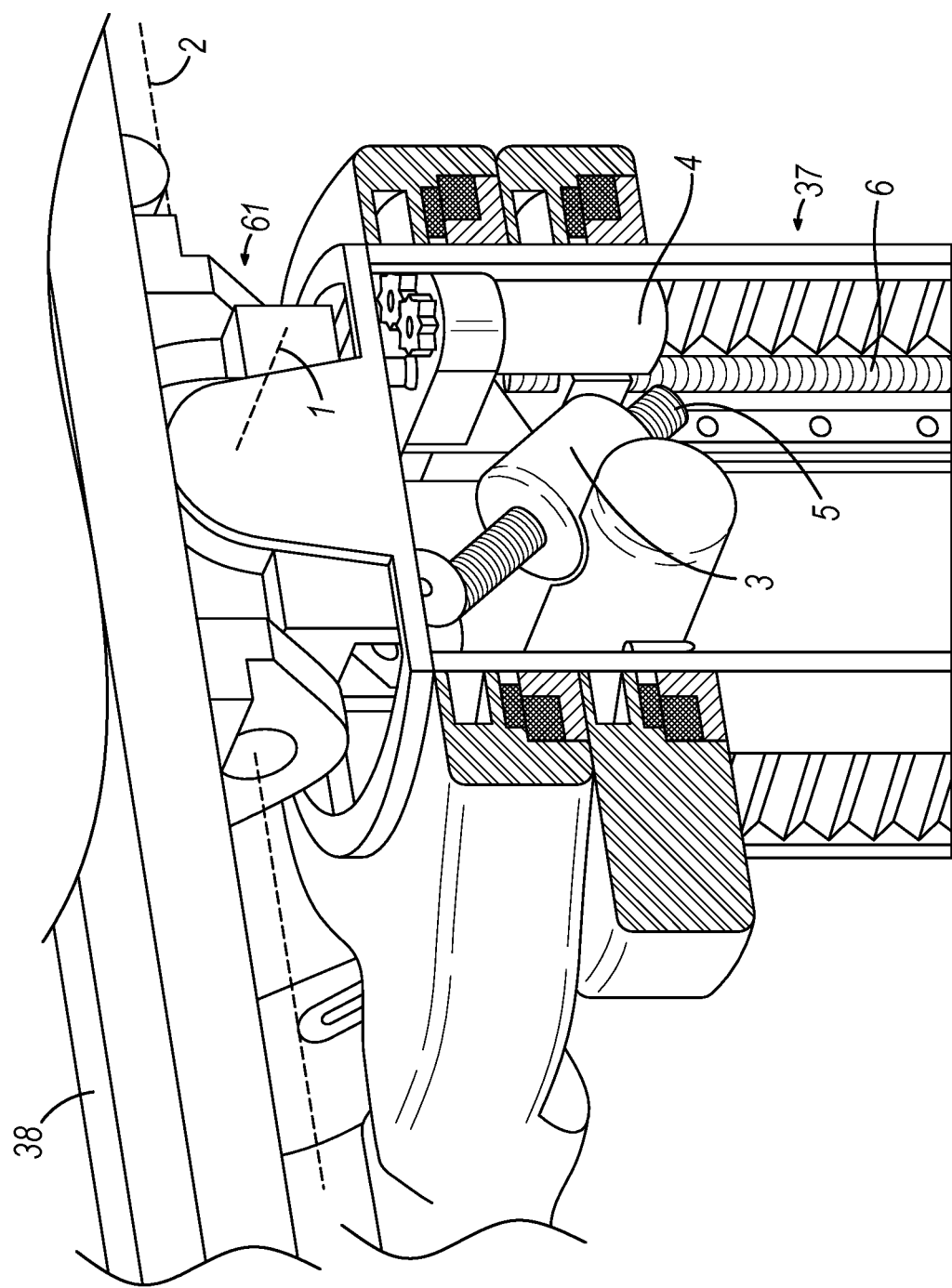
FIG. 11 provides a detailed illustration of the interface between the table and the column of the table-based robotic system of FIGS. 5-10.

FIG. 11 provides a detailed illustration of the interface between the table (38) and the column (37). Pitch rotation mechanism (61) may be configured to alter the pitch angle of the table (38) relative to the column (37) in multiple degrees of freedom. The pitch rotation mechanism (61) may be enabled by the positioning of orthogonal axes (1, 2) at the column-table interface, each axis actuated by a separate motor (3, 4) responsive to an electrical pitch angle command. Rotation along one screw (5) would enable tilt adjustments in one axis (1), while rotation along the other screw (6) would enable tilt adjustments along the other axis (2). In some embodiments, a ball joint can be used to alter the pitch angle of the table (38) relative to the column (37) in multiple degrees of freedom.

For example, pitch adjustments are particularly useful when trying to position the table in a Trendelenburg position, i.e., position the patient's lower abdomen at a higher position from the floor than the patient's lower abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 12:
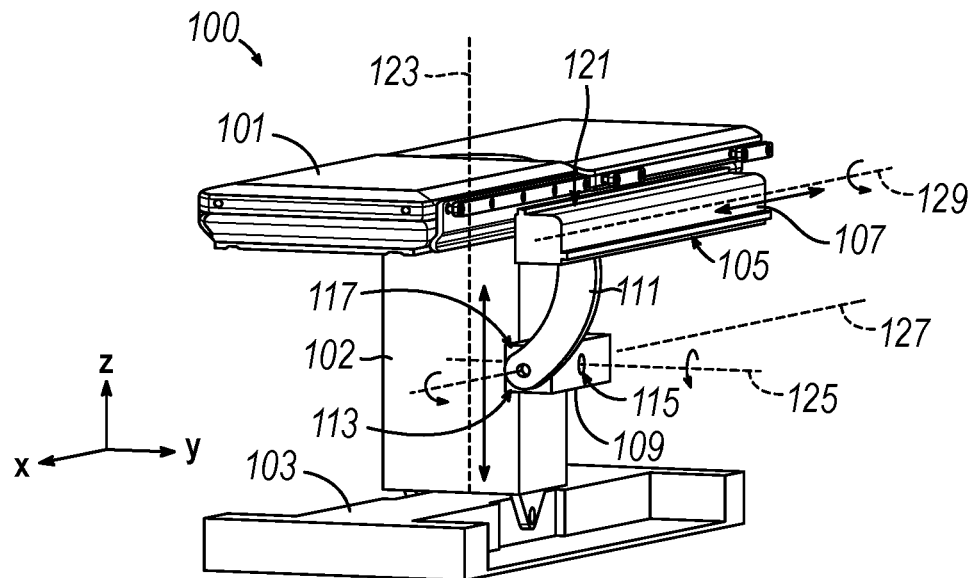
FIG. 12 depicts an alternative embodiment of a table-based robotic system.
Figure 13:
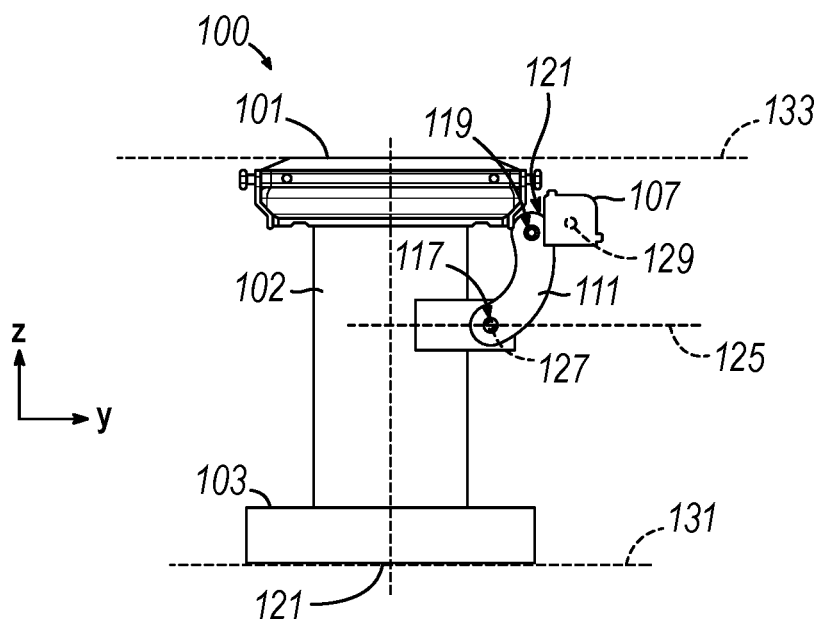
FIG. 13 depicts an end view of the table-based robotic system of FIG. 12.

FIGS. 12 and 13 illustrate isometric and end views of an alternative embodiment of a table-based surgical robotics system (100). The surgical robotics system (100) includes one or more adjustable arm supports (105) that can be configured to support one or more robotic arms (see, for example, FIG. 14) relative to a table (101). In the illustrated embodiment, a single adjustable arm support (105) is shown, though an additional arm support can be provided on an opposite side of the table (101). The adjustable arm support (105) can be configured so that it can move relative to the table (101) to adjust and/or vary the position of the adjustable arm support (105) and/or any robotic arms mounted thereto relative to the table (101). For example, the adjustable arm support (105) may be adjusted one or more degrees of freedom relative to the table (101). The adjustable arm support (105) provides high versatility to the system (100), including the ability to easily stow the one or more adjustable arm supports (105) and any robotics arms attached thereto beneath the table (101). The adjustable arm support (105) can be elevated from the stowed position to a position below an upper surface of the table (101). In other embodiments, the adjustable arm support (105) can be elevated from the stowed position to a position above an upper surface of the table (101).

The adjustable arm support (105) can provide several degrees of freedom, including lift, lateral translation, tilt, etc. In the illustrated embodiment of FIGS. 12 and 13, the arm support (105) is configured with four degrees of freedom, which are illustrated with arrows in FIG. 12. A first degree of freedom allows for adjustment of the adjustable arm support (105) in the z-direction ("Z-lift"). For example, the adjustable arm support (105) can include a carriage (109) configured to move up or down along or relative to a column (102) supporting the table (101). A second degree of freedom can allow the adjustable arm support (105) to tilt. For example, the adjustable arm support (105) can include a rotary joint, which can allow the adjustable arm support (105) to be aligned with the bed in a Trendelenburg position. A third degree of freedom can allow the adjustable arm support (105) to "pivot up," which can be used to adjust a distance between a side of the table (101) and the adjustable arm support (105). A fourth degree of freedom can permit translation of the adjustable arm support (105) along a longitudinal length of the table.

The surgical robotics system (100) in FIGS. 12 and 13 can comprise a table supported by a column (102) that is mounted to a base (103). The base (103) and the column (102) support the table (101) relative to a support surface. A floor axis (131) and a support axis (133) are shown in FIG. 13.

The adjustable arm support (105) can be mounted to the column (102). In other embodiments, the arm support (105) can be mounted to the table (101) or base (103). The adjustable arm support (105) can include a carriage (109), a bar or rail connector (111) and a bar or rail (107). In some embodiments, one or more robotic arms mounted to the rail (107) can translate and move relative to one another.

The carriage (109) can be attached to the column (102) by a first joint (113), which allows the carriage (109) to move relative to the column (102) (e.g., such as up and down a first or vertical axis 123). The first joint (113) can provide the first degree of freedom ("Z-lift") to the adjustable arm support (105). The adjustable arm support (105) can include a second joint 115, which provides the second degree of freedom (tilt) for the adjustable arm support (105). The adjustable arm support (105) can include a third joint (117), which can provide the third degree of freedom ("pivot up") for the adjustable arm support (105). An additional joint (119) (shown in FIG. 13) can be provided that mechanically constrains the third joint (117) to maintain an orientation of the rail (107) as the rail connector (111) is rotated about a third axis (127). The adjustable arm support (105) can include a fourth joint (121), which can provide a fourth degree of freedom (translation) for the adjustable arm support (105) along a fourth axis (129).

Figure 14:
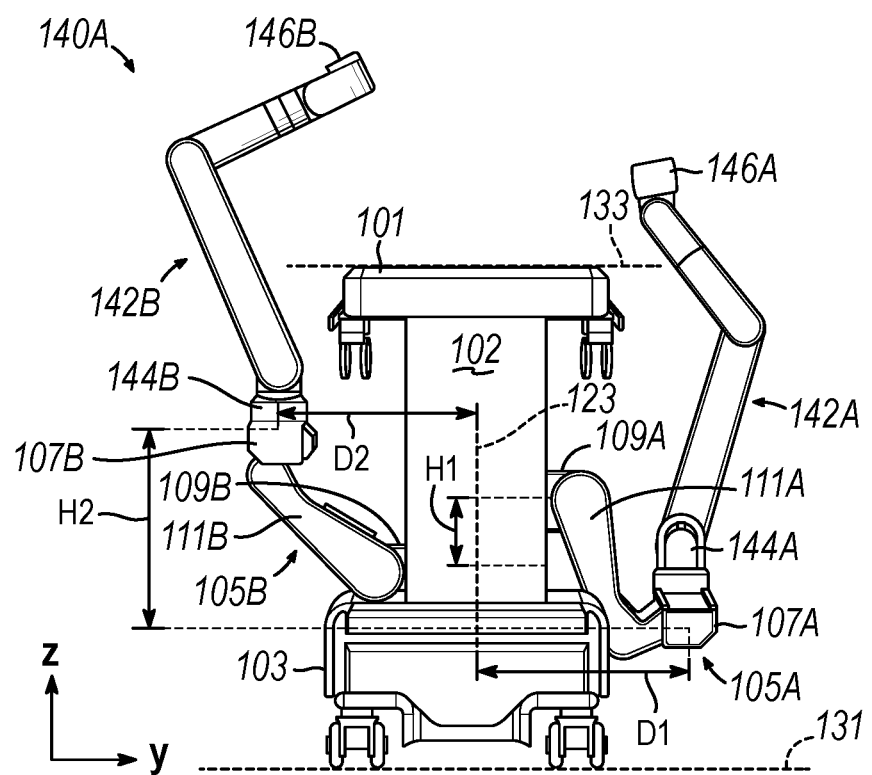
FIG. 14 depicts an end view of a table-based robotic system with robotic arms attached thereto.

FIG. 14 illustrates an end view of the surgical robotics system (140A) with two adjustable arm supports (105A, 105B) mounted on opposite sides of a table (101). A first robotic arm (142A) is attached to the bar or rail (107A) of the first adjustable arm support (105B). The first robotic arm (142A) includes a base (144A) attached to the rail (107A).

The distal end of the first robotic arm (142A) includes an instrument drive mechanism (146A) that can attach to one or more robotic medical instruments or tools. Similarly, the second robotic arm (142B) includes a base (144B) attached to the rail (107B). The distal end of the second robotic arm (142B) includes an instrument drive mechanism (146B). The instrument drive mechanism (146B) can be configured to attach to one or more robotic medical instruments or tools.

In some embodiments, one or more of the robotic arms (142A, 142B) comprises an arm with seven or more degrees of freedom. In some embodiments, one or more of the robotic arms (142A, 142B) can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base (144A, 144B) (1-degree of freedom including translation). In some embodiments, the insertion degree of freedom can be provided by the robotic arm (142A, 142B), while in other embodiments, the instrument itself provides insertion via an instrument-based insertion architecture.

C. Example of Robotic System Instrument Driver & Interface

The end effectors of the system's robotic arms comprise (i) an instrument driver (alternatively referred to as "instrument drive mechanism" or "instrument device manipulator") that incorporate electro-mechanical means for actuating the medical instrument and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 15:
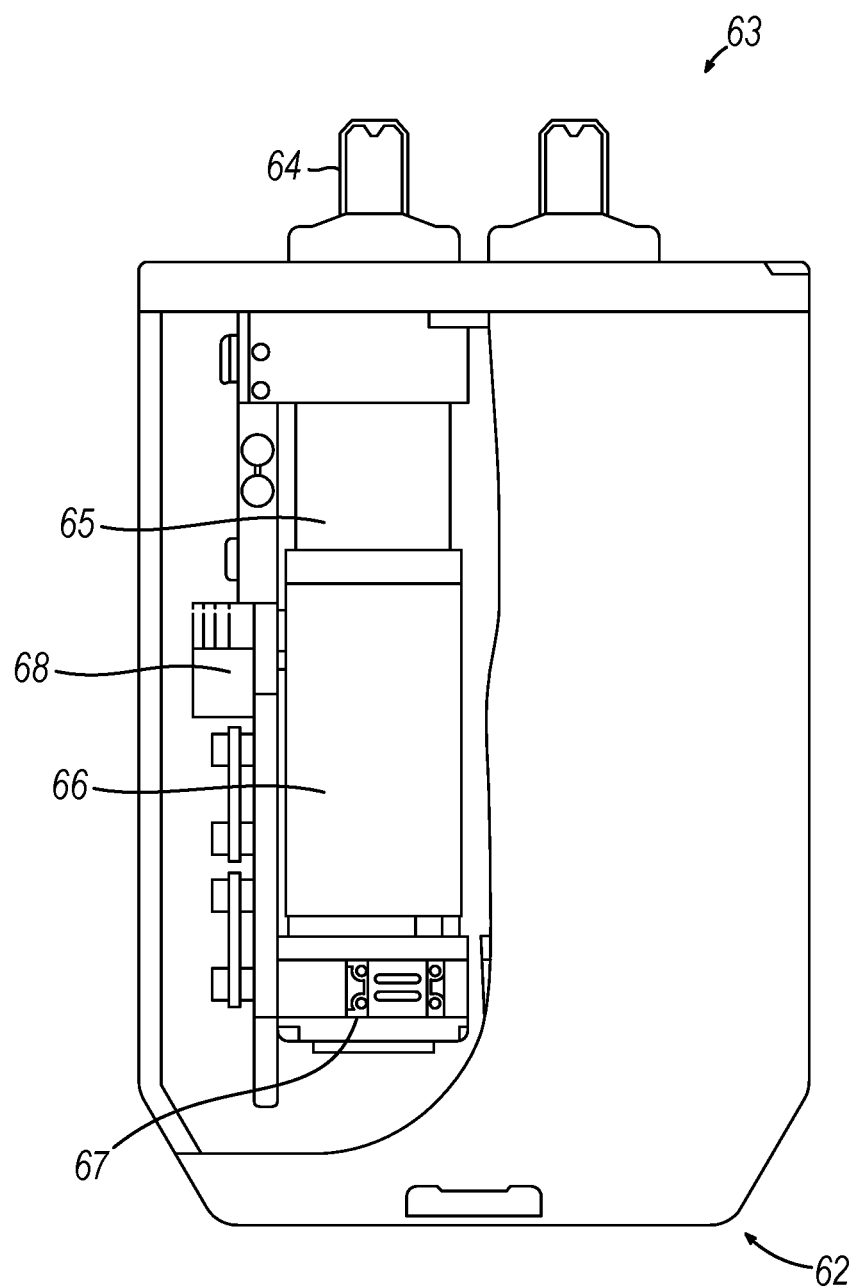
FIG. 15 depicts an exemplary instrument driver.

FIG. 15 illustrates an example instrument driver. Positioned at the distal end of a robotic arm, instrument driver (62) comprises of one or more drive units (63) arranged with parallel axes to provide controlled torque to a medical instrument via drive shafts (64). Each drive unit (63) comprises an individual drive shaft (64) for interacting with the instrument, a gear head (65) for converting the motor shaft rotation to a desired torque, a motor (66) for generating the drive torque, an encoder (67) to measure the speed of the motor shaft and provide feedback to the control circuitry, and control circuitry (68) for receiving control signals and actuating the drive unit. Each drive unit (63) being independent controlled and motorized, the instrument driver (62) may provide multiple (four as shown in FIG. 15) independent drive outputs to the medical instrument. In operation, the control circuitry (68) would receive a control signal, transmit a motor signal to the motor (66), compare the resulting motor speed as measured by the encoder (67) with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise of a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Example of Robotic System Medical Instrument

Figure 16:
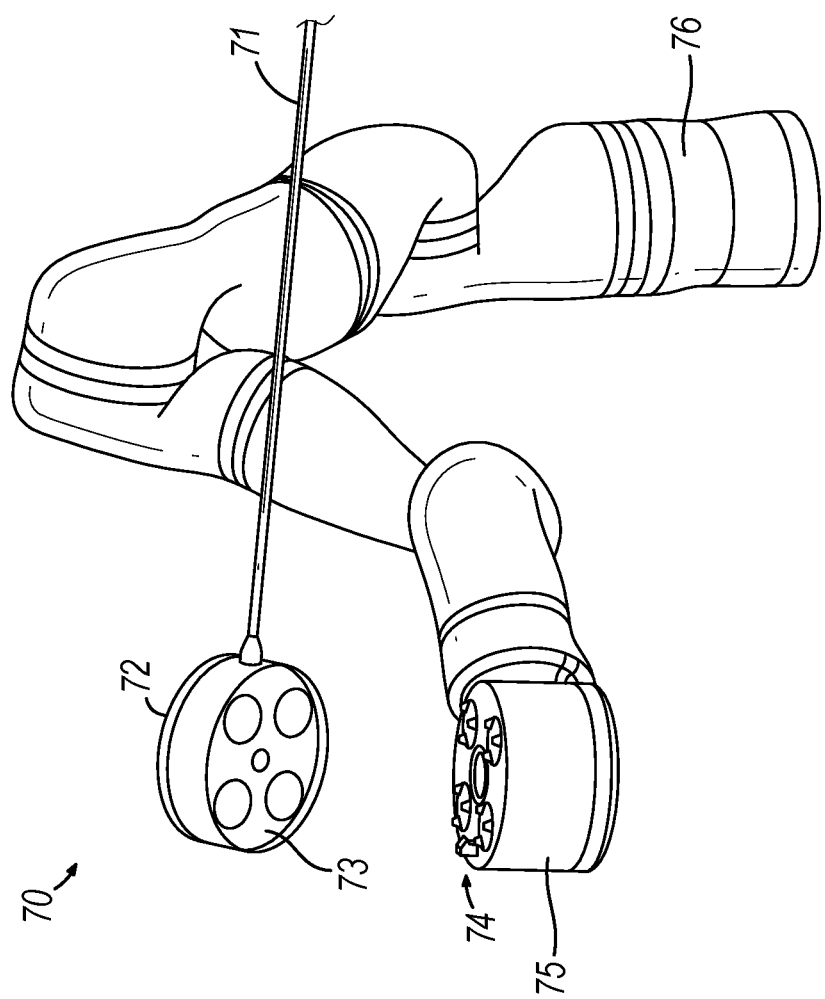
FIG. 16 depicts an exemplary medical instrument with a paired instrument driver.

FIG. 16 illustrates an example medical instrument with a paired instrument driver. Like other instruments designed for use with a robotic system, medical instrument (70) comprises an elongated shaft (71) (or elongate body) and an instrument base (72). The instrument base (72), also referred to as an "instrument handle" due to its intended design for manual interaction by the physician, may generally comprise rotatable drive inputs (73), e.g., receptacles, pulleys or spools, that are designed to be mated with drive outputs (74) that extend through a drive interface on instrument driver (75) at the distal end of robotic arm (76). When physically connected, latched, and/or coupled, the mated drive inputs (73) of instrument base (72) may share axes of rotation with the drive outputs (74) in the instrument driver (75) to allow the transfer of torque from drive outputs (74) to drive inputs (73). In some embodiments, the drive outputs (74) may comprise splines that are designed to mate with receptacles on the drive inputs (73).

The elongated shaft (71) is designed to be delivered through either an anatomical opening or lumen, e.g., as in endoscopy, or a minimally invasive incision, e.g., as in laparoscopy. The elongated shaft (71) may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs (74) of the instrument driver (75). When designed for endoscopy, the distal end of a flexible elongated shaft may include a steerable or controllable bending section that may be articulated and bent based on torque received from the drive outputs (74) of the instrument driver (75).

Torque from the instrument driver (75) is transmitted down the elongated shaft (71) using tendons along the shaft (71). These individual tendons, such as pull wires, may be individually anchored to individual drive inputs (73) within the instrument handle (72). From the handle (72), the tendons are directed down one or more pull lumens along the elongated shaft (71) and anchored at the distal portion of the elongated shaft (71), or in the wrist at the distal portion of the elongated shaft. During a surgical procedure, such as a laparoscopic, endoscopic or hybrid procedure, these tendons may be coupled to a distally mounted end effector, such as a wrist, grasper, or scissor. Under such an arrangement, torque exerted on drive inputs (73) would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at distal end of the elongated shaft (71), where tension from the tendon cause the grasper to close.

In endoscopy, the tendons may be coupled to a bending or articulating section positioned along the elongated shaft (71) (e.g., at the distal end) via adhesive, control ring, or other mechanical fixation. When fixedly attached to the distal end of a bending section, torque exerted on drive inputs (73) would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft (71) to allow for controlled articulation in the desired bending or articulable sections.

In endoscopy, the elongated shaft (71) houses a number of components to assist with the robotic procedure. The shaft may comprise of a working channel for deploying surgical tools (or medical instruments), irrigation, and/or aspiration to the operative region at the distal end of the shaft (71). The shaft (71) may also accommodate wires and/or optical fibers to transfer signals to/from an optical assembly at the distal tip, which may include of an optical camera. The shaft (71) may also accommodate optical fibers to carry light from proximally-located light sources, such as light emitting diodes, to the distal end of the shaft.

At the distal end of the instrument (70), the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 16, the drive shaft axes, and thus the drive input axes, are orthogonal to the axis of the elongated shaft. This arrangement, however, complicates roll capabilities for the elongated shaft (71). Rolling the elongated shaft (71) along its axis while keeping the drive inputs (73) static results in undesirable tangling of the tendons as they extend off the drive inputs (73) and enter pull lumens within the elongated shaft (71). The resulting entanglement of such tendons may disrupt any control algorithms intended to predict movement of the flexible elongated shaft during an endoscopic procedure.

Figure 17:
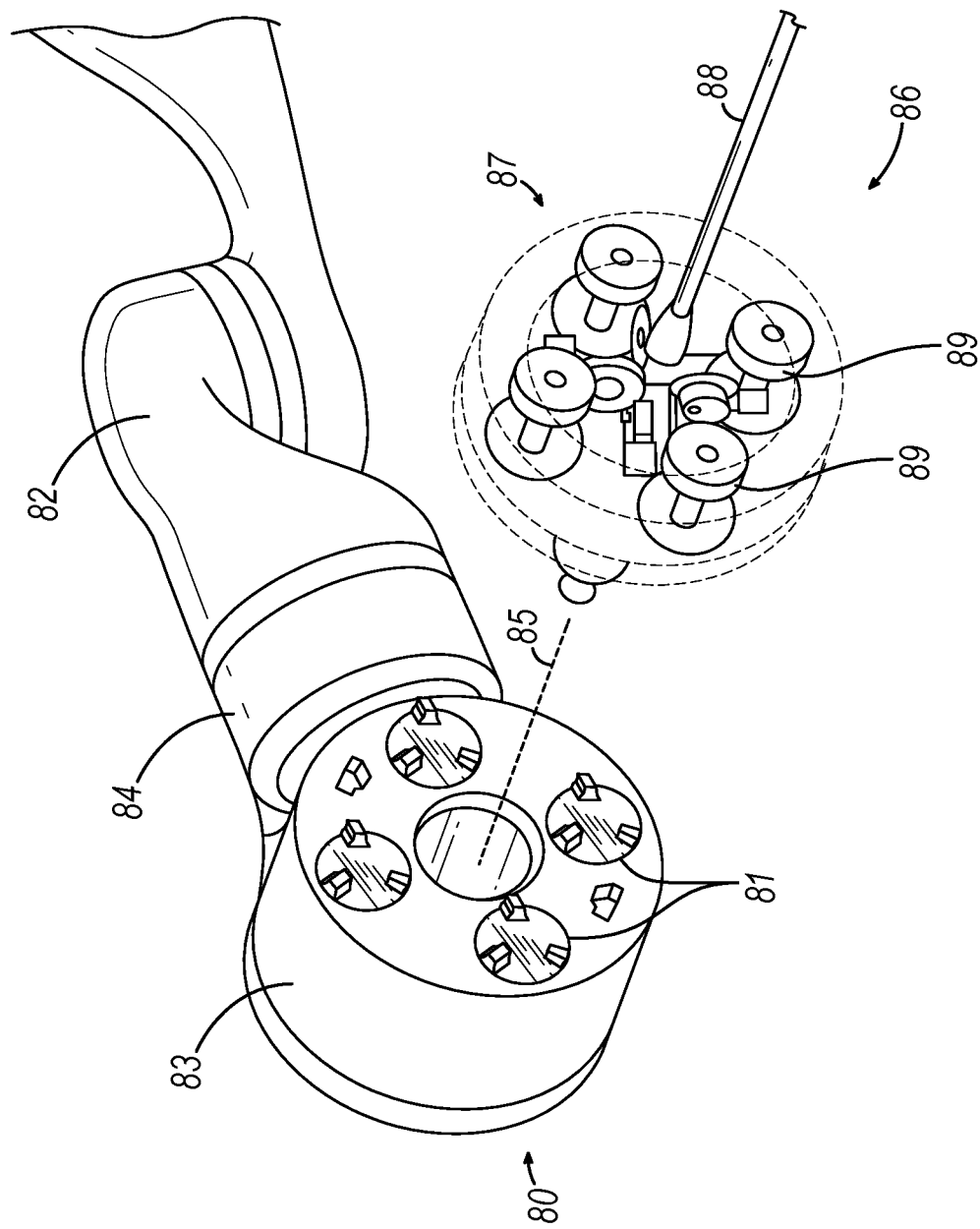
FIG. 17 depicts an alternative design for an instrument driver and instrument where the axes of the drive units are parallel to the axis of the elongated shaft of the instrument.

FIG. 17 illustrates an alternative design for an instrument driver and instrument where the axes of the drive units are parallel to the axis of the elongated shaft of the instrument. As shown, a circular instrument driver (80) comprises four drive units with their drive outputs (81) aligned in parallel at the end of a robotic arm (82). The drive units, and their respective drive outputs (81), are housed in a rotational assembly (83) of the instrument driver (80) that is driven by one of the drive units within the assembly (83). In response to torque provided by the rotational drive unit, the rotational assembly (83) rotates along a circular bearing that connects the rotational assembly (83) to the non-rotational portion (84) of the instrument driver. Power and controls signals may be communicated from the non-rotational portion (84) of the instrument driver (80) to the rotational assembly (83) through electrical contacts may be maintained through rotation by a brushed slip ring connection (not shown). In other embodiments, the rotational assembly (83) may be responsive to a separate drive unit that is integrated into the non-rotatable portion (84), and thus not in parallel to the other drive units. The rotational assembly (83) allows the instrument driver (80) to rotate the drive units, and their respective drive outputs (81), as a single unit around an instrument driver axis (85).

Like earlier disclosed embodiments, an instrument 86 may comprise an elongated shaft portion (88) and an instrument base (87) (shown with a transparent external skin for discussion purposes) comprising a plurality of drive inputs (89) (such as receptacles, pulleys, and spools) that are configured to receive the drive outputs (81) in the instrument driver (80). Unlike prior disclosed embodiments, instrument shaft (88) extends from the center of instrument base (87) with an axis substantially parallel to the axes of the drive inputs (89), rather than orthogonal as in the design of FIG. 16.

When coupled to the rotational assembly (83) of the instrument driver (80), the medical instrument 86, comprising instrument base (87) and instrument shaft (88), rotates in combination with the rotational assembly (83) about the instrument driver axis (85). Since the instrument shaft (88) is positioned at the center of instrument base (87), the instrument shaft (88) is coaxial with instrument driver axis (85) when attached. Thus, rotation of the rotational assembly (83) causes the instrument shaft (88) to rotate about its own longitudinal axis. Moreover, as the instrument base (87) rotates with the instrument shaft (88), any tendons connected to the drive inputs (89) in the instrument base (87) are not tangled during rotation. Accordingly, the parallelism of the axes of the drive outputs (81), drive inputs (89), and instrument shaft (88) allows for the shaft rotation without tangling any control tendons.

Figure 18:
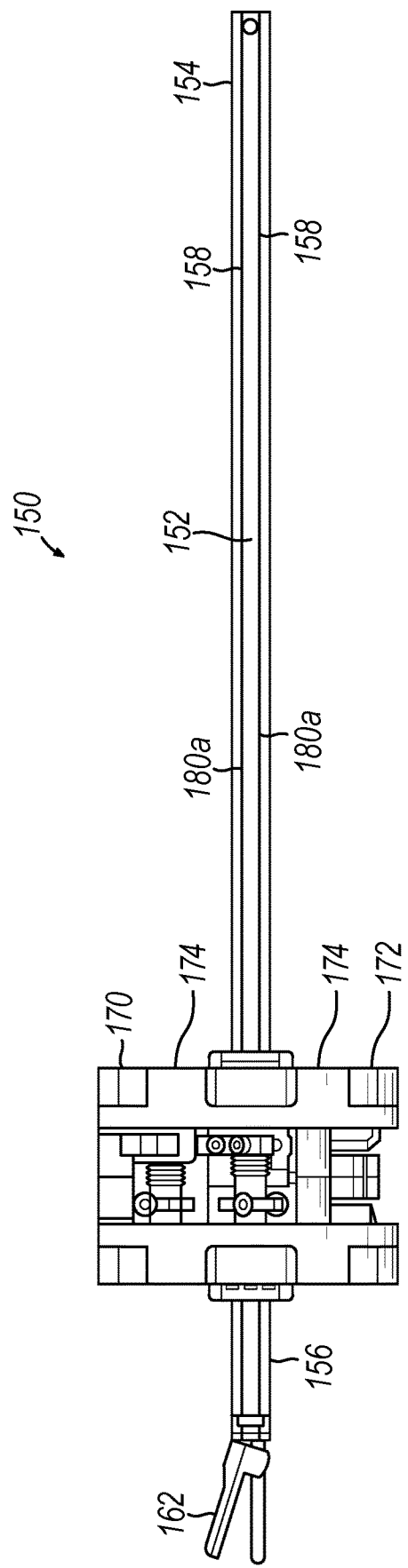
FIG. 18 depicts an instrument having an instrument-based insertion architecture.

FIG. 18 illustrates an instrument having an instrument based insertion architecture in accordance with some embodiments. The instrument (150) can be coupled to any of the instrument drivers discussed above. The instrument (150) comprises an elongated shaft (152), an end effector (162) connected to the shaft (152), and a handle (170) coupled to the shaft (152). The elongated shaft (152) comprises a tubular member having a proximal portion (154) and a distal portion (156). The elongated shaft (152) comprises one or more channels or grooves (158) along its outer surface. The grooves (158) are configured to receive one or more wires or cables (180) therethrough. One or more cables (180) thus run along an outer surface of the elongated shaft (152). In other embodiments, cables (180) can also run through the elongated shaft (152). Manipulation of the one or more cables (180) (e.g., via an instrument driver) results in actuation of the end effector (162).

The instrument handle (170), which may also be referred to as an instrument base, may generally comprise an attachment interface (172) having one or more mechanical inputs (174), e.g., receptacles, pulleys or spools, that are designed to be reciprocally mated with one or more torque couplers on an attachment surface of an instrument driver.

In some embodiments, the instrument (150) comprises a series of pulleys or cables that enable the elongated shaft (152) to translate relative to the handle (170). In other words, the instrument (150) itself comprises an instrument-based insertion architecture that accommodates insertion of the instrument, thereby minimizing the reliance on a robot arm to provide insertion of the instrument (150). In other embodiments, a robotic arm can be largely responsible for instrument insertion.

E. Example of Robotic System Controller

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 19:
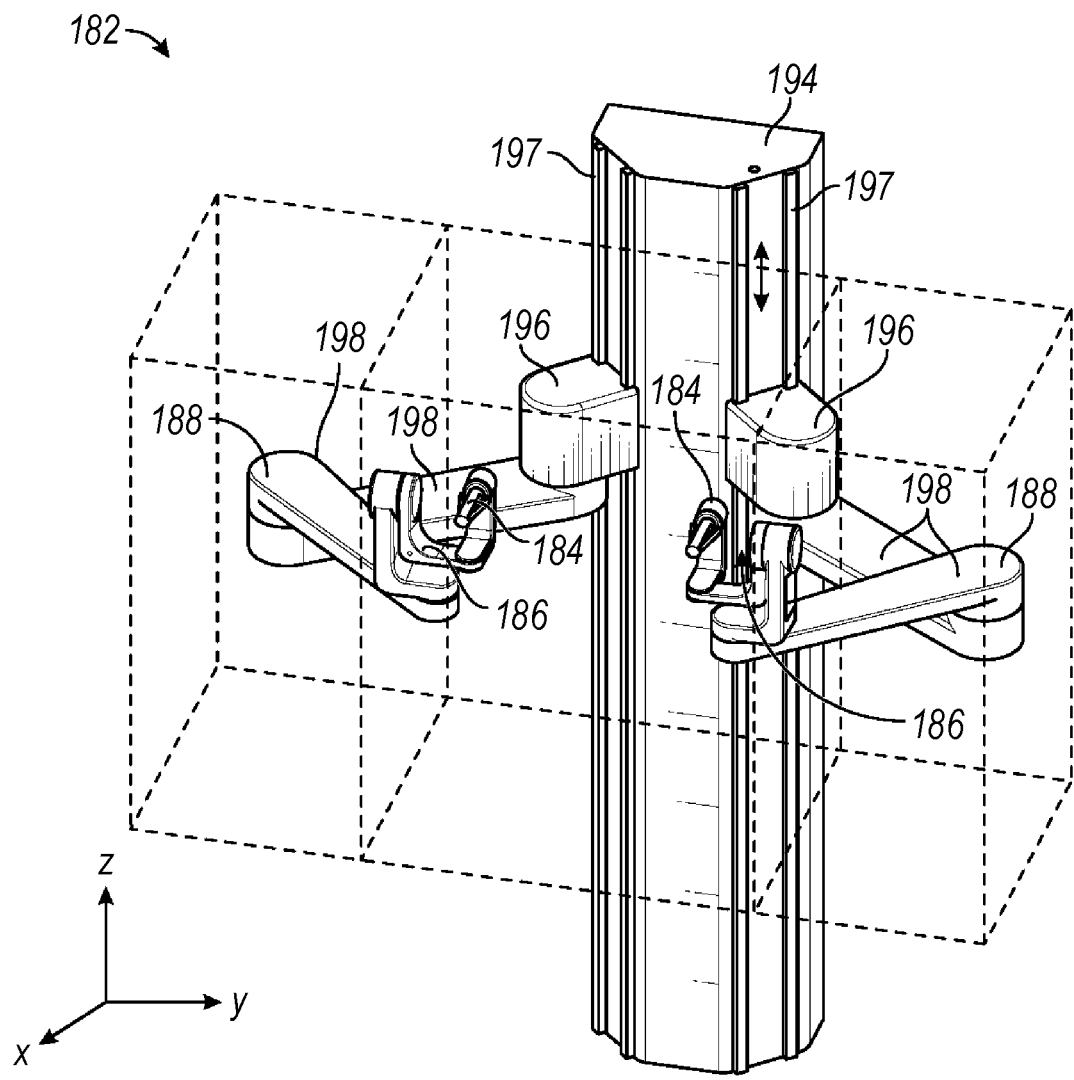
FIG. 19 depicts an exemplary controller.

FIG. 19 is a perspective view of an embodiment of a controller (182). In the present embodiment, the controller (182) comprises a hybrid controller that can have both impedance and admittance control. In other embodiments, the controller (182) can utilize just impedance or passive control. In other embodiments, the controller (182) can utilize just admittance control. By being a hybrid controller, the controller (182) advantageously can have a lower perceived inertia while in use.

In the illustrated embodiment, the controller (182) is configured to allow manipulation of two medical instruments, and includes two handles (184). Each of the handles (184) is connected to a gimbal (186). Each gimbal (186) is connected to a positioning platform (188).

As shown in FIG. 19, each positioning platform (188) includes a SCARA arm (selective compliance assembly robot arm) (198) coupled to a column (194) by a prismatic joint (196). The prismatic joints (196) are configured to translate along the column (194) (e.g., along rails (197)) to allow each of the handles (184) to be translated in the z-direction, providing a first degree of freedom. The SCARA arm (198) is configured to allow motion of the handle (184) in an x-y plane, providing two additional degrees of freedom.

In some embodiments, one or more load cells are positioned in the controller. For example, in some embodiments, a load cell (not shown) is positioned in the body of each of the gimbals (186). By providing a load cell, portions of the controller (182) are capable of operating under admittance control, thereby advantageously reducing the perceived inertia of the controller while in use. In some embodiments, the positioning platform (188) is configured for admittance control, while the gimbal (186) is configured for impedance control. In other embodiments, the gimbal (186) is configured for admittance control, while the positioning platform (188) is configured for impedance control. Accordingly, for some embodiments, the translational or positional degrees of freedom of the positioning platform (188) can rely on admittance control, while the rotational degrees of freedom of the gimbal (186) rely on impedance control.

F. Example of Robotic System Navigation and Control

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 20:
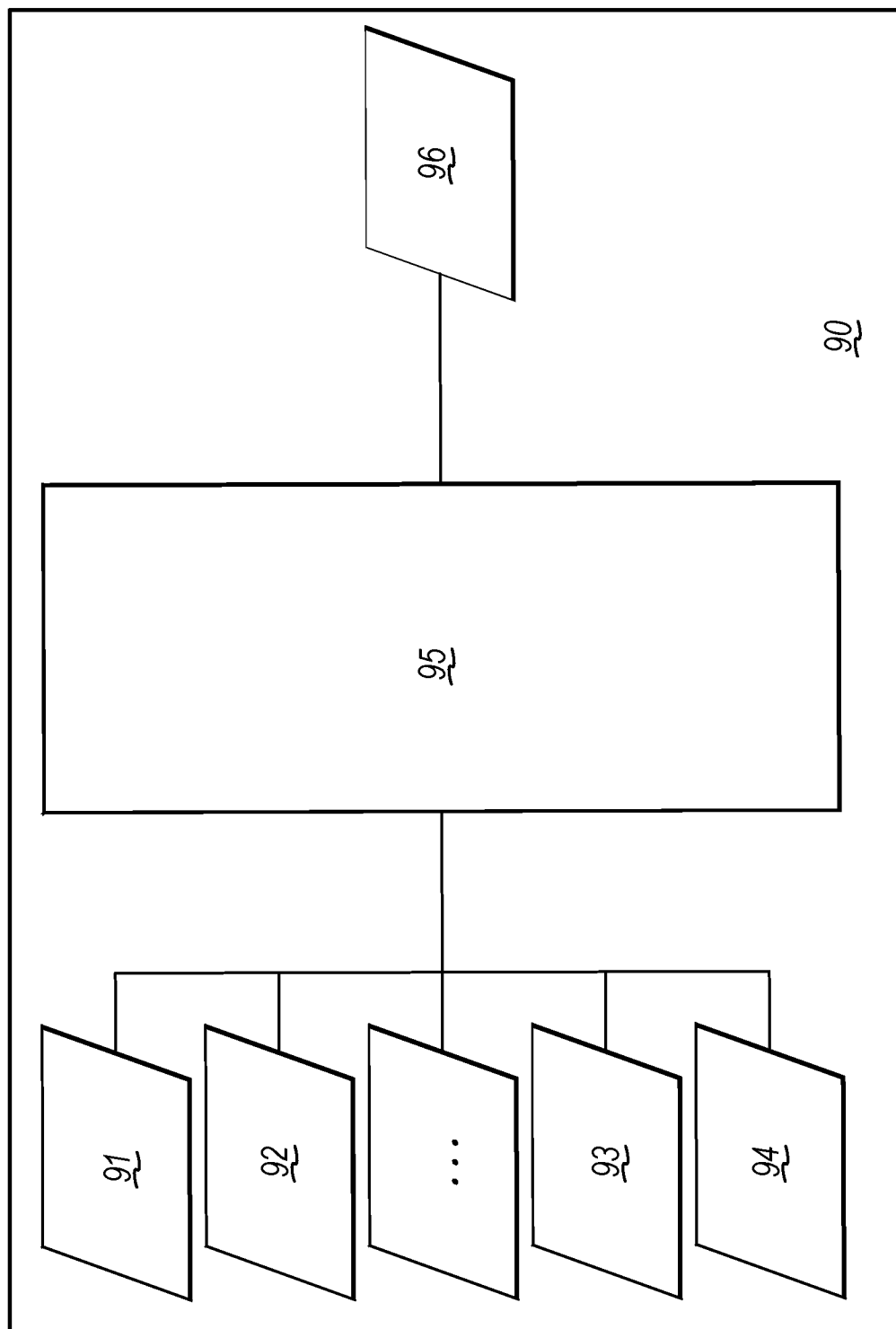
FIG. 20 depicts a block diagram illustrating a localization system that estimates a location of one or more elements of the robotic systems of FIGS. 1-10, such as the location of the instrument of FIGS. 16-18, in accordance to an example embodiment.

FIG. 20 is a block diagram illustrating a localization system (90) that estimates a location of one or more elements of the robotic system, such as the location of the instrument, in accordance to an example embodiment. The localization system (90) may be a set of one or more computer devices configured to execute one or more instructions. The computer devices may be embodied by a processor (or processors) and computer-readable memory in one or more components discussed above. By way of example and not limitation, the computer devices may be in the tower (30) shown in FIG. 1, the cart shown in FIGS. 1-4, the beds shown in FIGS. 5-14, etc.

As shown in FIG. 20, the localization system (90) may include a localization module (95) that processes input data (91-94) to generate location data (96) for the distal tip of a medical instrument. The location data (96) may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data (91-94) are now described in greater detail. Pre-operative mapping may be accomplished through the use of the collection of low dose CT scans. Pre-operative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data (91) (also referred to as "preoperative model data" when generated using only preoperative CT scans). The use of center-line geometry is discussed in U.S. Pat. No. 9,763,741, the contents of which are herein incorporated in its entirety. Network topological models may also be derived from the CT-images, and are particularly appropriate for bronchoscopy.

In some embodiments, the instrument may be equipped with a camera to provide vision data (92). The localization module (95) may process the vision data to enable one or more vision-based location tracking. For example, the preoperative model data may be used in conjunction with the vision data (92) to enable computer vision-based tracking of the medical instrument (e.g., an endoscope or an instrument advance through a working channel of the endoscope). For example, using the preoperative model data (91), the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module (95) may identify circular geometries in the preoperative model data (91) that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data (92) to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module (95) may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data (93). The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data (94) may also be used by the localization module (95) to provide localization data (96) for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 20 shows, a number of other input data can be used by the localization module (95). For example, although not shown in FIG. 20, an instrument utilizing shape-sensing fiber can provide shape data that the localization module (95) can use to determine the location and shape of the instrument.

The localization module (95) may use the input data (91-94) in combination(s). In some cases, such a combination may use a probabilistic approach where the localization module (95) assigns a confidence weight to the location determined from each of the input data (91-94). Thus, where the EM data may not be reliable (as may be the case where there is EM interference) the confidence of the location determined by the EM data (93) can be decrease and the localization module (95) may rely more heavily on the vision data (92) and/or the robotic command and kinematics data (94).

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

II. Example of Robotically Controlled Uterine Manipulator

In some conventional hysterectomy procedures, a first clinician may serve in a role of forming incisions and performing other laparoscopic operations to remove the uterus of a patient, while a second clinician may serve in a role of manipulating the position and orientation uterus of the patient to facilitate the operations being performed by the first clinician. Such team-based procedures may require clear communication between the first clinician and the second clinician, with the first clinician instructing the second clinician on desired positioning and orientation of the uterus, and with the second clinician responding in a timely and accurate fashion. In some scenarios, such communications may break down or otherwise yield undesirable results, such as the second clinician not precisely positioning or orienting the uterus when and where the first clinician wishes. It may therefore be desirable to provide a robotic system that is capable of performing at least part of the role of the second clinician, such that the robotic system may at least partially control the position and orientation of the uterus based on the desire of the first clinician. Examples of how a robotic system may provide uterine manipulation are described in greater detail below. The following examples may be readily incorporated into any of the various robotic systems (10, 36, 47, 100, 140A) described herein; or in any other suitable robotic system.

Figure 21:
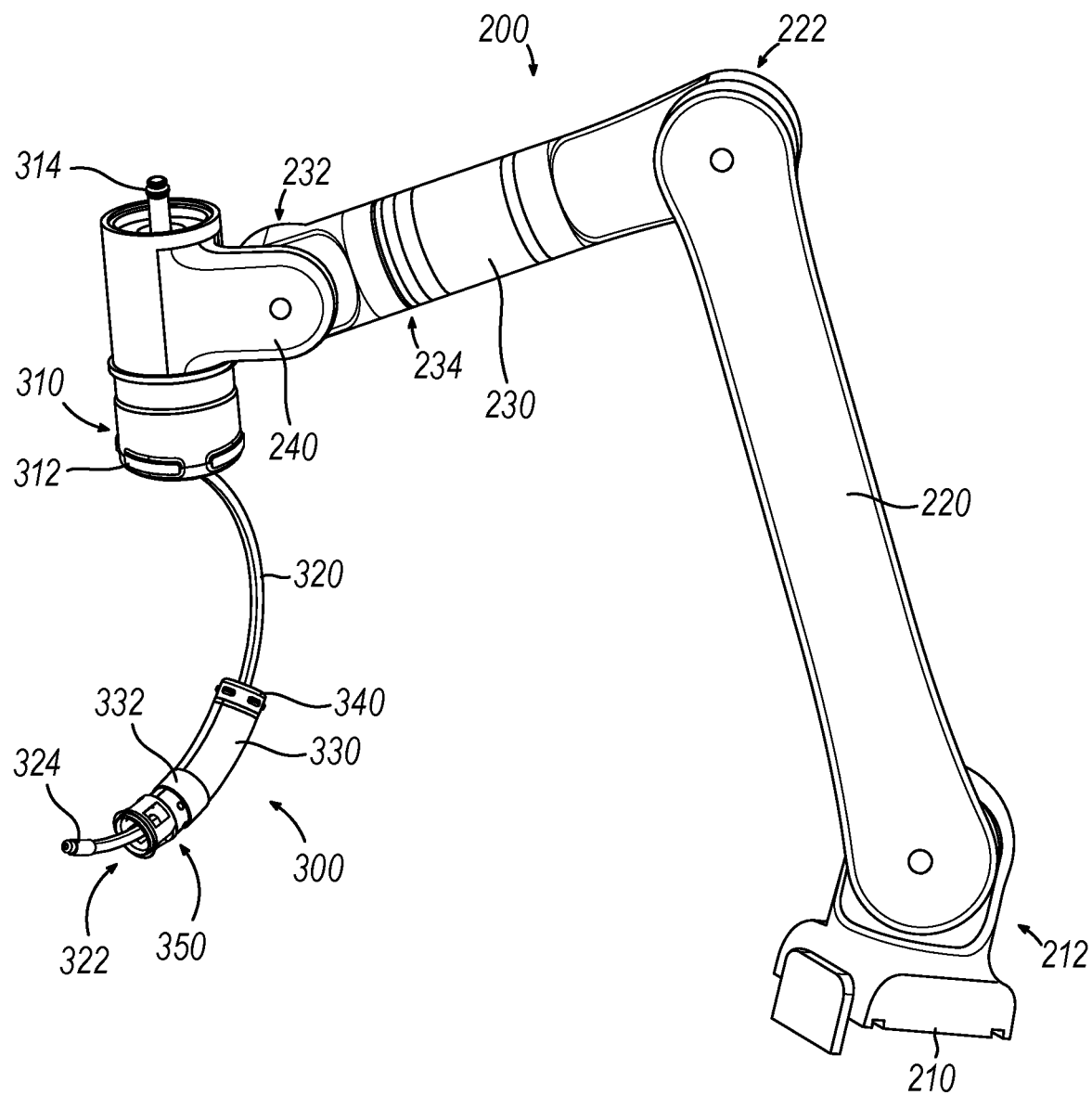
FIG. 21 depicts a perspective view of an example of a robotic arm with a uterine manipulator instrument.

FIG. 21 shows an example of a uterine manipulator (300) secured to a robotic arm (200). Robotic arm (200) of this example includes a mount (210), arm segments (220, 230), a plurality of joints (212, 222, 234, 232), and a head (240). Mount (210) is configured to couple with a component of a robotic system (10, 36, 47, 100, 140A) for support. For instance, mount (210) may be coupled with carriage interface (19), carriage (43), rail (197), or any other suitable structure. In some versions, base (210) is operable to translate along the structure to which base (210) is secured, to thereby assist in positioning robotic arm (200) in relation to a patient and/or to otherwise position robotic arm (200). One end of arm segment (220) is pivotably coupled to base (210) via joint (212), such that arm segment (220) is pivotable relative to base (210) at joint (212). The other end of arm segment (220) is pivotably coupled to an end of arm segment (230) via joint (222), such that arm segment (230) is pivotable relative to arm segment (220) at joint (222). The other end of arm segment (230) is coupled with joint (232) via joint (234). Joint (234) is configured to allow joint (232)

and head (240) to rotate relative to arm segment (230) about the longitudinal axis of arm segment (230). In some variations, a similar kind of joint is provided in arm segment (220), such that arm segment (220) may be effectively broken into two segments where one of those segments is rotatable relative to the other about the longitudinal axes of those two segments. Head (240) is pivotably coupled with joint (234) via joint (232), such that head (240) is pivotable relative to joint (234) at joint (232). Motion at any of joints (212, 222, 234, 232) may be driven robotically via motors, solenoids, and/or any other suitable source(s) of motion.

Figure 22:
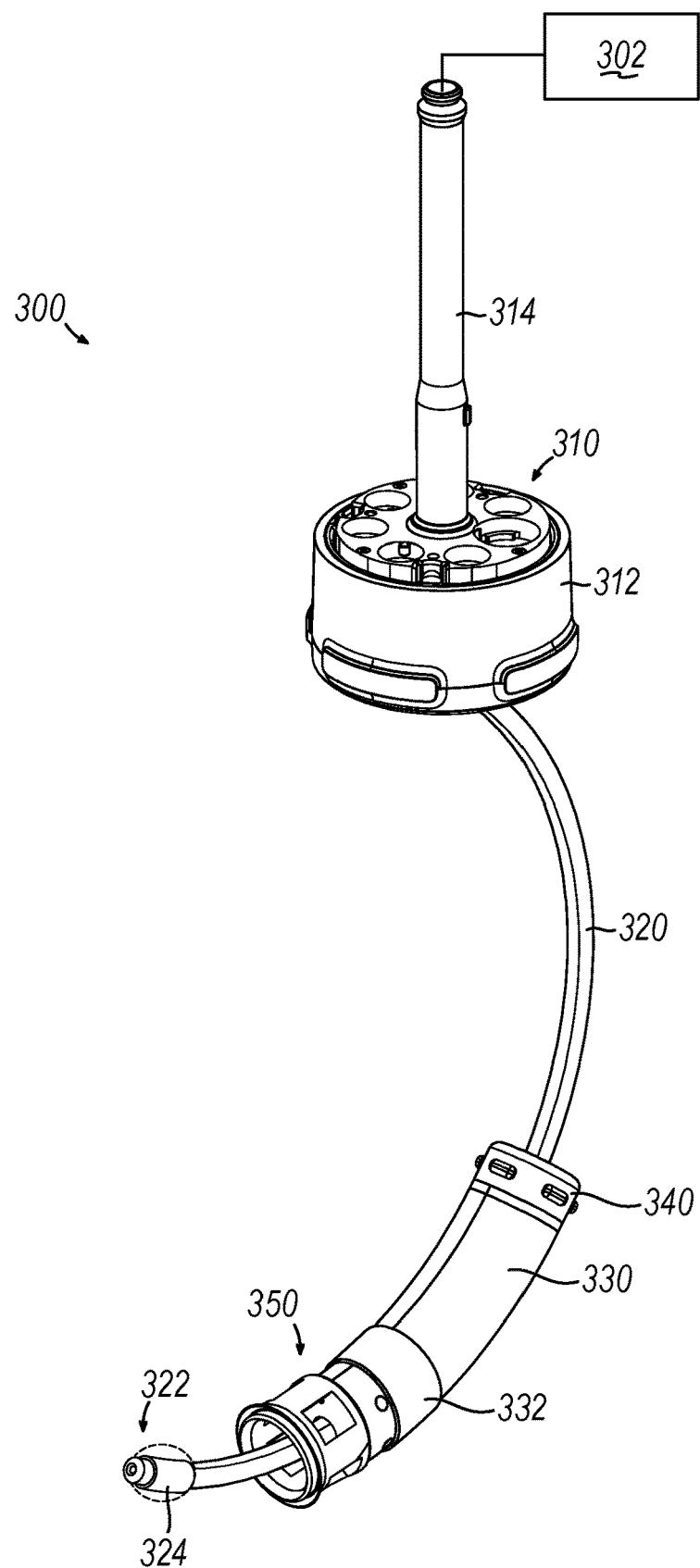
FIG. 22 depicts a perspective view of the uterine manipulator instrument of FIG. 21.

Uterine manipulator (300) is removably coupled with head (240), such that robotic arm (200) may selectively position and orient uterine manipulator in relation to a patient by driving robotic arm (200). As best seen in FIG. 22, uterine manipulator (300) of the present example includes a head interface assembly (310), a shaft (320), a sleeve (330), a sleeve locking ring (340), and a colpotomy cup (350). Head interface assembly (310) includes a base (312) and a shaft (314). Base (312) is configured to removably couple with head (240) to thereby secure uterine manipulator (300) with head (240). By way of example only, base (312) and head (240) may include complementary bayonet fitting features, complementary threading, complementary snap-fit features, and/or any other suitable kinds of structures to provide a removable coupling. Shaft (320) is configured to couple with a pressurized fluid source (302). Pressurized fluid source (302) may contain pressurized air, pressurized saline, or any other suitable kind of pressurized fluid. The pressurized fluid may be used to selectively inflate balloons (324, 332), which will be described in greater detail below.

Shaft (320) of the present example extends distally from base (312) along a curve. In some versions, shaft (320) is rigid. In some other versions, shaft (320) is flexible yet resiliently biased to assume the curved configuration shown. Any suitable biocompatible material(s) may be used to form shaft (320), including but not limited to metallic materials, plastic materials, and combinations thereof. An inflatable balloon (324) is positioned near distal end (322) of shaft (320). Balloon (324) may be formed of an extensible material or a non-extensible material. The interior of shaft (320) includes one or more lumen(s) that are configured to communicate pressurized fluid from pressurized fluid source (302) to balloon (324). While balloon (324) is positioned near distal end (322) of shaft (320) in the present example, other versions may include a different kind of expandable member. By way of example only, an alternative expandable member may include a mechanically expandable component such as an expandable mesh structure, an expanding umbrella-like structure, or any other suitable kind of expandable structure or assembly. In some versions, distal end (322) of shaft (320) may also include an illuminating element (e.g., one or more LEDs, a lens illuminated by one or more optical fibers, etc.). In such versions, one or more wires, optical fibers, and/or other components may extend along the length of shaft (320) to couple with a source of electrical power, a source of light, etc.

Sleeve (330) is slidably coupled to shaft (320), such that sleeve (330) may slide along shaft (320) from a proximal position (FIGS. 25B-25C) to any number of distal positions (FIGS. 21, 22, 25D-25E). Sleeve (330) is generally cylindraceous and rigid; and extends along a curved axis such that the curved lateral profile complements the curved lateral profile of shaft (320). Sleeve (330) may be formed of plastic, metal, and/or any other suitable biocompatible material(s), including combinations of materials. Locking ring (340) is rotatably secured to the proximal end of sleeve (330), while colpotomy cup (350) is fixedly secured to the distal end of sleeve (330). An inflatable balloon (332) is positioned along sleeve (330), between locking ring (340) and colpotomy cup (350). Balloon (332) may be formed of an extensible material or a non-extensible material. The interior of sleeve (330) includes one or more lumen(s) that are configured to communicate pressurized fluid from pressurized fluid source (302) to balloon (332). Such a lumen or lumens may be coupled with pressurized fluid source (302) via a flexible tube (not shown). In some versions, one or more lumens or tubes within shaft (320) provide at least part of the fluid pathway between balloon (332) and pressurized fluid source (302).

Locking ring (340) is operable to selectively secure the position of sleeve (330) along the length of shaft (320). For instance, locking ring (340) may be rotated to a first angular position relative to sleeve (330) to provide an unlocked state where sleeve (330) may be freely translated along shaft (320). Locking ring (340) may then be rotated to a second angular position relative to sleeve (330) to provide a locked state where the position of sleeve (330) along shaft (320) is secured until locking ring (340) is rotated back to the first angular position. By way of example only, locking ring (340) may include one or more frictional braking structures that selectively engage shaft (320) to thereby provide the locked state. Alternatively, locking ring (340) may selectively engage shaft (320) in any other suitable fashion.

Figure 23:
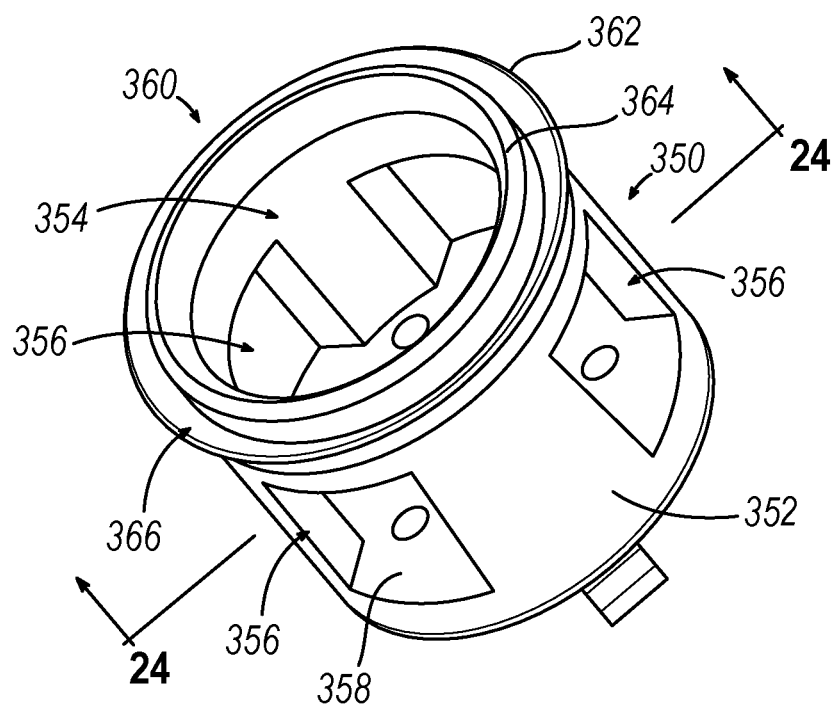
FIG. 23 depicts a perspective view of a colpotomy cup of the uterine manipulator instrument of FIG. 23.
Figure 24:
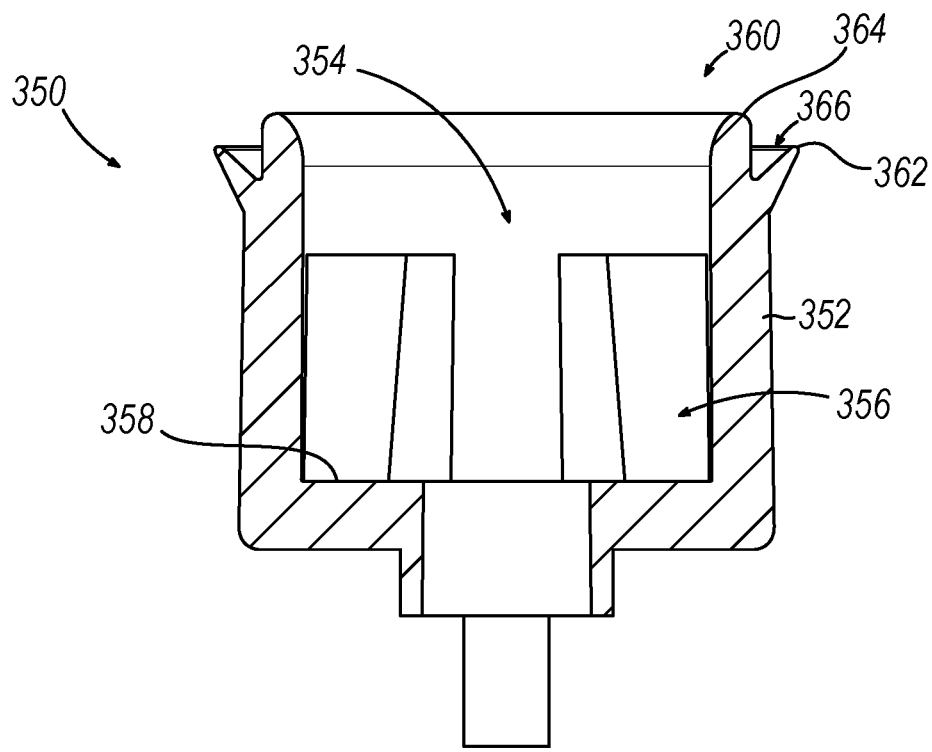
FIG. 24 depicts a cross-sectional side view of the colpotomy cup of FIG. 23.

FIGS. 23-24 show colpotomy cup (350) in greater detail. As shown, colpotomy cup (350) of the present example includes a body (352) defining an interior space (354). Body (352) further includes a floor (358) at the bottom of interior space (354) and an open distal end (360). A plurality of lateral openings (356) are in communication with interior space (354). Distal end (360) includes a distally presented annular edge (364) and an obliquely presented annular edge (362), with a space (366) being defined between edges (362, 364). Space (366) has a V-shaped cross-sectional profile, as best seen in FIG. 24. Colpotomy cup (350) may be formed of plastic, metal, and/or any other suitable biocompatible material(s), including combinations of materials.

Figure 25A:
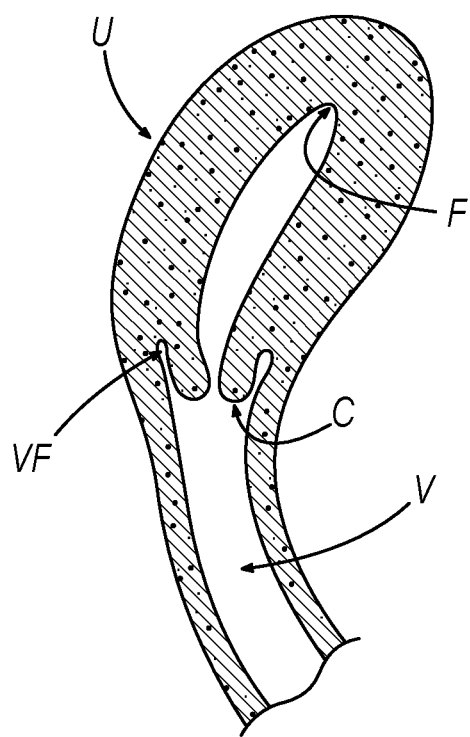
FIG. 25A depicts a mid-sagittal cross-sectional view of a vagina and uterus.
Figure 25B:
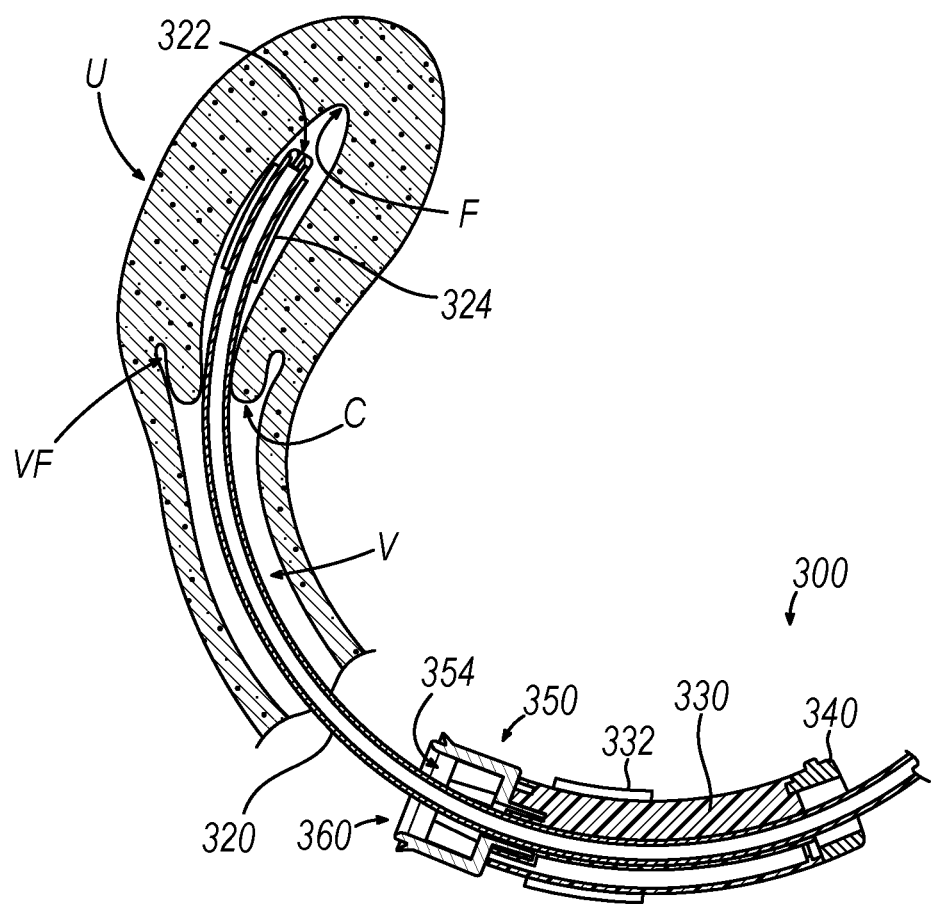
FIG. 25B depicts a mid-sagittal cross-sectional view of the vagina and uterus of FIG. 25A, with the shaft of the uterine manipulator instrument of FIG. 21 inserted through the vagina into the uterus, with a balloon of the uterine manipulator instrument of FIG. 21 in a deflated state, and with a sleeve of the uterine manipulator instrument in a proximal position.

FIGS. 25A-25E show an example of a procedure in which uterine manipulator (300) is used. As shown in FIG. 25A, the anatomical context in which uterine manipulator (300) is used includes a vagina (V) and uterus (U) of a patient. As shown in FIG. 25B, shaft (320) is inserted through the vagina (V) and into the uterus (U) via the cervix (C), while sleeve (330) is in a proximal position along shaft (320). Balloon (324) is in a deflated state during this stage of insertion. In some versions, uterine manipulator (300) is fully decoupled from robotic arm (200) during the process leading up to the stage shown in FIG. 25B, such that uterine manipulator (300) is advanced to this state manually by a human operator grasping a proximal portion of uterine manipulator (300) (e.g., grasping a proximal portion of shaft (320), grasping base (312), and/or grasping some other part of uterine manipulator (300)). In such scenarios, uterine manipulator (300) may be coupled with robotic arm (200) after reaching the stage shown in FIG. 25B.

In some other versions, uterine manipulator (300) is already coupled with robotic arm (200) before reaching the stage shown in FIG. 25B; and robotic arm (200) is used to guide and drive uterine manipulator (300) to the position shown in FIG. 25B. As yet another variation, some versions may allow a human operator to guide and drive uterine manipulator (300) to the position shown in FIG. 25B while uterine manipulator (300) is coupled with robotic arm (200), such that robotic arm (200) does not restrict manual movement of uterine manipulator (300) leading up to the stage shown in FIG. 25B.

Regardless of the stage at which uterine manipulator (300) is coupled with robotic arm (200), robotic arm (200) may be positioned in various suitable ways relative to the patient while uterine manipulator (300) is inserted in the patient. In some scenarios, robotic arm (200) crosses over the top of one of the patient's legs from the side, to assist in positioning uterine manipulator (300). In some other scenarios (e.g., when the patient's legs are supported by stirrups (58)), robotic arm (200) crosses under the bottom of one of the patient's legs from the side, to assist in positioning uterine manipulator (300). In still other scenarios, robotic arm (200) is positioned between the patient's legs from underneath, such that robotic arm (200) does not cross over or under either of the patient's legs. Alternatively, robotic arm (200) may have any other suitable spatial and positional relationship with respect to the patient.

In the present example, uterine manipulator (300) is advanced distally until distal end (322) of shaft (320) reaches the fundus (F) of the uterus (U). The operator may determine that distal end (322) has reached the fundus (F) via tactile feedback (e.g., such that the operator can feel sudden resistance to further advancement of shaft (320)). In addition, or in the alternative, in versions where distal end (322) includes an illuminating element, the illuminating element may provide transillumination through the wall of the uterus (U). Such transillumination may be observed via a laparoscope or other visualization device that is positioned external to the uterus (U). Such transillumination may indicate the extent to which shaft (320) has been inserted into the uterus (U). In some cases where distal end (322) contacts the fundus (F), distal end (322) may remain in contact with fundus (F) throughout the rest of the procedure shown in FIGS. 25B-25E. In some other versions, distal end (322) may be slightly backed out proximally, such that distal end (322) does not contact fundus (F) throughout the rest of the procedure shown in FIGS. 25B-25E.

After reaching the state shown in FIG. 25B, balloon (324) may be inflated as described above; and as shown in FIG. 25C. In some cases, balloon (324) is inflated to a point where balloon (324) bears outwardly against the sidewall of the uterus (U). In any case, the inflated balloon (324) may stabilize the distal portion of shaft (320) relative to the uterus (U). Specifically, the inflated balloon (324) may prevent shaft (320) from exiting proximally from the uterus (U) via the cervix (C). Balloon (324) may thus serve as a distally-positioned anchor structure for uterine manipulator (300). The inflated balloon (324) may also provide sufficient engagement between shaft (320) and the uterus (U) to allow use of shaft (320) to reposition and reorient the uterus (U) as described herein.

Figure 25C:
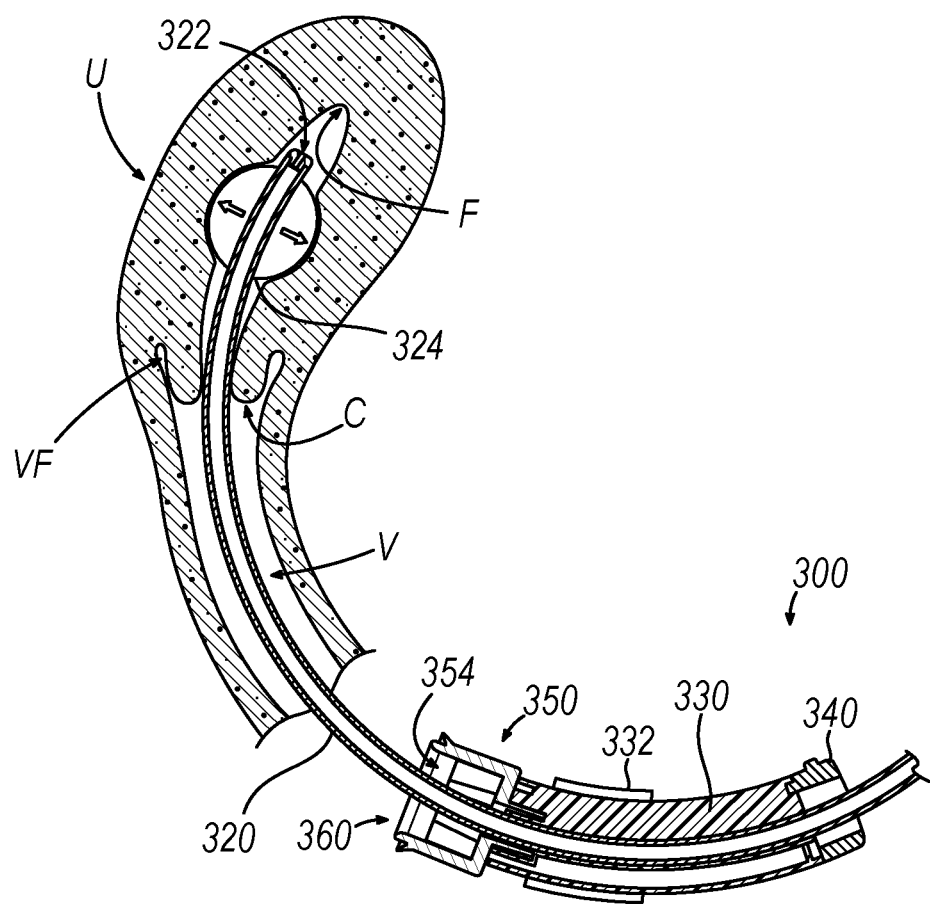
FIG. 25C depicts a mid-sagittal cross-sectional view of the vagina and uterus of FIG. 25A, with the shaft of the uterine manipulator instrument of FIG. 21 inserted through the vagina into the uterus, with the balloon of the uterine manipulator instrument of FIG. 21 in an inflated state, and with the sleeve of the uterine manipulator instrument in the proximal position.
Figure 25D:
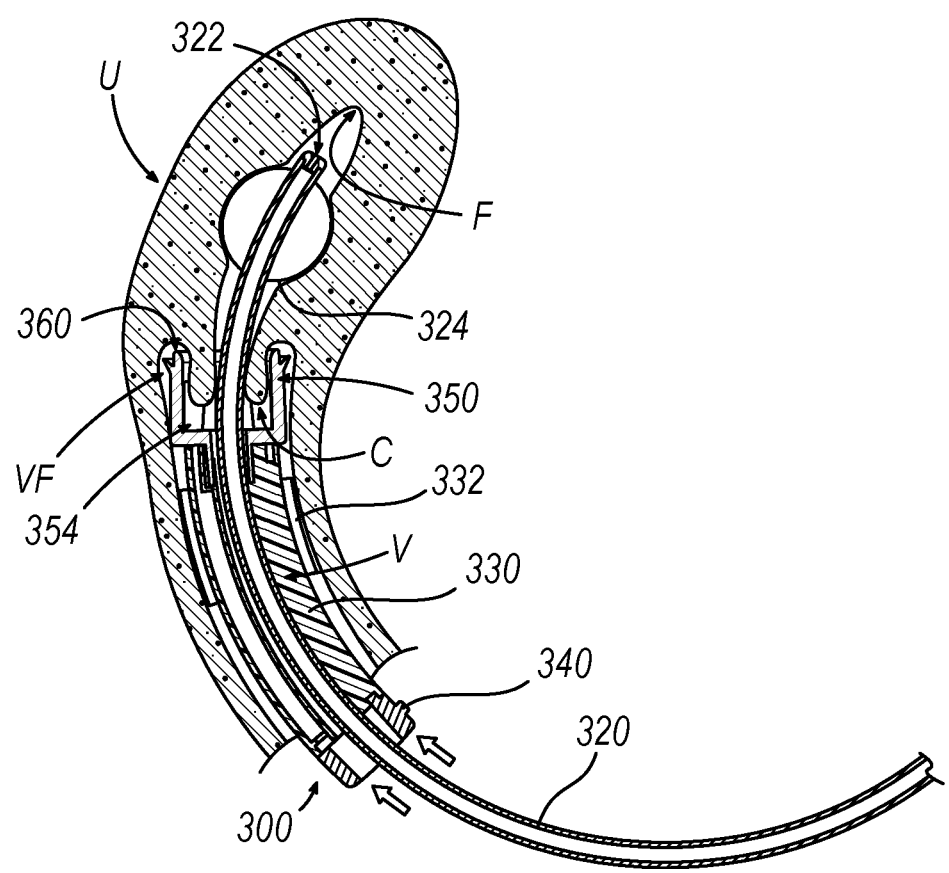
FIG. 25D depicts a mid-sagittal cross-sectional view of the vagina and uterus of FIG. 25A, with the shaft of the uterine manipulator instrument of FIG. 21 inserted through the vagina into the uterus, with the balloon of the uterine manipulator instrument of FIG. 21 in the inflated state, with the sleeve of the uterine manipulator instrument in a distal position such that the colpotomy cup of the sleeve is engaged with the cervix, and with a balloon of the sleeve in a deflated state.

With balloon (324) in the inflated state the operator may advance sleeve (330) distally along shaft (320) to the position shown in FIG. 25D. In the present example, this is performed by a human operator manually advancing sleeve (330) distally along shaft (320). In some other versions, this may be performed by a robotic operator robotically advancing sleeve (330) distally along shaft (320). As shown, sleeve (330) is advanced distally to a point where distal end (360) is firmly seated in the vaginal fornix (VF). The cervix (C) is received in interior space (354) of body (352). At this stage, the longitudinal position of sleeve (330) along shaft (320) is locked in place via locking ring (340). Specifically, the operator grasps locking ring (340) and rotates locking ring (340) about shaft (320) to firmly lock the position of sleeve (330) along shaft (320). In the present example, this is performed by a human operator, though it may be performed by a robotic operator in other versions. With the position of sleeve (330) locked in place against shaft (320), the position of uterine manipulator (300) is substantially fixed relative to the vagina (V), the cervix (C), and the uterus (U). While balloon (324) serves as a distally-positioned anchor structure for uterine manipulator (300), colpotomy cup (350) serves as a proximally-positioned anchor structure for uterine manipulator (300).

Figure 25E:
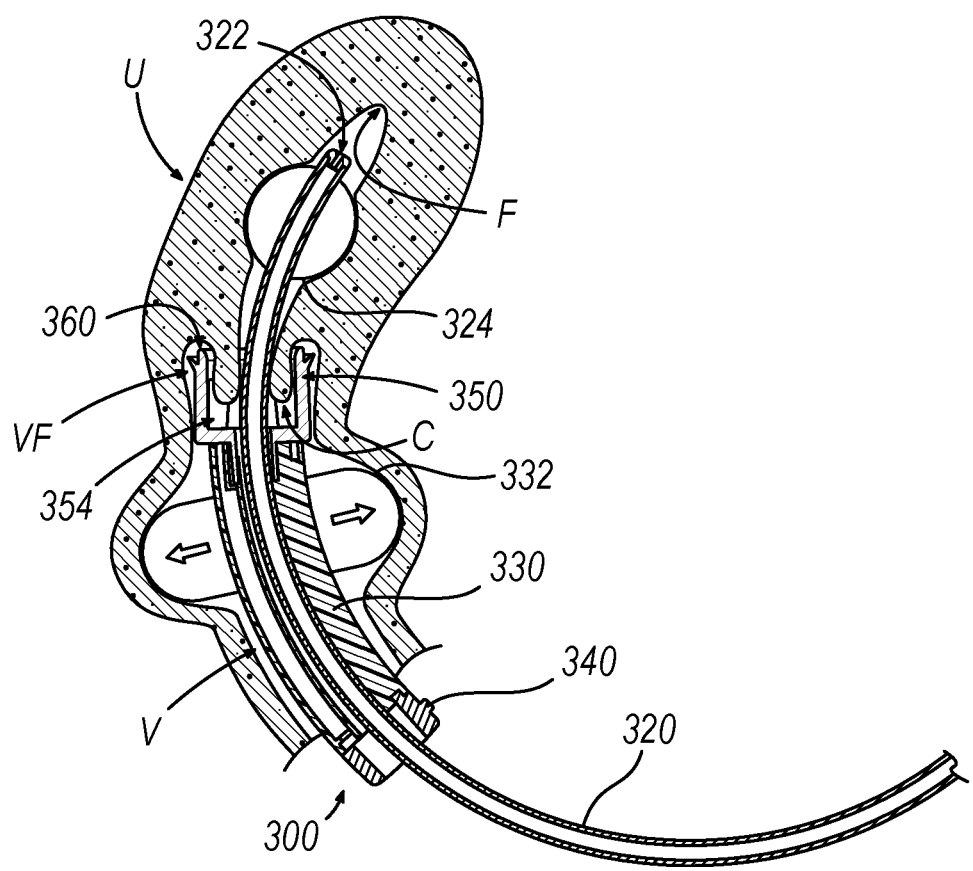
FIG. 25E depicts a mid-sagittal cross-sectional view of the vagina and uterus of FIG. 25A, with the shaft of the uterine manipulator instrument of FIG. 21 inserted through the vagina into the uterus, with the balloon of the uterine manipulator instrument of FIG. 21 in the inflated state, with the sleeve of the uterine manipulator instrument in the distal position such that the colpotomy cup of the sleeve is engaged with the cervix, and with a balloon of the sleeve in an inflated state.

With the position of uterine manipulator (300) being fixed by the combination of balloon (324) and colpotomy cup (350), balloon (332) is inflated as shown in FIG. 25E. Balloon (332) bears outwardly against the sidewall of the vagina (V), thereby creating a fluid-tight seal against the sidewall of the vagina (V).

With uterine manipulator (300) being positioned and configured as shown in FIG. 25E, robotic arm (200) may be utilized to drive uterine manipulator (300) to various positions, to thereby re-orient and reposition the uterus (U) as desired by the clinician who is performing the rest of the medical procedure (e.g., hysterectomy). In some scenarios, the clinician who robotically controls robotic arm (200) to drive uterine manipulator (300) to position and orient the uterus (U) also uses the same robotic system to control instruments that are used to perform a surgical procedure associated with the uterus (U) (e.g., a hysterectomy). As noted above, by allowing a surgeon to directly control the manipulation of the uterus (U) via robotic arm (200) and uterine manipulator (300), the process avoids potential confusion and inconsistency that might otherwise result in procedures where a human assistant is controlling a uterine manipulator based on commands from another human clinician. Moreover, once the uterus (U) has been manipulated to achieve the desired position and orientation, robotic arm (200) and uterine manipulator (300) may cooperate to maintain this position and orientation of the uterus (U) indefinitely. This may avoid scenarios where a human operator of a uterine manipulator might inadvertently reposition or reorient the uterus (U) the middle of a medical procedure.

As noted above, one medical procedure that may be performed using robotic arm (200) and uterine manipulator (300) is a hysterectomy. In some versions of such a procedure, one or more cutting instruments are introduced laparoscopically via the patient's abdomen to approach the cervicovaginal junction from outside the uterus (U) and vagina (V). Such instrumentation may be controlled manually or robotically. In versions where the instrumentation is controlled robotically, the same robotic system may control the instrumentation and robotic arm (200). A cutting instrument may cut the uterus (U) away at the cervicovaginal junction, generally tracing around the circular perimeter defined by distal end (360) of colpotomy cup (350).

In some versions, the tissue at the cervicovaginal junction may be distended in response to pressure imposed by distal end (360) of colpotomy cup (350), thereby promoting visualization of the position of distal end (360) of colpotomy cup (350) from a laparoscope that is positioned external to the uterus (U) and vagina (V). Distal end (360) may also urge the ureters of the patient outwardly, thereby reducing the risk of the cutting instrument inadvertently cutting one of the ureters. Also in some versions, the cutting instrument may be received in space (366) defined between edges (362, 364) at distal end (360) of colpotomy cup (350) as the cutting instrument travels in a generally circular motion along the cervicovaginal junction. This cutting at the cervicovaginal junction will ultimately result in separation of the uterus (U)

from the vagina (V); and the end of the vagina (V) may be appropriately closed at this point. During this process, the patient's abdomen may be insufflated with pressurized gas, and the pressurized insufflation gas may eventually reach the distal region of the vagina (V). In such scenarios, balloon (332) will provide sealed occlusion that is sufficient to prevent the pressurized insufflation gas from escaping out of the patient via the vagina (V).

While robotic arm (200) and uterine manipulator (300) are described in the foregoing example as being used in a hysterectomy, robotic arm (200) and uterine manipulator (300) may be used in any other suitable fashion and may be used in any other suitable procedures.

III. Example of Uterine Manipulator Control Via Enhanced Laparoscopic View

During a medical procedure (e.g., hysterectomy, etc.) in which uterine manipulator (300) is used, one or more incisions may be formed in the patient's abdomen; and instruments may be inserted through those incisions. Such instruments may include one or more laparoscopes, one or more tissue graspers, one or more cutting instruments, one or more tissue sealing instruments (e.g., RF instruments, etc.), and/or various other kinds of instruments. In such scenarios where a laparoscope is inserted into the patient's abdomen, the laparoscope may provide visualization of the uterus (U) and surrounding anatomical structures. A surgeon may observe the laparoscopic view via a display screen (e.g., touchscreen (26) on a console such as console (16, 31).

In procedures where a non-robotic uterine manipulator is used, a surgeon may observe a laparoscopic view on a display screen while instructing another person to operate the uterine manipulator to achieve a desired position and orientation of the uterus (U). However, when a robotic uterine manipulator like uterine manipulator (300) is used, the same surgeon who is robotically operating other instruments (e.g., graspers, cutting instruments, etc.) may also robotically operate uterine manipulator (300). It may therefore be desirable to enhance the laparoscopic view on a display screen to provide features that further promote the surgeon's control over the robotically operated uterine manipulator (300) while viewing the display screen. It may further be desirable to facilitate control of a uterine manipulator (300) by an operator who is contemporaneously viewing the uterus (U) of the patient in a laparoscopic view on a display screen. Examples of features that may provide such capabilities are described in greater detail below.

Figure 26:
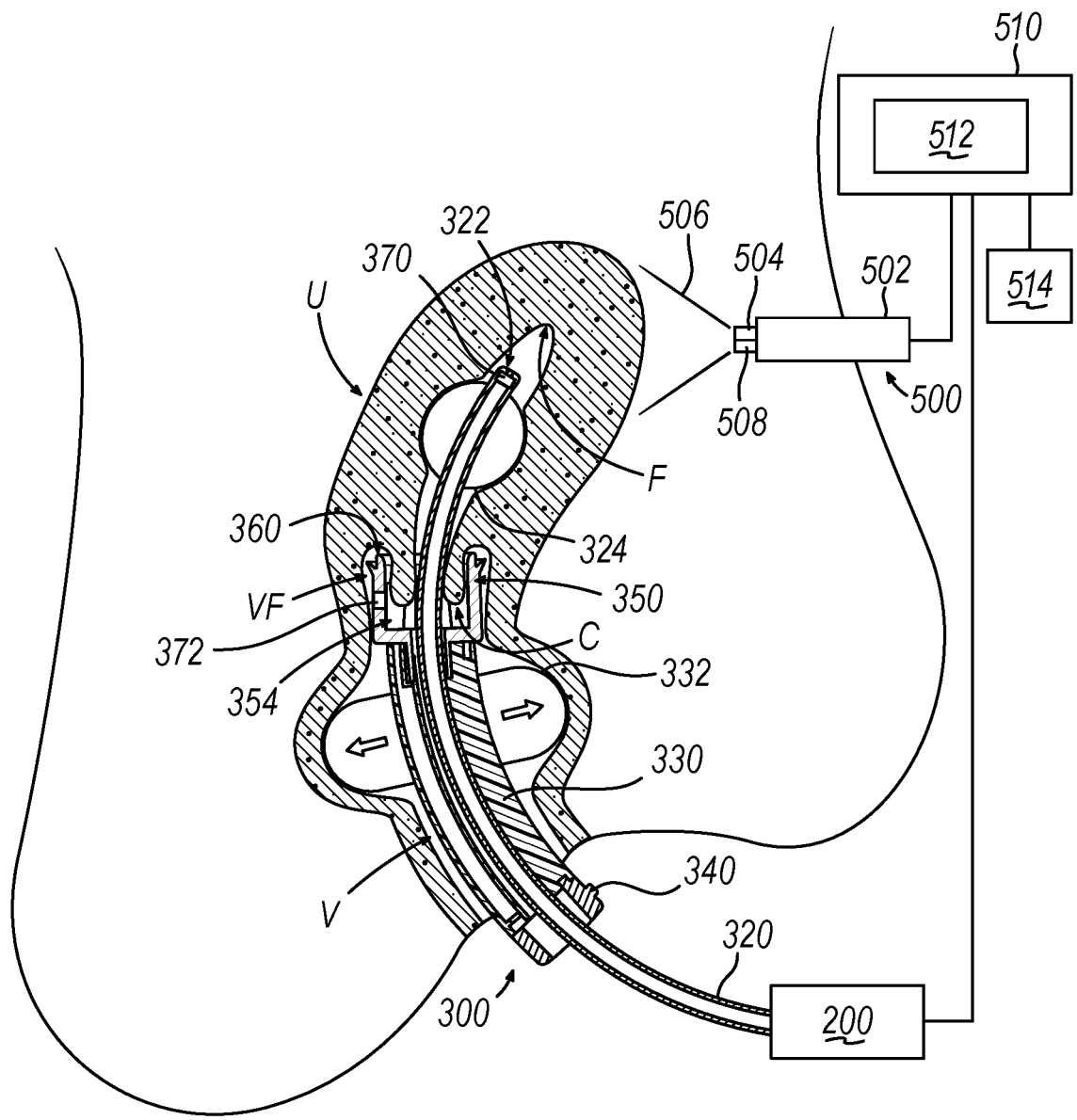
FIG. 26 depicts a mid-sagittal cross-sectional view of the vagina and uterus of FIG. 25A, with a uterine manipulator instrument positioned and configured as shown in FIG. 25E, with a laparoscope disposed in an abdominal cavity adjacent to the uterus, and with the laparoscope coupled with a console.

FIG. 26 shows an arrangement that includes uterine manipulator (300), a laparoscope (500), and a console (510). Uterine manipulator (300) of the present example is coupled with a robotic arm (200), which is shown schematically in FIG. 26 but may be configured and operable as described above with reference to FIG. 21. Uterine manipulator (300) of the present example further includes a pair of position sensors (370, 372). Position sensor (370) is positioned at or near distal end (322) of shaft (320). Position sensor (370) is operable to generate signals indicative of the position of distal end (322) in three-dimensional space. Position sensor (372) is positioned at or near distal end (360) of colpotomy cup (350). Position sensor (372) is operable to generate signals indicative of the position of distal end (360) in three-dimensional space. In some versions, each position sensor (370, 372) includes one or more conductive coils that are configured to generate position-indicative signals in response to one or more electromagnetic fields that are generated by one or more electromagnetic field generators (not shown) that are positioned externally to the patient. Alternatively, the positions of distal ends (322, 360) may be determined in any other suitable fashion, including but not limited to kinematic data associated with movement of robotic arm (200) and/or optical sensing or computer vision.

Laparoscope (500) of the present example includes a body (502) that is configured for insertion through an abdomen of a patient (e.g., via a trocar, etc.). An imaging element (504) and an illumination element (508) are positioned at the distal end of body (502). Imaging element (504) may comprise one or more cameras providing a field of view (506) within the abdominal cavity (AC) of the patient, with field of view (506) providing a view of the exterior of the uterus (U). Illumination element (508) may comprise one or more LEDs and/or any other suitable light source(s) to illuminate field of view (506). Laparoscope (500) is coupled with console (510) such that console (510) may be used to view images captured by imaging element (504) as will be described in greater detail below. While only one laparoscope (500) is shown in the present example, some other procedures may employ two or more laparoscopes to thereby provide two or more corresponding fields of view (506).

Console (510) may be configured and operable like consoles (16, 31) described above. Console (510) includes a display screen (512) that is operable to display images corresponding to field of view (506) of laparoscope (500). Robotic arm (200) and a user input assembly (514) are both coupled with console (510), such that an operator may operate user input assembly (514) to drive movement of robotic arm (200) (and thereby drive movement of uterine manipulator (300)) while observing images on display screen (512) of console (510). User input assembly (514) may include any suitable user input feature or combination of user input features, including but not limited to one or more touchpads, one or more joysticks, one or more buttons, a mouse, etc. In addition, or in the alternative, user input assembly (514) may include a touchscreen overlay on display screen (512), such that display screen (512) is effectively configured to receive user input.

Regardless of the form that user input assembly (514) takes, some versions of user input assembly (514) may be operable to control operation of other components in addition to being operable to control uterine manipulator (300) via robotic arm (200). For instance, user input assembly (514) may be operable to control laparoscope (514), other instruments, other robotic arms (200), etc. In some such versions, user input assembly (514) includes a feature allowing the operator to toggle among different modes to select which component(s) the user wishes to control via user input assembly (514). In some other versions, user input assembly (514) includes different features that control different components, such that the operator need not necessarily toggle between different modes for user input assembly (514) to control different components.

Figure 27A:
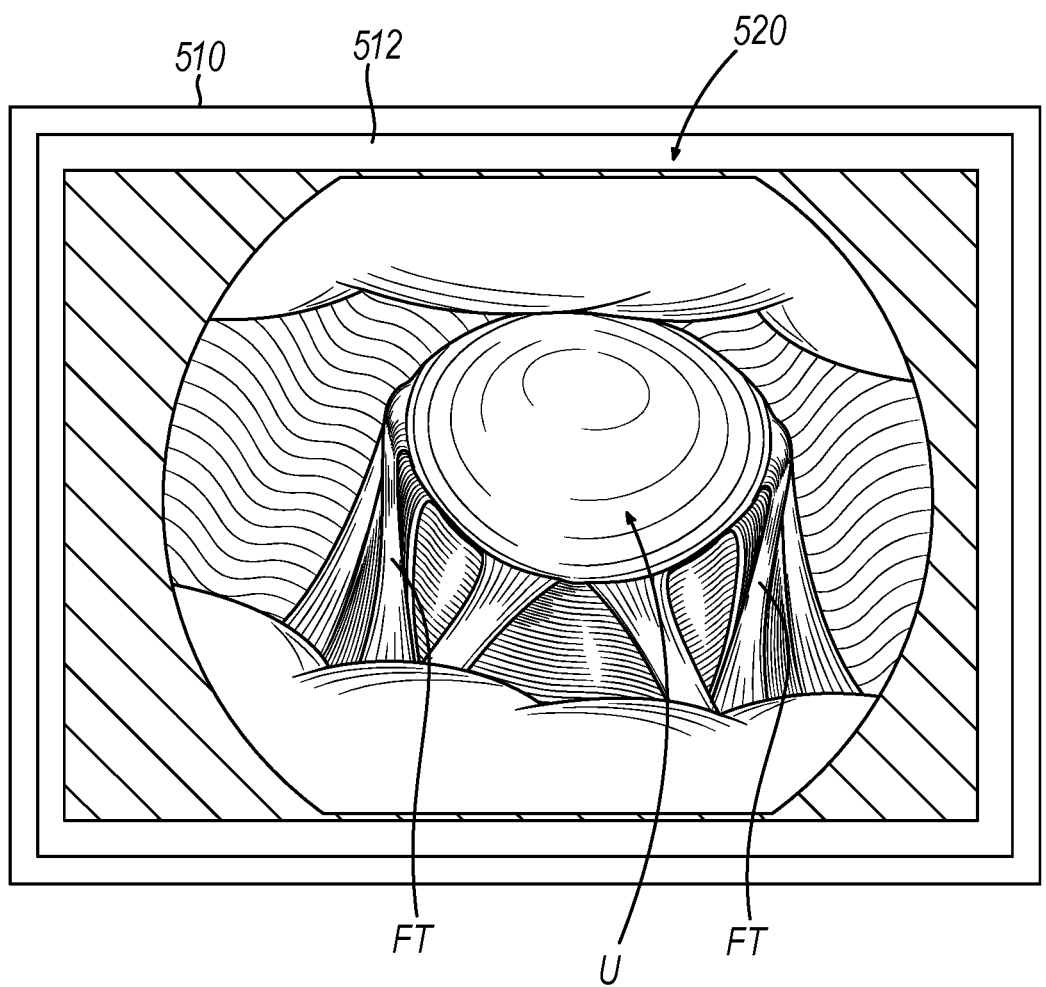
FIG. 27A depicts an example of a display on a screen of the console of FIG. 26, showing a view from the laparoscope of FIG. 26.
Figure 27B:
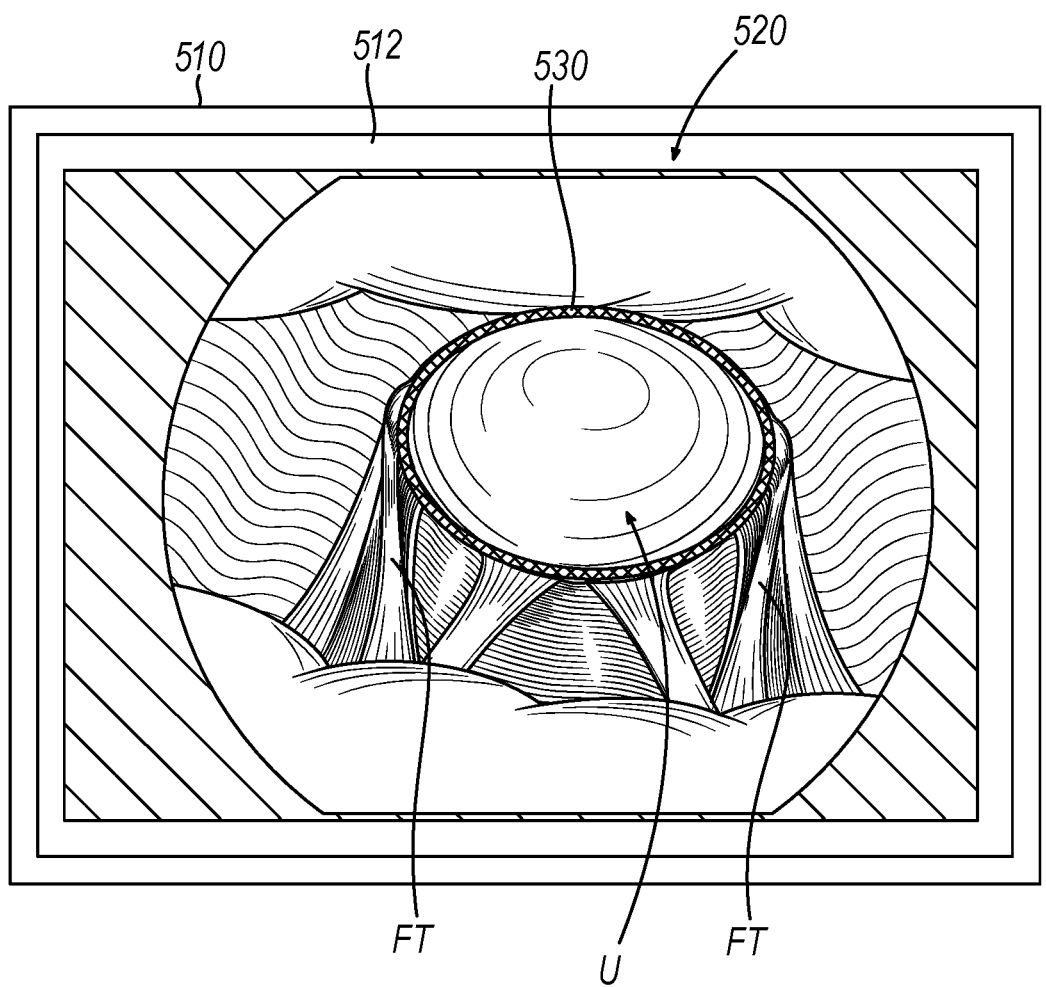
FIG. 27B depicts an example of a display on a screen of the console of FIG. 26, showing a view from the laparoscope of FIG. 26, with an indicator overlaid on the view showing the uterus in a disengaged state.

FIG. 27A shows an example of a laparoscopic view (520) that may be provided on display screen (512). Laparoscopic view (520) corresponds to field of view (506) of laparoscope (500), such that the uterus (U) may be seen in laparoscopic view (520) in real time. In the example shown, the fallopian tubes (FT) of the patient may also be seen in laparoscopic view (520). FIG. 27B shows an example of an enhanced version of laparoscopic view (520), where an indicator (530) is overlaid onto laparoscopic view (520). Indicator (530) is in the form of an oval that generally indicates the perimeter of the uterus (U). Indicator (530) is configured to remain on the perimeter of the uterus (U) even if laparoscope (520) is repositioned (e.g., pivoted, etc.) within the abdominal cavity, such that indicator (530) serves as an "augmented reality" feature to provide a real-time indication of the position of the uterus (U) within laparoscopic view (520). While indicator (530) of the present example has an oval shape, indicator (530) may alternatively take any other suitable form.

Indicator (530) may be generated and applied in various ways. In some versions, the operator manipulates user input feature (514) to effectively draw indicator (530) on display screen (512), such that indicator (530) is generated and positioned manually. In versions where display screen (512) is in the form of a touchscreen, the operator may directly draw indicator (530) on display screen (512). In some other versions, indicator (530) is automatically generated based on optical sensing or computer vision. For instance, console (510) may execute image recognition algorithms to automatically detect the perimeter of the uterus (U) in laparoscopic view (520), and thereby automatically generate indicator (530) on laparoscopic view (520). Some versions of optical sensing or computer vision may include use of indocyanine green (ICG) fluorescence imaging, multispectral imaging, hyperspectral imaging, photoacoustic imaging, ultrasonic imaging, and/or other kinds of imaging.

By way of further example, the perimeter of uterus (U) may be automatically detected, to thereby automatically generate indicator (530) on laparoscopic view (520), using components and techniques as described in U.S. Pat. Pub. No. 2017/0055819, entitled "Set Comprising a Surgical Instrument," published Mar. 2, 2017, the disclosure of which is incorporated by reference herein in its entirety; U.S. Pat. Pub. No. 2017/0251900, entitled "Depiction System," published Sep. 7, 2017, the disclosure of which is incorporated by reference herein in its entirety; U.S. Pat. Pub. No. 2020/0015925, entitled "Combination Emitter and Camera Assembly," published Jan. 16, 2020, the disclosure of which is incorporated by reference herein, in its entirety; U.S. Pat. Pub. No. 2020/0015899, entitled "Surgical Visualization with Proximity Tracking Features," published Jan. 16, 2020, the disclosure of which is incorporated by reference herein, in its entirety; U.S. Pat. Pub. No. 2020/0015924, entitled "Robotic Light Projection Tools," published Jan. 16, 2020; and U.S. Pat. Pub. No. 2020/0015898, entitled "Surgical Visualization Feedback System," published Jan. 16, 2020, the disclosure of which is incorporated by reference herein, in its entirety; and/or U.S. Pat. No. 9,274,047, entitled "System and Method for Gross Anatomic Pathology Using Hyperspectral Imaging," issued Mar. 1, 2016, the disclosure of which is incorporated by reference herein in its entirety.

As part of the process of generating and positioning indicator (530), some versions may also factor in position data from one or both of position sensors (370, 372), kinematic data associated with movement and positioning of features of robotic arm (200), and/or other kinds of data. In versions where distal end (322) of shaft (320) includes a light source that is operable to provide transillumination through the tissue of the uterus (U), such transillumination effects may further enhance an image recognition algorithm. Even in versions where indicator (530) is generated automatically, console (510) may prompt the operator to provide confirmation that indicator (530) has been generated and positioned properly. In some such versions, console (510) may permit the operator to manually adjust the size, position, or other parameters of indicator (530) to more accurately correspond with the position of the uterus (U). Similarly, some versions may permit the operator to manually define or adjust the size, position, or other parameters of indicator (530) to account for abnormal anatomy and/or to identify preferred dissection zones, etc. Alternatively, indicator (530) may be generated and applied in any other suitable fashion.

In the state shown in FIG. 27B, console (510) has effectively recognized and indicated the position of the uterus (U) via indicator (530). However, the operator has not yet engaged user input feature (514) to reposition or reorient the uterus (U) via uterine manipulator (300) and robotic arm (200). For instance, the operator may not yet be contacting user input feature (514). Alternatively, the operator may not yet have placed user input feature (514) in a mode where user input feature is operable to control movement of uterine manipulator (300) via robotic arm (200). In either scenario (or in similar scenarios), user input feature (514) may be regarded as being in a non-engaged state. In some versions, the form of indicator (530) shown in FIG. 27B (e.g., a hollow oval shape) provides further indication that user input feature (514) is in the non-engaged state. In other words, indicator (530) indicates a state of user input feature (514) in addition to indicating the position of the uterus (U).

Figure 27C:
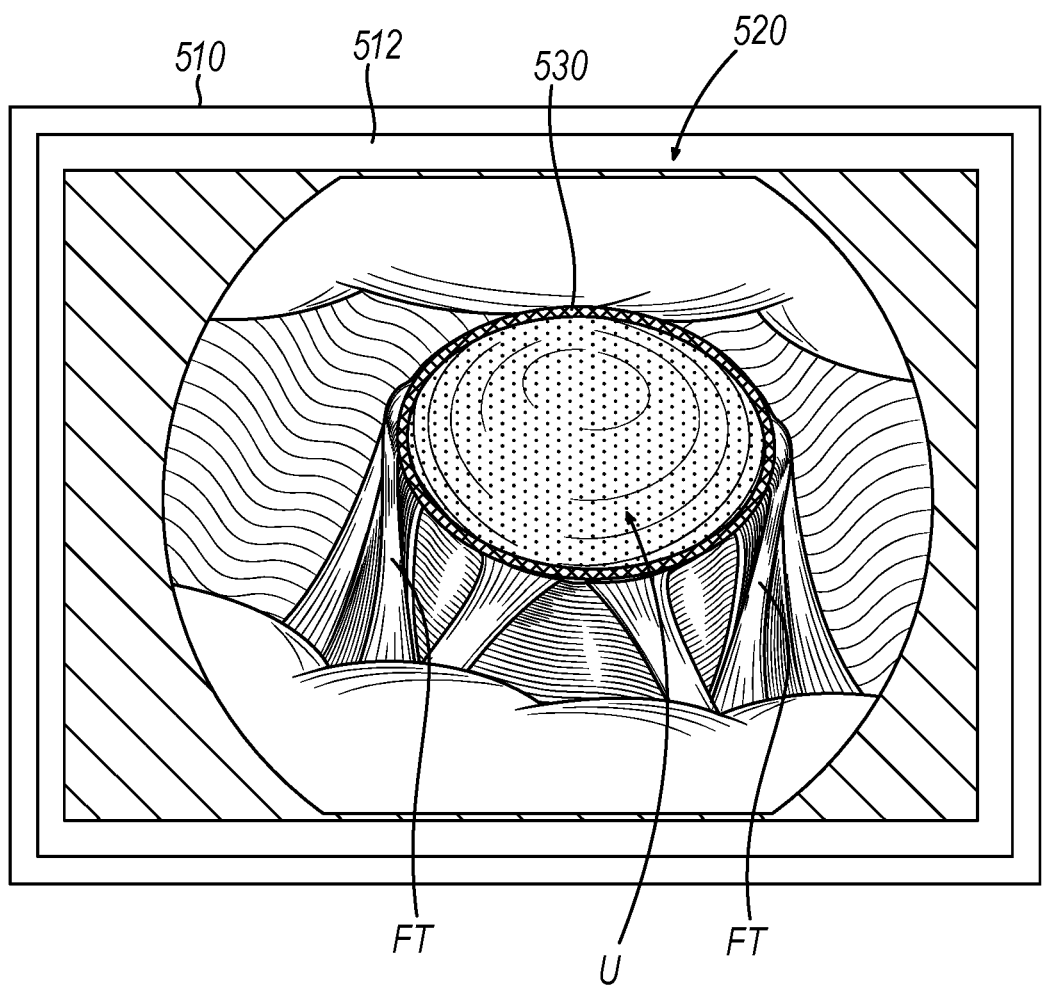
FIG. 27C depicts an example of a display on a screen of the console of FIG. 26, showing a view from the laparoscope of FIG. 26, with an indicator overlaid on the view showing the uterus in an engaged state.

FIG. 27C shows an example of what indicator (530) may look like once the operator has engaged user input feature (514) to reposition or reorient the uterus (U) via uterine manipulator (300) and robotic arm (200). For instance, user input feature (514) may transition from the non-engaged state to the engaged state when the operator contacts user input feature (514) with their hand, etc. Alternatively, user input feature (514) may transition from the non-engaged state to the engaged state when the operator transitions user input feature (514) into a mode where user input feature is operable to control movement of uterine manipulator (300) via robotic arm (200). In either scenario (or in similar scenarios), user input feature (514) may be regarded as being in an engaged state. Indicator (530) may change in appearance in response to user input feature (514) transitioning from the non-engaged state to the engaged state. In the example shown in FIG. 27C, indicator (530) has transitioned from being a hollow oval to being a shaded-in oval. Of course, indicator (530) may make any other suitable transition to visually indicate when the operator has successfully engaged user input feature (514) to reposition or reorient the uterus (U) via uterine manipulator (300) and robotic arm (200).

Figure 27D:
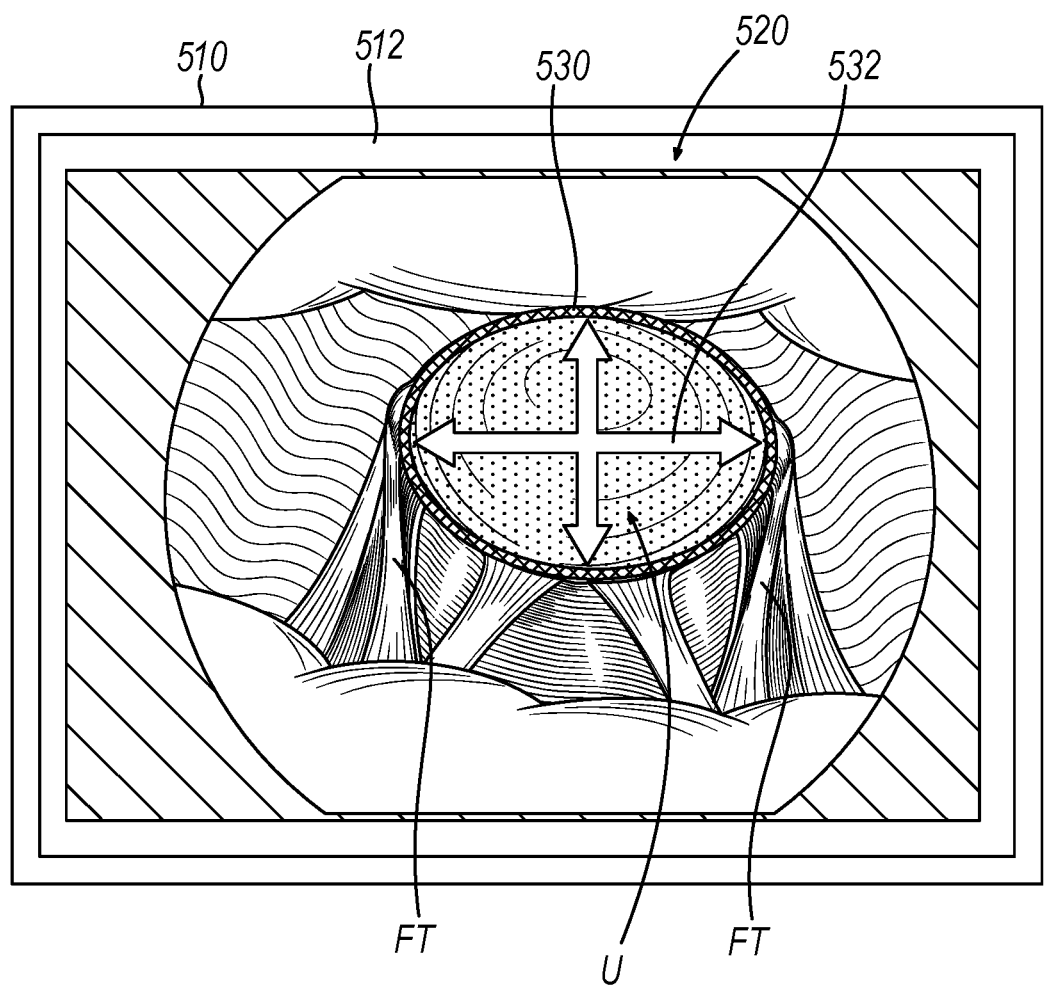
FIG. 27D depicts an example of a display on a screen of the console of FIG. 26, showing a view from the laparoscope of FIG. 26, with an indicator overlaid on the view showing the uterus being moved via the uterine manipulator of FIG. 26.

In any case, once the operator sees indicator (530) in the state shown in FIG. 27C, the operator may then utilize the engaged user input feature (514) to drive movement of the uterus (U) via uterine manipulator (300) and robotic arm (200). Once the operator starts utilizing the engaged user input feature (514) to drive movement of the uterus (U) via uterine manipulator (300) and robotic arm (200), indicator (530) may be further updated as shown in FIG. 27D. In particular, indicator (530) may remain shaded-in; and may move with the uterus (U) as the uterus (U) moves within the laparoscopic view (520). Indicator (530) may thus enhance the operator's visualization of the movement of the uterus (U). In addition, indicator (530) may be further updated with an arrow overlay (532) showing the direction or directions of movement of the uterus (U). In the present example, arrow overlay (532) is shown as four perpendicular arrows. In such versions, one or more of these arrows corresponding to the direction(s) of movement of the uterus (U) may be illuminated or otherwise affected to show such movement. In some other versions, only a single arrow or set of arrows is shown to correspond with the real-time direction(s) of movement of the uterus (U). Alternatively, arrow overlay (532) may be substituted with any other suitable feature to indicate the direction(s) of movement of the uterus (U) in real time.

Various suitable techniques may be used to provide movement of indicator (530) and activation of arrow overlay (532) while the uterus (U) is being moved as shown in FIG. 27D. For instance, console (510) may rely on the user input that is being provided via user input feature (514) to correspondingly update the position of indicator (530); and to correspondingly activate arrow overlay (532). In addition, or in the alternative, console (510) may rely on optical sensing or computer vision via imaging element (504) of laparoscope (500) to visually track movement of the uterus (U); and update indicator (530) and arrow overlay (532) accordingly. In addition, or in the alternative, console (510) may rely on position data from one or both of position sensors (370, 372), kinematic data associated with movement and positioning of features of robotic arm (200), and/or other kinds of data to effectively track movement of the uterus (U); and update indicator (530) and arrow overlay (532) accordingly. Alternatively, indicator (530) and arrow overlay (532) may be updated in any other suitable fashion.

It should be understood from the foregoing that the addition of indicator (530) and arrow overlay (532) onto laparoscopic view (520) may enhance the ability of the operator to control manipulation of the uterus (U) via uterine manipulator (300) and robotic arm (200). Such visual enhancement of indicator (530) and arrow overlay (532) may provide the operator with an intuitive "click and drag" or "touch and drag" type of control of movement and reorientation of the uterus (U), with the "click" or "touch" being indicated via the shaded version of indicator (530) in FIG. 27C; and with the "drag" being indicated via the arrow overlay (532) in FIG. 27D. In some variations where display screen (512) is a touchscreen that effectively serves as user input feature (514) for controlling uterine manipulator (300) and robotic arm (200), the "click" or "touch" engagement associated with FIG. 27C may occur when the operator touches display screen (512) (e.g., within the perimeter defined by indicator (530)); and the "drag" movement control of uterine manipulator (300) via robotic arm (200) may occur when the operator drags their finger or finger along display screen (512) in the direction(s) of the intended movement of the uterus (U). Similar intuitive "click and drag" or "touch and drag" type of control may also be executed via a touchpad of user input feature (514).

To the extent that the "click and drag" or "touch and drag" type of control is from the perspective of the laparoscopic view (520), the movement in the laparoscopic view (520) may be opposite the insertion direction of the uterine manipulator. Thus, when the operator engages display screen (512) to apply "click and drag" or "touch and drag" type of control by moving their cursor or finger to the right (as viewed on display screen (512)), uterine manipulator (300) may in fact move to the left (as viewed from the proximal portion of uterine manipulator (300) toward the distal portion of uterine manipulator (300)). Thus, the "click and drag" or "touch and drag" type of control may be regarded as a "mirrored" control. In other words, with mirrored control, the motion of uterine manipulator (300) (as viewed from the proximal portion of uterine manipulator (300) toward the distal portion of uterine manipulator (300)) may be in the direction that is opposite to the direction of the operator's control motion (as viewed on display screen (512)). Such mirrored control may make the feel and operation more intuitive for the operator.

IV. Example of Uterine Manipulator Control with Critical Structure Presentation

During a hysterectomy procedure, it may be desirable to ensure that the surgeon is aware of the locations of various anatomical structures that are within the vicinity of the uterus (U), including but not limited to the fallopian tunes (FT), the ureters, etc. To the extent that these anatomical structures move or are otherwise reoriented during the process of manipulating the uterus (U) and/or at other stages of the procedure, it may be desirable to facilitate visual tracking of such structures in real time via display screen (512). The following examples relate to the identification of certain anatomical structures within laparoscopic view (520); and the subsequent tracking of those identified anatomical structures within laparoscopic view (520).

Figure 28:
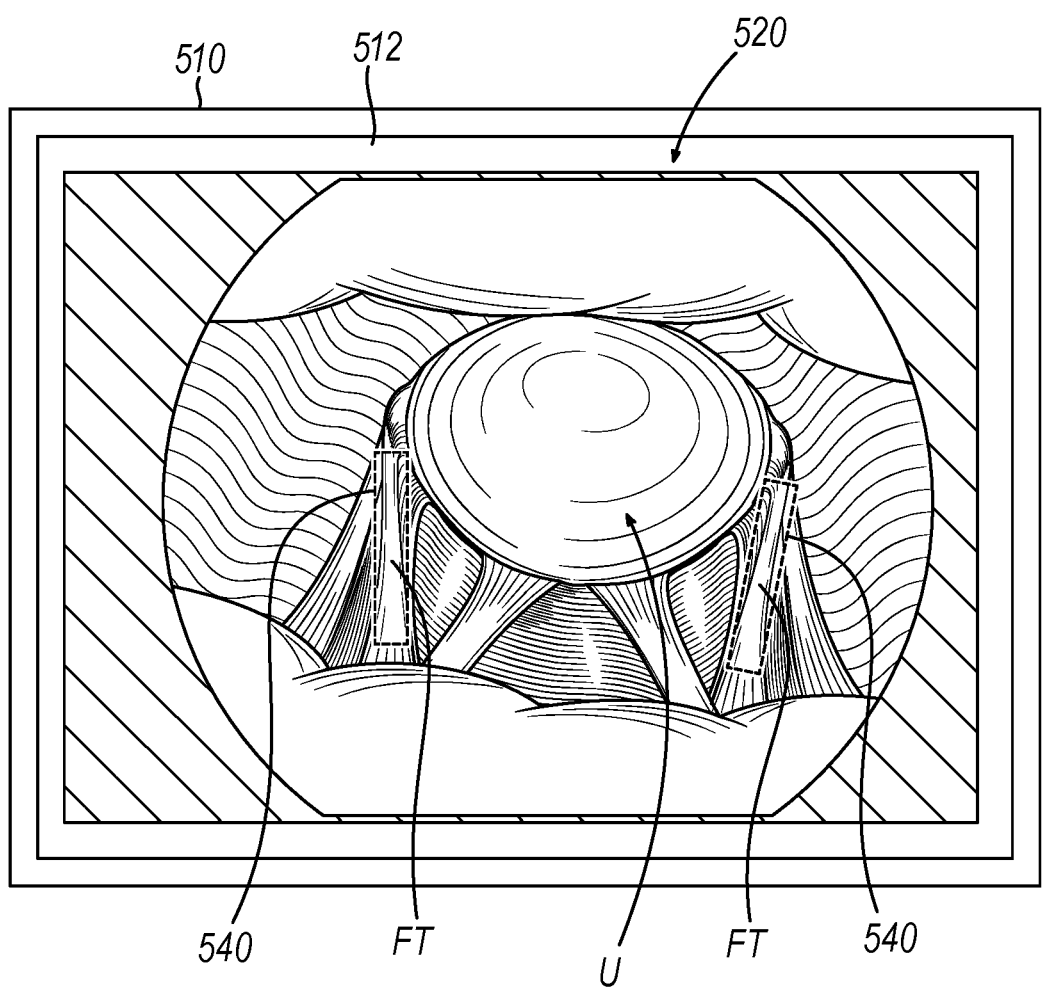
FIG. 28 depicts an example of a display on a screen of the console of FIG. 26, showing a view from the laparoscope of FIG. 26, with indicators overlaid on the view to indicate the location of fallopian tubes.

FIG. 28 shows a version of laparoscopic view (520) in which indicators (540) are overlaid onto laparoscopic view (520) to indicate the real-time position of fallopian tubes (FT). In this example, indicators (540) are in the form of rectangles that generally surround the perimeter of the corresponding fallopian tubes (FT). Alternatively, indicators (540) may take any other suitable form. Examples of how indicators (540) may be initially placed will be described in greater detail below. Once indicators (540) have been placed, indicators (540) may remain positioned over the fallopian tubes (FT) even as the fallopian tubes (FT) are repositioned or reoriented as the uterus (U) is repositioned or reoriented (e.g., using uterine manipulator (300) via robotic arm (200)). Indicators (540) may thus effectively move with the fallopian tubes (FT), in real time, within laparoscopic view (520).

While indicators (540) are shown in FIG. 28 only on fallopian tubes (FT), similar indicators may be laid over any other suitable anatomical structures within laparoscopic view (520). In some versions, different styles of indicators may be used to visually indicate different anatomical structures. For instance, indicators (540) that are used to indicate the real-time position and orientation of fallopian tubes (FT) may have one color; while indicators that are used to indicate the real-time position and orientation of ureters may have another color. While indicators (540) are shown in FIG. 28 without indicator (530) or arrow overlay (532), indicators (540) may appear within the same laparoscopic view (520), indicator (530), arrow overlay (532), and/or other kinds of overlays.

Various kinds of techniques may be used to identify anatomical structures such as the fallopian tubes (FT), to thereby generate and position indicators such as indicators (540) on those anatomical structures. In some versions, the process is manual, such that the operator manipulates user input feature (514) to effectively draw indicators (540) on display screen (512). In versions where display screen (512) is a touchscreen, such that display screen effectively serves as user input feature (514), the operator may manually draw indicators (540) via display screen (512). In some other versions, indicators (540) are automatically generated based on optical sensing or computer vision. For instance, console (510) may execute image recognition algorithms to automatically detect the locations of the fallopian tubes (FT) in laparoscopic view (520), and thereby automatically generate indicators (540) on laparoscopic view (520). Some versions of optical sensing or computer vision may include use of indocyanine green (ICG) fluorescence imaging, multispectral imaging, hyperspectral imaging, photoacoustic imaging, ultrasonic imaging, and/or other kinds of imaging.

By way of further example, the locations of the fallopian tubes (FT) (and/or other anatomical structures) may be automatically detected, to thereby automatically generate indicators (540) on laparoscopic view (520), using components and techniques as described in U.S. Pat. Pub. No. 2017/0055819, entitled "Set Comprising a Surgical Instrument," published Mar. 2, 2017, the disclosure of which is incorporated by reference herein in its entirety; U.S. Pat.

Pub. No. 2017/0251900, entitled "Depiction System," published Sep. 7, 2017, the disclosure of which is incorporated by reference herein in its entirety; U.S. Pat. Pub. No. 2020/0015925, entitled "Combination Emitter and Camera Assembly," published Jan. 16, 2020, the disclosure of which is incorporated by reference herein, in its entirety; U.S. Pat. Pub. No. 2020/0015899, entitled "Surgical Visualization with Proximity Tracking Features," published Jan. 16, 2020, the disclosure of which is incorporated by reference herein, in its entirety; U.S. Pat. Pub. No. 2020/0015924, entitled "Robotic Light Projection Tools," published Jan. 16, 2020; and U.S. Pat. Pub. No. 2020/0015898, entitled "Surgical Visualization Feedback System," published Jan. 16, 2020, the disclosure of which is incorporated by reference herein, in its entirety; and/or U.S. Pat. No. 9,274,047, entitled "System and Method for Gross Anatomic Pathology Using Hyperspectral Imaging," issued Mar. 1, 2016, the disclosure of which is incorporated by reference herein in its entirety.

As part of the process of generating and positioning indicators (540), some versions may also factor in position data from one or both of position sensors (370, 372), kinematic data associated with movement and positioning of features of robotic arm (200), and/or other kinds of data. Even in versions where indicators (540) are generated automatically, console (510) may prompt the operator to provide confirmation that indicators (540) have been generated and positioned properly. In some such versions, console (510) may permit the operator to manually adjust the size, position, or other parameters of indicators (540) to more accurately correspond with the position of the fallopian tubes (FT). As yet another example, the fallopian tubes (FT) may be filled with an imaging enhancing substance, such as a radiopaque agent (e.g., methylene blue, etc.), a fluorescing agent (e.g., ICG, etc.), and/or any other suitable substance. Alternatively, indicators (540) may be generated and applied in any other suitable fashion.

Figure 29:
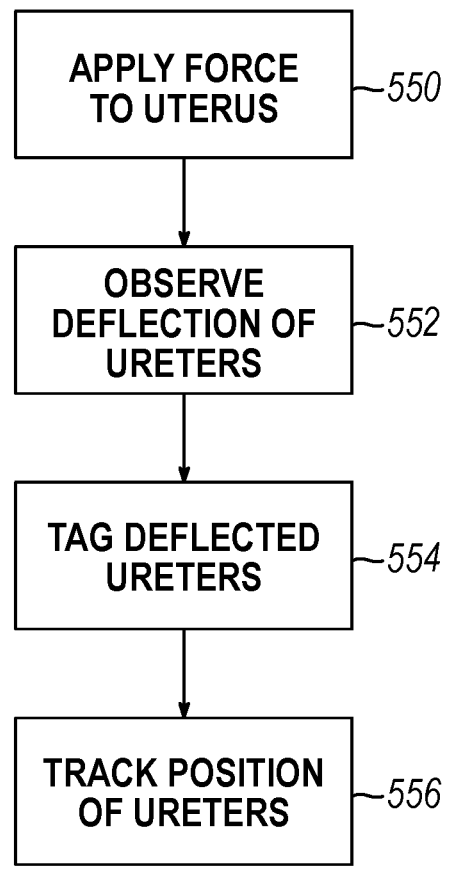
FIG. 29 depicts a flow chart showing examples of steps that may be carried out to tag and track ureters.

FIG. 29 shows an example of a process where indicators like indicators (540) may be used to identify and track ureters in laparoscopic view (520). The process shown in FIG. 29 may begin with uterine manipulator (300) already fully inserted into the patient, as shown in FIG. 26, such that distal end (322) of shaft (320) is positioned to engage the fundus (F) of the uterus (U). However, in some variations, sleeve (330) and colpotomy cup (350) are still in a proximal position, as shown in FIGS. 25B-25C, at the beginning of the process shown in FIG. 29. Moreover, balloon (324) may be in a deflated state (FIG. 25B) or an inflated state (FIG. 25C) at the beginning of the process shown in FIG. 29. As shown in block (550), uterine manipulator (300) may be advanced distally within the patient to push on the fundus (F), which may result in outward deflection of the ureters. Specifically, pushing the fundus (F) may case the ureters to spread to the side of the uterocervical junction such that the ureters are more readily visualized in endoscopic view (520). In some versions, the operator manually advances uterine manipulator (300) distally within the patient to push on the fundus (F) (e.g., by grasping shaft (330) and manually moving shaft, by grasping a portion of robotic arm (200) and manually moving that portion of robotic arm (200), etc.). In some other versions, the operator utilizes robotic arm (200) (e.g., by manipulating user input feature (514), etc.) to robotically advance uterine manipulator (300) distally within the patient to push on the fundus (F).

Regardless of how uterine manipulator (300) is controlled to provide deflection of the ureters, the deflected ureters may be observed in laparoscopic view (520), as shown in block (550). The deflected ureters may then be tagged in the laparoscopic view, as shown in block (554), by overlaying indicators (e.g., similar to indicators (540)) over the ureters in laparoscopic view (520). Such overlaying of indicators over the ureters in laparoscopic view may be performed manually and/or automatically, as described above in the context of generating indicators (540).

Once the positions of the ureters have been tagged with indicators as described above, these indicators may remain laid over the ureters in laparoscopic view (520) throughout a surgical procedure. To the extent that the are moved, reoriented, or otherwise change position within laparoscopic view (520) during the surgical procedure, the indicators on the ureters may move with the ureters within the laparoscopic view, such that the position of the ureters may be visually tracked as shown in block (556). The same techniques described above as being available for initially identifying and tagging the ureters may be used to track movement of the ureters within laparoscopic view (520). As the operator continues the procedure and manipulates other instruments within the abdominal cavity (AC) of the patient, these instruments may appear within laparoscopic view (520). During such stages, the operator may observe the position of such instruments in relation to the indicators on the ureters within laparoscopic view, to ensure that the instruments do not inadvertently damage the ureters.

Of course, such indicators, and viewing of instrument positions in relation to such indicators, may also be utilized with respect to other anatomical structures. Such anatomical structures may include anatomical structures that the operator seeks to avoid with the instruments and/or anatomical structures that the operator seeks to target with the instruments. In the event that indicators are used to indicate anatomical structures that the operator seeks to avoid with instruments and anatomical structures that the operator seeks to target with the instruments, the indicators may vary to further indicate whether such structures are targeted or should be avoided. For instance, red indicators may be used to indicate anatomical structures that should be avoided by instruments; while green indicators may be used to indicate anatomical structures that are intentionally targeted for instruments.

In cases where console (510) has identified the locations of anatomical structures that should be avoided by instruments, console (510) may also establish "no-go" zones around such anatomical structures (in addition to or in lieu of applying indicators to such anatomical structures in laparoscopic view (520) to indicate such anatomical structures as ones that should be avoided). For instance, console (510) may apply control restrictions to robotic arms (200), preventing robotic arms (200) from being used in a way that would bring instruments coupled with robotic arms (200) into contact with such anatomical structures (even if the operator is otherwise commanding robotic arms (200) to make such contact between instruments and the anatomical structure). As another variation, console (510) may permit some degree of interaction between instruments on robotic arms (200) and the anatomical structures, but restrict the nature or degree of such interactions.

In some versions, a control algorithm stored in console (510) and executed through console (510) may require certain anatomical structures to be identified and indicated before console (510) will allow the operator to move forward with a surgical procedure using uterine manipulator (300) and/or other instrumentation that is coupled with one or more robotic arms (200). For instance, console (510) may require the location of the ureters to be identified before console (510) allows the operator to operate instruments in the abdominal cavity via robotic arms (200) that might damage the ureters. In some versions, console (510) requires the operator to manually identify and mark certain anatomical structures within laparoscopic view (520). In such versions, console (510) may present a listing of anatomical structures (e.g., via display screen (512) or otherwise) to the operator, such that the operator may proceed through the listing like a checklist. In some other versions, console (510) automatically identifies the location of certain anatomical structures, using any of the various techniques described herein or otherwise.

Regardless of whether the identification of the location of certain anatomical structures within laparoscopic view (520) is manual or automatic, it may be necessary or otherwise beneficial to move uterus (U) and/or other anatomical structures in order to reveal anatomical structures that are otherwise obscured. Again, this process of moving anatomical structures to reveal other anatomical structures for identification within laparoscopic view (520) may be manual or automatic. In manual implementations, the operator may need to move uterus (U) and/or other anatomical structures in order to reveal listed anatomical structures that are otherwise obscured. Such movement to promote visualization may be accomplished using tissue graspers, uterine manipulator (300), and/or other instrumentation. In automatic implementations, console (510) may automatically control one or more robotic arms (200) to move tissue graspers, uterine manipulator (300), and/or other instrumentation to reveal anatomical structures that are otherwise obscured. In some such automatic implementations, the uterus (U) and/or other anatomical structures may be moved through a predetermined pattern of movement and reorientation. In addition, or in the alternative, automatic implementations may adapt the automatic pattern of movement and reorientation of the uterus (U) and/or other anatomical structures based on whether and when the key anatomical structures are finally identified within laparoscopic view (520).

V. Example of Uterine Manipulator Control with Instrument Feature Presentation

As described above, it may be beneficial to provide "augmented reality" features via laparoscopic view (520) on display screen (512) to indicate the real-time position of anatomical structures such as the uterus (U), fallopian tubes (FT), and ureters; and to facilitate operation of uterine manipulator (300) to manipulate the position and orientation of the uterus (U). It may also be beneficial to provide further indication of the location(s) of certain components of uterine manipulator (300) by overlaying corresponding indicators within laparoscopic view (520). In other words, components of uterine manipulator (300) may be represented by indicators in laparoscopic view (520) similar to the way in which anatomical structures are represented by indicators (530, 540) as described above.

Figure 30:
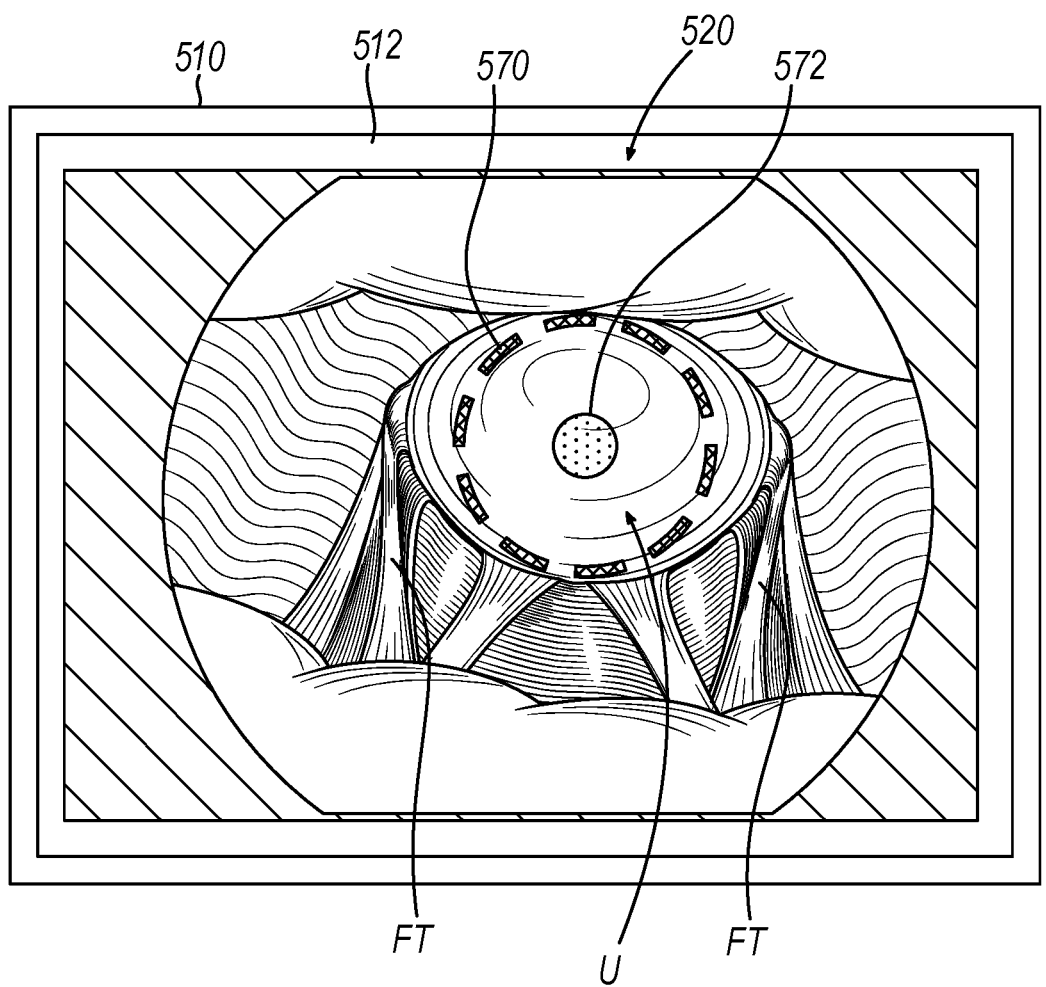
FIG. 30 depicts an example of a display on a screen of the console of FIG. 26, showing a view from the laparoscope of FIG. 26, with a first indicator overlaid on the view to indicate the location of the distal end of a shaft of the uterine manipulator of FIG. 26, and with a second indicator overlaid on the view to indicate the location of a distal edge of a colpotomy cup of the uterine manipulator of FIG. 26.
Figure 31:
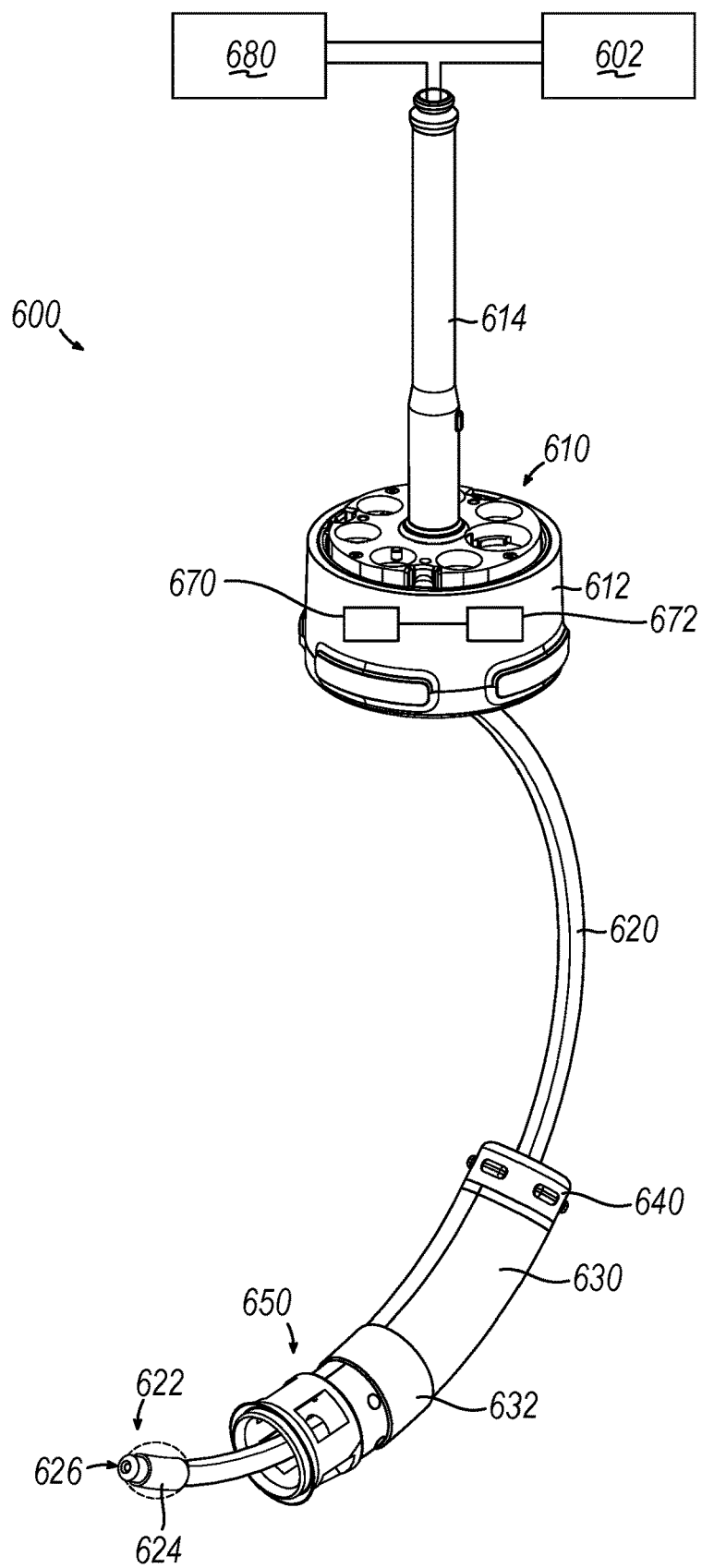
FIG. 31 depicts a perspective view of another example of a uterine manipulator.

As also described above, uterine manipulator (300) may include position sensor (370) that is usable to determine the position of distal end (322) of shaft (320); and a position sensor (372) that is usable to determine the position of distal end (360) of colpotomy cup (350). The position data acquired using position sensors (370, 372) may be processed by console (510) to correlate the real-time positions of distal ends (322, 360) with the corresponding regions depicted in laparoscopic view (520). By way of example only, the position data may be determined in relation to a global coordinate system, using electromagnetic tracking, using robotic control kinematics, and/or using any other suitable techniques. In any case, the position correlations may be used to generate indicators in laparoscopic view (520). An example of how this may be carried out is shown in FIG. 30. In this example, an indicator (570) is used to indicate the real-time position of distal end (360); while an indicator (572) is used to indicate the real-time position of distal end (322). As described above with respect to indicators (530, 540), the positions of indicators (570, 572) may move within laparoscopic view (520), based on corresponding movement of distal ends (322, 360), in real time. While FIG. 30 only shows indicators (570, 572), some implementations may show indicators (570, 572) and one or more other indicators (530, 540) simultaneously.

In use, an operator may wish to observe indicator (570) during initial stages of operation, such as during the stages depicted in FIGS. 25A-25B. For instance, console (510) may be configured to activate the presence of indicator (570) as soon as distal end (322) reaches the fundus (F) or some other position within the uterus (U). The operator may thus rely on the appearance of indicator (570) as an indication that balloon (324) may be inflated. The presence of indicator (570) may also be beneficial during subsequent use of uterine manipulator (300), such as by providing the operator with a better sense of the relative positioning of shaft (320) and the uterus (U).

The operator may wish to observe indicator (572) to when colpotomy cup (350) reaches the position shown in FIG. 25D. For instance, console (510) may be configured to activate the presence of indicator (572) as soon as distal end (360) reaches the vaginal fornix (VF) or some other position within the vagina (V). The operator may thus rely on the appearance of indicator (572) as an indication that balloon (332) may be inflated. The presence of indicator (572) may also be beneficial during subsequent use of uterine manipulator (300), such as by providing the operator with a target for a cutting instrument when the operator is ready to cut the uterus (U) from the cervix (C) along the cervicovaginal junction.

VI. Example of Fluid Expulsion Via Uterine Manipulator

In some scenarios, it may be desirable to dispense one or more fluids into the uterus (U) of a patient. For instance, it may be desirable to dispense a dye (e.g., methylene blue, etc.) within the uterus (U) as part of a chromopertubation process, to observe the extent to which the dye passes through the fallopian tubes (FT), to thereby evaluate patency of the fallopian tubes. Similarly, it may be desirable to dispense a dye to promote visualization of or within the uterus (U). For instance, it may be desirable to provide ICG based near-infrared (NIR) fluorescence imaging of the uterus (U), with ICG dye being dispensed within the uterus (U). As another merely illustrative example, it may be desirable to dispense a fluid within the uterus (U) in order to hydraulically clear obstructions, etc., within the fallopian tubes (FT). To the extent that a component of a uterine manipulator, like shaft (320) of uterine manipulator (300), may be readily introduced into the uterus (U) as described above, such a component may be used to dispense a fluid within the uterus (U) for any of the above-described purposes and/or for any other purposes as will be apparent to those skilled in the art in view of the teachings herein. The following provides examples of how a uterine manipulator like uterine manipulator (300) may be adapted to dispense fluids within a uterus (U).

FIG. 32 shows an example of a uterine manipulator (600) that is substantially similar to uterine manipulator (300). Uterine manipulator (600) of this example thus includes a head interface assembly (610), a shaft (620), a sleeve (630), a sleeve locking ring (640), and a colpotomy cup (650).

Head interface assembly (610) includes a base (612) and a shaft (614). Base (612) is configured to removably couple with head (240) of robotic arm (200) to thereby secure uterine manipulator (600) with head (240). Shaft (620) is configured to couple with a pressurized fluid source (602). An inflatable balloon (624) is positioned near distal end (622) of shaft (620). Sleeve (630) is slidably coupled to shaft (620). Locking ring (640) is rotatably secured to the proximal end of sleeve (630), while colpotomy cup (650) is fixedly secured to the distal end of sleeve (630). An inflatable balloon (632) is positioned along sleeve (630), between locking ring (640) and colpotomy cup (650). These components of uterine manipulator (600) are configured and operable like the similarly named components of uterine manipulator (300).

Unlike uterine manipulator (300), uterine manipulator (600) of the present example further includes an opening (626) at distal end (622). While only one opening (626) is shown, distal end (622) may include any suitable number of openings (626). While opening (626) is distally-presented in the present example, distal end (622) may include one or more laterally-presented openings (626) in addition to, or in lieu of, including distally-presented opening (626). While opening (626) is distal to balloon (624) in the present example, shaft (620) may include one or more openings proximal to balloon (624) in addition to, or in lieu of, including opening (626) distal to balloon (624).

Opening (626) is in fluid communication with a fluid reservoir (670), which is positioned in base (612) of head interface assembly (610) in the present example. One or more lumens may provide a pathway for fluid communication from fluid reservoir (670) to opening (626). In some versions, fluid reservoir (670) is in the form of a cartridge that is removable from base (612). In such versions, a cartridge form of fluid reservoir (670) may enable an operator to replace fluid reservoir (670) whenever the fluid is depleted from fluid reservoir (670). Similarly, the operator may select from various different kinds of cartridges containing different kinds of fluids, such that the operator may select and install the cartridge containing the particular kind of fluid that is best suited for the procedure at hand. In some other versions, fluid reservoir (670) may be integrally formed within base (612), such that a replaceable cartridge is not provided. In some such versions, base (612) includes a filling port allowing the operator to fill fluid reservoir (670) with a selected fluid. Some such versions may also include a draining port allowing the operator to drain any remaining fluid from fluid reservoir (670) after the medical procedure is complete. While fluid reservoir (670) is contained within head (612) in the present example, some other versions may provide fluid reservoir (670) separate from head (612). For instance, fluid reservoir (670) may be positioned elsewhere within the operating room and may be coupled with head (612) or shaft (614), etc., via one or more flexible tubes.

A fluid pump (672) is also provided in base (612) of head interface assembly (610) in the present example. Fluid pump (672) is operable to drive fluid from fluid reservoir (670) to opening (626). Fluid pump (672) may take any suitable form and include any suitable features, including but not limited to a slidable piston (e.g., where fluid reservoir (670) is formed by a barrel in which the slidable piston is disposed), a peristaltic pump, etc. Fluid pump (672) is activated by a control module (680). Control module (680) may be a feature of any of the various consoles (16, 31, 510) described herein. Control module (680) may also be operable to drive or activate fluid source (602), robotic arm (200), and/or other system components. While fluid pump (672) is contained within head (612) in the present example, some other versions may provide fluid pump (672) separate from head (612). For instance, fluid pump (672) may be positioned elsewhere within the operating room.

In some versions, fluid pump (672) is activated manually by the operator providing an activation input to control module (680) in order to activate fluid pump (672). In some other versions, fluid pump (672) is activated automatically in response to some other kind of input. For instance, if an operator activates a NIR fluorescence imaging feature (e.g., an NIR version of laparoscope (500), etc.), such activation may automatically trigger fluid pump (672) to drive an ICG dye from fluid reservoir (670) out through distal opening (626). Similarly, an activated fluid pump (672) may be deactivated manually or automatically. In cases of automatic deactivation, such deactivation may occur upon expiration of a predetermined time period after activation. Alternatively, automatic deactivation may occur in response to one or more other conditions (e.g., deactivation of a NIR fluorescence imaging feature, etc.). As another illustrative example, fluid may be expelled through distal opening (626) to unblock the fallopian tubes (FT) and/or for any other suitable purpose(s).

As noted above in the context of FIGS. 26-29, it may be desirable to provide "augmented reality" indicators within a laparoscopic view (520), to indicate and track the real-time locations of certain anatomical features. In some scenarios, the identification and indication of the real-time locations of certain anatomical features within laparoscopic view (520) may be provided and/or promoted through use of imaging techniques that are enhanced by fluid expelled from opening (626) in the uterus (U). For instance, in cases where ICG dye is expelled from opening (626) in the uterus (U) and laparoscope (500) has NIR imaging capabilities, such capabilities may be leveraged to provide indication and tracking of the real-time locations of the uterus (U) (and perhaps the fallopian tubes (FT)) within laparoscopic view (520) in accordance with the teachings provided above in the context of FIGS. 26-29.

As noted above, any of the various procedures described herein may be executed using a console such as any of the various consoles (16, 31, 510) described herein. Such consoles (16, 31, 510) may include a processor and a processor-readable medium including contents that are configured to cause the processor to perform the procedures described herein. Control module (680) and/or other components of a console such as any of the various consoles (16, 31, 510) described herein may include such a processor.

VII. Examples of Combinations

The following examples relate to various non-exhaustive ways in which the teachings herein may be combined or applied. The following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A system, comprising: (a) a uterine manipulator having a shaft, the shaft being configured to pass through a cervix of a patient and enter a uterus of the patient; (b) a robotic arm, the uterine manipulator being coupled with the robotic arm, the robotic arm being operable to drive movement of the uterine manipulator; (c) an imaging instrument operable to provide an image of an exterior of the uterus of the patient; (d) a user input feature configured to transition between an engaged state and a non-engaged state, the user input feature in the engaged state being operable to control movement of the robotic arm to thereby drive movement of the uterine manipulator; and (e) a console including a display screen, the console being configured to: (i) provide a view from the imaging instrument of the exterior of the uterus of the patient, on the display screen, and (ii) provide an indicator on the view from the imaging instrument, on the display screen, the indicator indicating whether the user input feature is in the engaged state or the non-engaged state.

Example 2

The system of Example 1, the imaging instrument comprising a laparoscope, the view comprising a laparoscopic view from the laparoscope.

Example 3

The system of any of Examples 1 through 2, the user input feature being positioned to enable an operator to control the user input feature while observing the display screen.

Example 4

The system of Example 3, the user input feature comprising one or more features selected from the group consisting of one or more touchpads, one or more joysticks, one or more buttons, a mouse, and combinations thereof.

Example 5

The system of any of Examples 3 through 4, the user input feature comprising a touchscreen overlay on the display screen.

Example 6

The system of any of Examples 4 through 5, the indicator comprising an overlay on the view from the imaging instrument.

Example 7

The system of any of Examples 1 through 6, the indicator comprising a shape configured to form an outline along at least a portion of the exterior of the uterus of the patient.

Example 8

The system of any of Examples 1 through 7, the indicator being configured to transition between a first appearance and a second appearance, the first appearance indicating that the user input feature is in the engaged state, the second appearance indicating that the user input feature is in the non-engaged state.

Example 9

The system of Example 8, the first appearance defining a hollow shape.

Example 10

The system of Example 9, the second appearance defining a filled-in shape.

Example 11

The system of any of Examples 1 through 10, the console indicator being further configured to provide a movement overlay on the view from the imaging instrument, the movement overlay being provided in response to an operator manipulating the user input feature to control movement of the robotic arm to thereby drive movement of the uterine manipulator.

Example 12

The system of Example 11, the movement overlay being positioned over the indicator.

Example 13

The system of any of Examples 11 through 12, the movement overlay including one or more arrows, the one or more arrows indicating one or more corresponding directions of movement of the uterus of the patient.

Example 14

The system of any of Examples 11 through 13, the indicator being configured to move with the uterus within the view from the imaging instrument, in response to movement of the uterus as driven by the uterine manipulator.

Example 15

The system of any of Examples 1 through 14, the uterine manipulator including one or more position sensors, the console being operable to determine a position of the uterine manipulator in the patient based on the one or more position sensors.

Example 16

A method, comprising: (a) displaying an image to an operator, the image including a real-time view of an exterior of a uterus of a patient, the uterus having a shaft of a uterine manipulator disposed in the uterus, the uterine manipulator being coupled with a robotic arm, the image being captured by an imaging instrument disposed in the patient; and (b) providing an indicator on the image, the indicator indicating whether a user input feature is in an engaged state or a non-engaged state, the user input feature in the engaged state being operable to control movement of the robotic arm to thereby drive movement of the uterine manipulator.

Example 17

The method of Example 16, the indicator being positioned about the uterus within the real-time view, such that the indicator corresponds to an exterior region of the uterus within the real-time view.

Example 18

The method of any of Examples 16 through 17, further comprising providing a movement overlay on the real-time view, the movement overlay being provided in response to an operator manipulating the user input feature to control movement of the robotic arm to thereby drive movement of the uterine manipulator.

Example 19

The method of Example 18, wherein the operator manipulating the user input feature to control movement of the robotic arm to thereby drive movement of the uterine manipulator results in movement of the uterus, the method further comprising moving one or both of the indicator or the movement overlay with the uterus in the real-time view, based on the movement of the uterus.

Example 20

A processor-readable medium including contents that are configured to cause a processor to: (a) display an image to an operator, the image including a real-time view of an exterior of a uterus of a patient, the uterus having a shaft of a uterine manipulator disposed in the uterus, the uterine manipulator being coupled with a robotic arm, the image being captured by an imaging instrument disposed in the patient; and (b) provide an indicator on the image, the indicator indicating whether a user input feature is in an engaged state or a non-engaged state, the user input feature in the engaged state being operable to control movement of the robotic arm to thereby drive movement of the uterine manipulator.

Example 21

A system, comprising: (a) a uterine manipulator having a shaft, the shaft being configured to pass through a cervix of a patient and enter a uterus of the patient; (b) a robotic arm, the uterine manipulator being coupled with the robotic arm, the robotic arm being operable to drive movement of the uterine manipulator; (c) an imaging instrument operable to provide an image of an exterior of the uterus of the patient; and (d) a console including a display screen, the console being configured to: (i) provide a view from the imaging instrument of the exterior of the uterus of the patient, on the display screen, and (ii) provide an indicator on the view from the imaging instrument, on the display screen, the indicator indicating a location of a predefined anatomical structure, the indicator being provided as an overlay on the predefined anatomical structure.

Example 22

The system of Example 21, the console further being configured to instruct an operator to manipulate the uterus of the patient via the uterine manipulator and robotic arm.

Example 23

The system of any of Examples 21 through 22, the console further being configured to track movement of the predefined anatomical structure within the view from the imaging instrument.

Example 24

The system of Example 23, the console further being configured to move the indicator within the view from the imaging instrument, based on tracked movement of the predefined anatomical structure within the view from the imaging instrument.

Example 25

The system of any of Examples 21 through 24, the console further being configured to receive an input from an operator identifying the location of the predefined anatomical structure in the view from the imaging instrument.

Example 26

The system of any of Examples 21 through 25, the console further being configured to generate the indicator in response to the input from the operator identifying the location of the predefined anatomical structure in the view from the imaging instrument.

Example 27

The system of any of Examples 21 through 26, the console further being configured to automatically identify the location of the predefined anatomical structure in the view from the imaging instrument.

Example 28

The system of Example 27, the console further being configured to generate the indicator in response to the console automatically identifying the location of the predefined anatomical structure in the view from the imaging instrument.

Example 29

The system of any of Examples 27 through 28, the console being configured to automatically identify the location of the predefined anatomical structure in the view from the imaging instrument using optical sensing.

Example 30

The system of Example 29, the optical sensing including one or more of indocyanine green (ICG) fluorescence imaging, multispectral imaging, hyperspectral imaging, photoacoustic imaging, or ultrasonic imaging.

Example 31

The system of any of Examples 21 through 30, the console further being configured to prevent an instrument from contacting the anatomical structure.

Example 32

The system of Example 31, the console further being configured to prevent an instrument from contacting the anatomical structure by preventing a robotic arm coupled with the instrument from being operated to drive the instrument into contact with the anatomical structure.

Example 33

The system of any of Examples 21 through 32, the console further being configured to instruct an operator to provide identification of two or more anatomical structures including the predefined anatomical structure.

Example 34

The system of Example 33, the console further being configured to restrict operation of one or more robotic arms until the operator provides identification of the two or more anatomical structures.

Example 35

The system of any of Examples 21 through 34, the console being configured to provide continued visualization of the indicator when the predefined anatomical structure is obscured by another anatomical structure in the view from the imaging instrument.

Example 36

A method, comprising: (a) displaying an image to an operator, the image including a real-time view of an exterior of a uterus of a patient, the uterus having a shaft of a uterine manipulator disposed in the uterus, the uterine manipulator being coupled with a robotic arm, the image being captured by an imaging instrument disposed in the patient; and (b) providing an indicator on the image, the indicator indicating a location of a predefined anatomical structure, the indicator being provided as an overlay on the predefined anatomical structure.

Example 37

The method of Example 36, further comprising instructing an operator to move the uterus via the uterine manipulator and robotic arm, resulting in movement of the uterus to reveal the predefined anatomical structure.

Example 38

The method of any of Examples 36 through 37, further comprising: (a) instructing an operator to identify a plurality of anatomical structures within the image, the plurality of anatomical structures including the predefined anatomical structure; (b) receiving identifications of the anatomical structures; and (c) providing indicators on the image, the indicators indication locations of the identified anatomical structures.

Example 39

The method of any of Examples 36 through 38, the predefined anatomical structure including one or more ureters.

Example 40

A processor-readable medium including contents that are configured to cause a processor to: (a) display an image to an operator, the image including a real-time view of an exterior of a uterus of a patient, the uterus having a shaft of a uterine manipulator disposed in the uterus, the uterine manipulator being coupled with a robotic arm, the image being captured by an imaging instrument disposed in the patient; and (b) provide an indicator on the image, the indicator indicating a location of a predefined anatomical structure, the indicator being provided as an overlay on the predefined anatomical structure.

VIII. Miscellaneous

For clarity of disclosure, the terms "proximal" and "distal" are defined herein relative to a surgeon or other operator grasping a surgical instrument having a distal surgical end effector. The term "proximal" refers the position of an element closer to the surgeon or other operator and the term "distal" refers to the position of an element closer to the surgical end effector of the surgical instrument and further away from the surgeon or other operator.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

It should be understood that any of the versions of the instruments described herein may include various other features in addition to or in lieu of those described above. By way of example only, any of the devices herein may also include one or more of the various features disclosed in any of the various references that are incorporated by reference herein. Various suitable ways in which such teachings may be combined will be apparent to those of ordinary skill in the art.

While the examples herein are described mainly in the context of electrosurgical instruments, it should be understood that various teachings herein may be readily applied to a variety of other types of devices. By way of example only, the various teachings herein may be readily applied to other types of electrosurgical instruments, tissue graspers, tissue retrieval pouch deploying instruments, surgical staplers, surgical clip appliers, ultrasonic surgical instruments, etc. It should also be understood that the teachings herein may be readily applied to any of the instruments described in any of the references cited herein, such that the teachings herein may be readily combined with the teachings of any of the references cited herein in numerous ways. Other types of instruments into which the teachings herein may be incorporated will be apparent to those of ordinary skill in the art.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. A system, comprising:
   (a) a uterine manipulator having a shaft, the shaft being configured to pass through a cervix of a patient and enter a uterus of the patient;
   (b) a robotic arm, the uterine manipulator being coupled with the robotic arm, the robotic arm being operable to drive movement of the uterine manipulator;
   (c) an imaging instrument operable to provide an image of an exterior of the uterus of the patient; and
   (d) a console including a display screen, the console being configured to:
      (i) provide a view from the imaging instrument of the exterior of the uterus of the patient, on the display screen, and
      (ii) provide an indicator on the view from the imaging instrument, on the display screen, the indicator indicating a location of a predefined anatomical structure, the indicator being provided as an overlay on the predefined anatomical structure; the console being configured to automatically identifying the location of the predefined anatomical structure in the view from the imaging instrument using optical sensing; the optical sensing including one or more of indocyanine green (ICG) fluorescence imaging, multispectral imaging, hyperspectral imaging, photoacoustic imaging, or ultrasonic imaging.

2. The system of claim 1, the console further being configured to instruct an operator to manipulate the uterus of the patient via the uterine manipulator and robotic arm.

3. The system of claim 1, the console further being configured to track movement of the predefined anatomical structure within the view from the imaging instrument.

4. The system of claim 3, the console further being configured to move the indicator within the view from the imaging instrument, based on tracked movement of the predefined anatomical structure within the view from the imaging instrument.

5. The system of claim 1, the console further being configured to receive an input from an operator identifying the location of the predefined anatomical structure in the view from the imaging instrument.

6. The system of claim 1, the console further being configured to generate the indicator in response to the input from the operator identifying the location of the predefined anatomical structure in the view from the imaging instrument.

7. The system of claim 1, the console further being configured to automatically identify the location of the predefined anatomical structure in the view from the imaging instrument.

8. The system of claim 7, the console further being configured to generate the indicator in response to the console automatically identifying the location of the predefined anatomical structure in the view from the imaging instrument.

9. The system of claim 1, the console further being configured to prevent an instrument from contacting the anatomical structure.

10. The system of claim 9, the console further being configured to prevent an instrument from contacting the anatomical structure by preventing a robotic arm coupled with the instrument from being operated to drive the instrument into contact with the anatomical structure.

11. The system of claim 1, the console further being configured to instruct an operator to provide identification of two or more anatomical structures including the predefined anatomical structure.

12. The system of claim 11, the console further being configured to restrict operation of one or more robotic arms until the operator provides identification of the two or more anatomical structures.

13. The system of claim 1, the console being configured to provide continued visualization of the indicator when the predefined anatomical structure is obscured by another anatomical structure in the view from the imaging instrument.

* * * * *